US010245229B2

(12) United States Patent
Heartlein et al.

(10) Patent No.: US 10,245,229 B2
(45) Date of Patent: Apr. 2, 2019

(54) PULMONARY DELIVERY OF MRNA TO NON-LUNG TARGET CELLS

(71) Applicants: Shire Human Genetic Therapies, Inc., Lexington, MA (US); Ethris GmbH, Martinsried (DE)

(72) Inventors: Michael Heartlein, Lexington, MA (US); Braydon Charles Guild, Lexington, MA (US); Frank DeRosa, Lexington, MA (US); Carsten Rudolph, Krailling (DE); Christian Plank, Wessling (DE)

(73) Assignees: Translate Bio, Inc., Lexington, MA (US); Ethris GmbH, Martinsried (DE)

( * ) Notice: Subject to any disclaimer, the term of this patent is extended or adjusted under 35 U.S.C. 154(b) by 0 days.

(21) Appl. No.: 14/406,504

(22) PCT Filed: Jun. 7, 2013

(86) PCT No.: PCT/US2013/044771
§ 371 (c)(1),
(2) Date: Dec. 8, 2014

(87) PCT Pub. No.: WO2013/185069
PCT Pub. Date: Dec. 12, 2013

(65) Prior Publication Data
US 2015/0157565 A1 Jun. 11, 2015

Related U.S. Application Data

(60) Provisional application No. 61/657,452, filed on Jun. 8, 2012.

(51) Int. Cl.
| *A61K 9/127* | (2006.01) |
| *A61K 9/00* | (2006.01) |
| *C12N 15/88* | (2006.01) |
| *A61K 31/7088* | (2006.01) |
| *A61M 15/00* | (2006.01) |
| *A61M 16/14* | (2006.01) |
| *A61K 48/00* | (2006.01) |

(52) U.S. Cl.
CPC ........ *A61K 9/0073* (2013.01); *A61K 31/7088* (2013.01); *A61M 15/009* (2013.01); *A61M 16/14* (2013.01); *C12N 15/88* (2013.01); *A61K 48/0075* (2013.01)

(58) Field of Classification Search
CPC ............. A61K 9/0073; A61K 31/7088; A61K 48/0075; A61M 16/14; A61M 15/009; C12N 15/88
See application file for complete search history.

(56) References Cited

U.S. PATENT DOCUMENTS

| 5,705,385 A | 1/1998 | Bally et al. |
| 5,965,434 A | 10/1999 | Wolff et al. |
| 5,976,567 A | 11/1999 | Wheeler et al. |
| 5,981,501 A | 11/1999 | Wheeler et al. |
| 6,077,835 A | 6/2000 | Hanson et al. |
| 6,534,484 B1 | 3/2003 | Wheeler et al. |
| 6,734,171 B1 | 5/2004 | Saravolac et al. |
| 6,815,432 B2 | 11/2004 | Wheeler et al. |
| 7,422,902 B1 | 9/2008 | Wheeler et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 8,101,741 B2 | 1/2012 | MacLachlan et al. |
| 8,188,263 B2 | 5/2012 | MacLachlan et al. |
| 8,236,943 B2 | 8/2012 | Lee et al. |
| 8,329,070 B2 | 12/2012 | MacLachlan et al. |
| 8,513,403 B2 | 8/2013 | MacLachlan et al. |
| 8,569,256 B2 | 10/2013 | Heyes et al. |
| 8,710,200 B2 | 4/2014 | Schrum et al. |
| 8,822,663 B2 | 9/2014 | Schrum et al. |
| 8,853,377 B2 | 11/2014 | Guild et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,980,864 B2 | 3/2015 | Hoge et al. |
| 8,999,351 B2 | 4/2015 | Manoharan et al. |
| 8,999,950 B2 | 4/2015 | MacLachlan et al. |
| 9,018,187 B2 | 4/2015 | Heyes et al. |
| 9,051,567 B2 | 6/2015 | Fitzgerald et al. |
| 9,061,059 B2 | 6/2015 | Chakraborty et al. |
| 9,074,208 B2 | 7/2015 | MacLachlan et al. |

(Continued)

FOREIGN PATENT DOCUMENTS

| CA | 2807 552 | 9/2012 |
| EP | 1519 714 | 10/2010 |

(Continued)

OTHER PUBLICATIONS

Smola, International journal of Nanomedicine, 2008, 3:1-19.*

(Continued)

*Primary Examiner* — Valarie E Bertoglio
(74) *Attorney, Agent, or Firm* — Proskauer Rose LLP; Fangli Chen; Julio J. Mendez

(57) ABSTRACT

Compositions comprising mRNA formulated for pulmonary administration and related methods for delivery of the mRNA and/or encoded protein to a non-lung cell or tissue. The compositions and methods may be used to prevent or ameliorate the symptoms of diseases associated with the mRNA encoded protein.

18 Claims, 13 Drawing Sheets

Specification includes a Sequence Listing.

(56) References Cited

U.S. PATENT DOCUMENTS

| | | |
|---|---|---|
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,682 B2 | 12/2015 | Manoharan et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,404,127 B2 | 8/2016 | Yaworski et al. |
| 9,428,751 B2 | 8/2016 | MacDonald et al. |
| 9,464,124 B2 | 10/2016 | Bancel et al. |
| 9,492,386 B2 | 11/2016 | MacLachlan et al. |
| 9,504,651 B2 | 11/2016 | MacLachlan et al. |
| 9,504,734 B2 | 11/2016 | Bancel et al. |
| 9,518,272 B2 | 12/2016 | Yaworksi et al. |
| 9,546,128 B2 | 1/2017 | DeRosa et al. |
| 9,572,874 B2 | 2/2017 | Fotin-Mleczek et al. |
| 9,572,896 B2 | 2/2017 | Bancel et al. |
| 9,572,897 B2 | 2/2017 | Bancel et al. |
| 9,587,003 B2 | 3/2017 | Bancel et al. |
| 2002/0192651 A1 | 12/2002 | Wheeler et al. |
| 2003/0181410 A1 | 9/2003 | Wheeler et al. |
| 2004/0142025 A1 | 7/2004 | MacLachlan et al. |
| 2004/0224912 A1 | 11/2004 | Dobie et al. |
| 2005/0158302 A1 | 7/2005 | Faustman et al. |
| 2006/0008910 A1 | 1/2006 | MacLachlan et al. |
| 2006/0083780 A1 | 4/2006 | Heyes et al. |
| 2007/0135372 A1 | 6/2007 | MacLachlan et al. |
| 2009/0270481 A1 | 10/2009 | MacLachlan et al. |
| 2009/0286852 A1 | 11/2009 | Kariko et al. |
| 2010/0041152 A1 | 2/2010 | Wheeler et al. |
| 2011/0244026 A1 | 10/2011 | Guild et al. |
| 2011/0256175 A1 | 10/2011 | Hope et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1 | 9/2012 | Schrum et al. |
| 2012/0251618 A1 | 10/2012 | Schrum et al. |
| 2012/0328668 A1 | 12/2012 | MacLachlan et al. |
| 2013/0177640 A1* | 7/2013 | Geall .................. C12N 15/111 424/450 |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0213785 A1 | 7/2016 | Monoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |
| 2016/0367702 A1 | 12/2016 | Hoge et al. |
| 2016/0375134 A1 | 12/2016 | Bancel et al. |
| 2016/0375137 A9 | 12/2016 | Manoharan et al. |
| 2017/0000858 A1 | 1/2017 | Fotin-Mleczek et al. |
| 2017/0000870 A1 | 1/2017 | Hoerr et al. |
| 2017/0000871 A1 | 1/2017 | Probst et al. |

(56) References Cited

U.S. PATENT DOCUMENTS

| | | |
|---|---|---|
| 2017/0002060 A1 | 1/2017 | Bolen et al. |
| 2017/0007702 A1 | 1/2017 | Heyes et al. |
| 2017/0014496 A1 | 1/2017 | Fotin-Mleczek et al. |
| 2017/0028059 A1 | 2/2017 | Baumhof et al. |
| 2017/0029847 A1 | 2/2017 | Thess |
| 2017/0042814 A1 | 2/2017 | Yaworski et al. |
| 2017/0056529 A1 | 3/2017 | Thess et al. |

FOREIGN PATENT DOCUMENTS

| | | |
|---|---|---|
| EP | 2449 106 | 5/2012 |
| EP | 2338 478 | 6/2013 |
| EP | 2823 809 | 1/2015 |
| WO | 1990/011092 A1 | 3/1990 |
| WO | 1993/003709 A1 | 3/1993 |
| WO | 1993/03709 A1 | 5/1993 |
| WO | 1993/012756 A2 | 7/1993 |
| WO | WO1993/012756 | 7/1993 |
| WO | 1998/010748 A1 | 3/1998 |
| WO | WO1998/010748 | 3/1998 |
| WO | 2000/059548 A1 | 10/2000 |
| WO | 2004/067026 A1 | 8/2004 |
| WO | WO2005/026372 | 3/2005 |
| WO | 2005/120152 A2 | 12/2005 |
| WO | WO2005/121348 | 12/2005 |
| WO | 2006/016097 A2 | 2/2006 |
| WO | WO2006/016097 | 2/2006 |
| WO | WO2009/127060 | 10/2006 |
| WO | 2007/024708 A2 | 3/2007 |
| WO | WO2010/042877 | 4/2010 |
| WO | 2010/056403 A1 | 5/2010 |
| WO | WO2010/056403 | 5/2010 |
| WO | 2010/110314 A1 | 9/2010 |
| WO | 2011/068810 A1 | 6/2011 |
| WO | 2011/071931 A2 | 6/2011 |
| WO | WO2011/141705 | 11/2011 |
| WO | WO2012/019168 | 2/2012 |
| WO | WO2012/170930 | 6/2012 |
| WO | WO2012/135805 | 10/2012 |
| WO | WO2013/039857 | 3/2013 |
| WO | WO2013/039861 | 3/2013 |
| WO | WO2013/090186 | 6/2013 |
| WO | WO2013/101690 | 7/2013 |
| WO | WO2013/126803 | 8/2013 |
| WO | WO2013/130161 | 9/2013 |
| WO | 2013/149140 A1 | 10/2013 |
| WO | WO2013/151663 | 10/2013 |
| WO | WO2013/151664 | 10/2013 |
| WO | WO2013/151666 | 10/2013 |
| WO | WO2013/151667 | 10/2013 |
| WO | WO2013/151668 | 10/2013 |
| WO | WO2013/151670 | 10/2013 |
| WO | WO2013/151671 | 10/2013 |
| WO | WO2013/151672 | 10/2013 |
| WO | WO2013/151736 | 10/2013 |
| WO | WO2014/089486 | 12/2013 |
| WO | WO2014/113089 | 7/2014 |
| WO | WO2014/144039 | 9/2014 |
| WO | WO2014/144711 | 9/2014 |
| WO | WO2014/144767 | 9/2014 |
| WO | WO2014/152027 | 9/2014 |
| WO | WO2014/152030 | 9/2014 |
| WO | WO2014/152031 | 9/2014 |
| WO | WO2014/152211 | 9/2014 |
| WO | WO2014/152540 | 9/2014 |
| WO | WO2014/158795 | 10/2014 |
| WO | WO2014/159813 | 10/2014 |
| WO | WO2015/006747 | 1/2015 |
| WO | WO2015/048744 | 4/2015 |
| WO | WO2015/051169 | 4/2015 |
| WO | WO2015/051173 | 4/2015 |
| WO | WO2015/058069 | 4/2015 |
| WO | WO2015/085318 | 6/2015 |
| WO | WO2015/089511 | 6/2015 |
| WO | WO2015/011633 | 1/2016 |
| WO | WO2016/054421 | 4/2016 |
| WO | WO2016/071857 | 5/2016 |
| WO | WO2016/077123 | 5/2016 |
| WO | WO2016/077125 | 5/2016 |
| WO | WO2016/118724 | 7/2016 |
| WO | WO2016/118725 | 7/2016 |
| WO | WO2016/154127 | 9/2016 |
| WO | WO2016/164762 | 10/2016 |
| WO | WO2016/183366 A2 | 11/2016 |
| WO | WO2016/197132 A1 | 12/2016 |
| WO | WO2016/197133 A1 | 12/2016 |
| WO | WO2016/201377 A1 | 12/2016 |
| WO | WO2017/019891 A2 | 2/2017 |

OTHER PUBLICATIONS

Pardi (Journal of Controlled Release, 2015, 217:345-351).*
Liu (2008, Int'l Jour Pharmaceutics, 3556:333-344).*
Ryan (2008, Expert Opin Drug Deliv 5:371-383).*
Phua (2013, Journal of Controlled Release, 166:227-233).*
Su (2011, Molecular Pharmaceutics, 8:774-787).*
Lam, et al., Pulmonary delivery of therapeutic siRNA, Advanced Drug Delivery Reviews, ePub Feb. 26, 2011, vol. 64, Issue 1, pp. 1-15. Especially Abstract.
Schreier, et al., The new frontier: gene and oligonucleotide therapy, Pharmaceutica Acta Helvetiae, Jan. 1994, 68(1994) Issue 3, 145-159. Especially Abstract.
Burger et al., "Sequencing complete mitochondrial and plastid genomes", Nature Protocols, 2(3): 603-14 (2007).
Driscoll et al., "Intratracheal Instillation as an Exposure Technique for the Evaluation of Respiratory Tract Toxicity: Uses and Limitations", Toxicological Sciences, 55: 25-35 (2000).
Kormann et al., "Expression of therapeutic proteins after delivery of chemically modified mRNA in mice", Nature Biotechnology, 29(2): 154-9 (2011).
Rudolph et al., "Methodological optimization of polyethylenimine (PEI)-based gene delivery to the lungs of mice via aerosol application", The Journal of Gene Medicine, 7: 59-66 (2005).
Rudolph et al., "Aerosolized Nanogram Quantities of Plasmid DNA Mediate Highly Efficient Gene Delivery to Mouse Airway Epithelium", Molecular Therapy, 12(3): 493-501 (2005).
Su et al. "InVitro and in Vivo mRNA Delivery Using Lipid-Enveloped pH-Responsive Polymer Nanoparticles", Molecular Pharmaceutics, 8(3): 774-8 (2011).
Love, K. et al., "Lipid-like materials for low-dose, in vivo gene silencing", PNAS, 107 (5): 1864-1869 (Feb. 2, 2010).

* cited by examiner

PULMONARY DELIVERY OF MRNA TO NON-LUNG TARGET CELLS

RELATED APPLICATIONS

This application is the National Stage of International Application PCT/US2013/044771, filed Jun. 7, 2013, which claims the benefit of U.S. Provisional Application No. 61/657,452, filed on Jun. 8, 2012, the contents of all of which are incorporated herein by reference in their entirety.

SEQUENCE LISTING

The present specification makes reference to a Sequence Listing (submitted electronically as a .txt file named "SequenceListing2006685-0333_ST25.txt" concurrently with other documents associated with this application on Jun. 7, 2013). The .txt file was created on Jun. 7, 2013 and is 1.26 KB in size. The entire contents of the Sequence Listing are herein incorporated by reference.

BACKGROUND

Conventional gene therapy involves the use of DNA for insertion of desired genetic information into host cells. The DNA introduced into the cell is usually integrated into the genome of one or more transfected cells, allowing for long-lasting action of the introduced genetic material in the host. While there may be substantial benefits to such sustained action, integration of exogenous DNA into a host genome may also have many deleterious effects. For example, it is possible that the introduced DNA will be inserted into an intact gene, resulting in a mutation which impedes or even totally eliminates the function of the endogenous gene. Thus, gene therapy with DNA may result in the impairment of a vital genetic function in the treated host, such as e.g., elimination or deleteriously reduced production of an essential enzyme or interruption of a gene critical for the regulation of cell growth, resulting in unregulated or cancerous cell proliferation. In addition, with conventional DNA based gene therapy it is necessary for effective expression of the desired gene product to include a strong promoter sequence, which again may lead to undesirable changes in the regulation of normal gene expression in the cell. It is also possible that the DNA based genetic material will result in the induction of undesired anti-DNA antibodies, which in turn, may trigger a possibly fatal immune response.

In contrast to DNA, the use of RNA as a gene therapy agent is substantially safer because (1) RNA does not involve the risk of being stably integrated into the genome of the transfected cell, thus eliminating the concern that the introduced genetic material will disrupt the normal functioning of an essential gene, or cause a mutation that results in deleterious or oncogenic effects; (2) extraneous promoter sequences are not required for effective translation of the encoded protein, again avoiding possible deleterious side effects; (3) in contrast to plasmid DNA (pDNA), messenger RNA (mRNA) is devoid of immunogenic CpG motifs so that anti-RNA antibodies are not generated; and (4) any deleterious effects that do result from mRNA based on gene therapy would be of limited duration due to the relatively short half-life of RNA. Moreover in many applications, the transient nature of mRNA transfer to cells, i.e., wherein the duration of any therapeutic effect is limited by the life span of the mRNA and the protein product in the cells, is more desirable than the potentially longer lasting effect achieved using DNA based gene therapy. In addition, it is not necessary for mRNA to enter the nucleus to perform its function, thus avoiding a major barrier to DNA based gene therapy.

One reason that mRNA based gene therapy has not been used more in the past is that mRNA is far less stable than DNA, especially when it reaches the cytoplasm of a cell and is exposed to degrading enzymes. The presence of a hydroxyl group on the second carbon of the sugar moiety in mRNA causes steric hinderance that prevents the mRNA from forming the more stable double helix structure of DNA and thus makes the mRNA more prone to hydrolytic degradation. As a result, until recently, it was widely believed that mRNA was too labile to withstand transfection protocols.

Advances in RNA stabilizing modifications have sparked more interest in the use of mRNA in place of plasmid DNA in gene therapy. Yet, in spite of increased stability of modified mRNA, delivery of mRNA to cells in vivo in a manner allowing for therapeutic levels of protein production is still a challenge, particularly for mRNA encoding full length proteins. Some success has been achieved using viral vectors to introduce mRNA into a host, however mRNA transfection using viral vectors can result in an adverse immune response. In some circumstances, the viral vector may even integrate into the host genome. In addition, production of clinical grade viral vectors is also expensive and time consuming. Targeting delivery of the introduced genetic material using viral vectors can also be difficult to control.

Non-viral delivery of mRNA can be achieved using injection of naked nucleic acids, polyplexes, lipoplexes or liposome entrapped mRNA, biolistic delivery via gene gun, particulate carrier mediated delivery, and electroporation. Non-viral transfection or delivery vehicles are generally less-toxic, less immunogenic, and easier and less expensive to prepare than viral vectors for delivery of mRNA. Certain delivery vehicles, such as cationic lipid or polymer delivery vehicles may also help protect the transfected mRNA from endogenous RNases.

Liposomal delivery of nucleic acids has been employed as a means of effectuating the site-specific delivery of encapsulated plasmid DNA, antisense oligonucleotides, short interfering RNA and microRNA-based therapies. However the efficient, therapeutically effective, delivery of mRNAs to targeted cells and tissues, as well as the subsequent transfection of such targeted cells and tissues remains a technical challenge, particularly for delivery of mRNAs encoding full length proteins. It is important to design liposomal delivery systems that provide sufficient stability to reach desired target cells and the ability to efficiently release their encapsulated materials to such target cells to allow for translation of functional protein at therapeutically effective levels.

Many cationic lipids that are employed to construct such liposomal-based delivery vehicles are toxic to the targeted cells when used to deliver therapeutically effective amounts of the encapsulated agent. Accordingly, the toxicity associated with cationic lipid represents a significant obstacle to their general use as non-viral delivery vehicles, particularly in the quantities necessary to successfully deliver therapeutically effective amounts of mRNA to target cells.

To date, significant progress using mRNA gene therapy has been made in applications, particularly for which low levels of translation has not been a limiting factor, such as immunization with mRNA encoding antigens. Clinical trials involving vaccination against tumor antigens by intradermal injection of naked or protamine-complexed mRNA have demonstrated feasibility, lack of toxicity, and promising results. X. Su et al., *Mol. Pharmaceutics* 8:774-787 (2011). However, low levels of translation can restrict the exploitation of mRNA based gene therapy in other applications which require higher levels of sustained stability of the mRNA encoded protein to exert a prolonged biological or therapeutic effect.

In addition, because mRNA gene therapy benefits are relatively transient as compared to DNA based gene therapy, repeated administration, and typically by injection, are often required to provide long term effects. Thus, more efficient transfection in vivo and the ability to deliver mRNA non-invasively and/or to mucosal sites would improve the prospects for successful application of mRNA gene therapy.

SUMMARY

The present invention encompasses the surprising discovery that nanoparticle based formulations of mRNA are able to translocate following pulmonary delivery, i.e., move intact by either active or passive means from the lung to the systemic blood supply and subsequently to be deposited in different non-lung cells or tissues, such as, e.g., the liver. This translocation of the nanoparticle comprising an mRNA encoding a therapeutic protein, such as, e.g., beta-galactosidase, constitutes non-invasive systemic delivery of an active pharmaceutical ingredient beyond the lung to result in the production of a functional protein to systemically accessible non-lung cells or tissues.

Thus, the present invention provides methods for delivery of mRNA gene therapeutic agents using non-invasive pulmonary administrations. Among other things, the present invention provides for the delivery of mRNA encoding a protein, which can be used in a method for treating and/or preventing a disease. In one particular aspect, the invention provides a method for delivery of messenger RNA (mRNA) to non-lung cell or tissue comprising administering to the lung a composition comprising mRNA encoding a protein and a lipid carrier vehicle, wherein the administering to the lung results in the delivery of the mRNA and/or the protein to a non-lung cell or tissue.

In another aspect, the invention provides a method for delivery of a therapeutic protein to non-lung cell or tissue in a subject comprising administering to the lung a composition comprising mRNA encoding a therapeutic protein and a lipid carrier vehicle, such that the therapeutic protein is delivered to a non-lung cell or tissue.

In another aspect, the invention provides a method of inducing the production of a therapeutic protein in a non-lung cell or tissue in a subject comprising administering to the lung a composition comprising mRNA encoding a therapeutic protein and a lipid carrier vehicle.

In another aspect, the invention provides a method of treating a disease or disorder comprising administering to the lung a composition comprising mRNA encoding a therapeutic protein and a lipid carrier vehicle, wherein the administration to the lung results in the delivery of the therapeutic protein to a non-lung cell or tissue affected by the disease or disorder.

In another aspect, the invention provides a composition for pulmonary delivery of messenger RNA (mRNA) comprising mRNA encoding a protein and a lipid carrier vehicle, wherein the composition is formulated such that once administered to the lung, it results in delivery of the mRNA and/or the protein to a non-lung cell or tissue.

In some embodiments, the composition is administered to the lung by aerosolization. In some embodiments, the composition is delivered to the lung by intratracheal aerosolization. In some embodiments, the composition is administered by nebulization. In some embodiments, the composition is administered to the lung by instillation. In some specific embodiments, the composition is administered to the lung of a subject using a device selected form the group consisting of a metered dose inhaler, jet-nebulizer, ultrasonic nebulizer, dry-powder-inhaler, propellant-based inhaler or an insufflator.

In some embodiments, the mRNA comprises a plurality of mRNA species, encoding one or more proteins. In some embodiments, the mRNA comprises at least two mRNA species, each encoding a different protein. In some embodiments, the mRNA encodes a full length protein. In some embodiments, the mRNA encodes a truncated version of a naturally occurring full length protein. In some embodiments, the mRNA encodes one or more proteins in a single transcript. In some embodiments, the mRNA encodes a chimeric protein, in which one or more protein sequences which are not naturally associated with the native protein are linked by a peptide bond in the resulting chimeric protein during expression. In some embodiments, an mRNA suitable for the present invention has a length of or greater than about 0.5 kb, 1 kb, 1.5 kb, 2.0 kb, 2.5 kb, 3.0 kb, 3.5 kb, 4.0 kb, 4.5 kb, or 5.0 kb.

In some embodiments, the mRNA encodes an intracellular protein. In some embodiments, the mRNA encodes a cytosolic protein. In some embodiments, the mRNA encodes a protein associated with the actin cytoskeleton. In some embodiments, the mRNA encodes a protein associated with the plasma membrane. In some specific embodiments, the mRNA encodes a transmembrane protein. In some specific embodiments, the mRNA encodes an ion channel protein. In some embodiments, the mRNA encodes a perinuclear protein. In some embodiments, the mRNA encodes a nuclear protein. In some specific embodiments, the mRNA encodes a transcription factor. In some embodiments, the mRNA encodes a chaperone protein. In some embodiments, the mRNA encodes an intracellular enzyme. In some embodiments, the mRNA encodes a protein involved in cellular metabolism, DNA repair, transcription and/or translation. In some embodiments, the mRNA encodes an extracellular protein. In some embodiments, the mRNA encodes a protein associated with the extracellular matrix. In some embodiments the mRNA encodes a secreted protein.

In some embodiments, the mRNA encodes a protein (i.e. therapeutic protein), listed in Table 1, 2, 3 or 4. In some specific embodiments, the protein is selected from the group consisting of alpha galactosidase, erythropoietin, α1-antitrypsin, carboxypeptidase N, alpha-L-iduronidase, iduronate-2-sulfatase, N-acetylglucosamine-1-phosphate transferase, N-acetylglucosaminidase, lysosomal acid lipase, arylsulfatase-A alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase, galactocerebrosidase, human growth hormone, ornithine transcarbamylase (OTC), carbamyl phosphate synthetase-1 (CPS1), argininosuccinate synthetase-1 (ASS1), argininosuccinate lyase (ASL), arginase-1 (ARG1), cystic fibrosis transmembrane conductance regulator (CFTR), Factor VII, Factor VIII, Factor IX, heparan-N-sulfatase, and combinations thereof. In some specific embodiments, the protein is an intracellular or transmembrane protein selected from the group consisting of ornithine transcarbamylase (OTC), carbamyl phosphate synthetase-1 (CPS1), argininosuccinate synthetase-1 (ASS1), argninosuccinate lyase (ASL), arginase-1 (ARG1), cystic fibrosis transmembrane conductance regulator (CFTR), and combinations thereof.

In some embodiments, the mRNA encodes a protein that is associated with a disease or disorder (i.e., indication) listed in Table 4. In some embodiments, the protein for use in the method, is selected based on its ability to prevent, treat and/or cure a subject affected with a disease or disorder (i.e., indication) listed in Table 4. In specific embodiments, the disease or disorder is selected from the group consisting of SMN1-related spinal muscular atrophy (SMA), amyotrophic lateral sclerosis (ALS), GALT-related galactosemia, Cystic Fibrosis (CF), SLC3A1-related disorders, cystinuria, COL4A5-related disorders, Alport syndrome, galactocerebrosidase deficiencies, X-linked adrenoleukodystrophy, adrenomyeloneuropathy, Friedreich's ataxia, Pelizaeus-Merzbacher disease, TSC1 or TSC2-related tuberous sclerosis, Sanfilippo B syndrome (MPS IIIB), CTNS-related cystinosis, the FMR1-related disorders, include Fragile X syndrome, Fragile X-Associated Tremor/Ataxia Syndrome, Fragile X Premature Ovarian Failure Syndrome, Prader-Willi syndrome, Fabry disease, hereditary hemorrhagic telangiectasia (AT), Niemann-Pick disease Type C1, neuronal ceroid lipofuscinoses-related diseases, Juvenile Neuronal Ceroid Lipofuscinosis (JNCL), Juvenile Batten disease, Santavuori-Haltia disease, Jansky-Bielschowsky disease, PTT-1 deficiency, TPP1 deficiency, EIF2B1, EIF2B2, EIF2B3, EIF2B4 and EIF2B5-related childhood ataxia with central nervous system hypomyelination/vanishing white matter, CACNA1A and CACNB4-related Episodic Ataxia Type 2, the MECP2-related disorders, Classic Rett Syndrome, MECP2-related Severe Neonatal Encephalopathy, PPM-X Syndrome, CDKL5-related Atypical Rett Syndrome, Kennedy's disease (SBMA), Notch-3 related cerebral autosomal dominant arteriopathy with subcortical infarcts and leukoencephalopathy (CADASIL), SCN1A and SCN1B-related seizure disorders, Polymerase G-related disorders, Alpers-Huttenlocher syndrome, POLG-related sensory ataxic neuropathy, dysarthria, ophthalmoparesis, autosomal dominant and recessive progressive external ophthalmoplegia with mitochondrial DNA deletions, X-Linked adrenal hypoplasia, X-linked agammaglobulinemia, Wilson's disease, and blood clotting disorders.

In some embodiments, following delivery to the lung, the mRNA and/or protein is delivered to a non-lung tissue. In some embodiments, the non-lung tissue comprises any organ and/or organ system of the body, excluding the lungs. In some specific embodiments, the non-lung tissue is selected from the group consisting of heart, liver, spleen, kidneys, skeletal muscle, lymph nodes, brain skin, cerebrospinal fluid, plasma and combinations thereof. In some specific embodiments, the non-lung tissue is liver. In some specific embodiments, the non-lung tissue is heart. In some specific embodiments, the non-lung tissue is spleen.

In some embodiments, following delivery to the lung, the mRNA and/or protein is delivered to a non-lung cell. In some embodiments, the non-lung cell is selected from the group consisting of hepatocytes, epithelial cells, hematopoietic cells, epithelial cells, endothelial cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, tumor cells, macrophages, neutrophils, antigen presenting cells (dendritic cells), fibroblasts and combination thereof. In some specific embodiments, the non-lung cell is a hepatocyte.

In some embodiments, the mRNA and/or protein is detectable in the non-lung cell and/or tissue for at least about 4 hours, 6 hours, 8 hours, 10 hours, 12 hours, 18 hours, 24 hours, or more following the administration to the lung. In some embodiments, the mRNA and/or protein is detectable in the non-lung cell and/or tissue for at least about 1 day, 2 days, 3 days, 4 days, 5 days, 6 days, 7 days, 8 days, 9 days or 10 days following the administration to the lung. In some embodiments, the mRNA and/or protein is detectable in the non-lung cell and/or tissue for at least about 1 week, 2 weeks, 3 weeks, 4 weeks, 5 weeks, or 6 weeks following administration to the lung. In some embodiments, the mRNA is detected using a methods selected the group consisting of in-situ hybridization, RT-PCR, Real-Time RT-PCR, Northern Blot, nuclease protection assay and combinations thereof. In some embodiments, the protein is detected using a methods selected from the group consisting of Western Blot, ELISA, immunoprecipitation, BCA assay, immunohistochemistry and combinations thereof.

In some embodiments, the mRNA is delivered at an amount greater than about 0.5 mg/kg (e.g., greater than about 1.0 mg/kg, 1.5 mg/kg, 2.0 mg/kg, 2.5 mg/kg, 3.0 mg/kg, 4.0 mg/kg, 5.0 mg/kg, 6.0 mg/kg, 7.0 mg/kg, 8.0 mg/kg, 9.0 mg/kg, or 10.0 mg/kg) body weight of mRNA per dose. In some embodiments, the mRNA is delivered at an amount ranging from about 0.1-100 mg/kg (e.g., about 0.1-90 mg/kg, 0.1-80 mg/kg, 0.1-70 mg/kg, 0.1-60 mg/kg, 0.1-50 mg/kg, 0.1-40 mg/kg, 0.1-30 mg/kg, 0.1-20 mg/kg, 0.1-10 mg/kg) body weight of mRNA per dose. In some embodiments, the mRNA is delivered at an amount of or greater than about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, or 500 mg per dose.

In some embodiments, the mRNA is encapsulated in a single lipid carrier vehicle. In some embodiments, the mRNA is encapsulated in one or more lipid carrier vehicles. In some embodiments, the mRNA is encapsulated in one or more lipid carrier vehicles, which differ in their lipid composition, molar ratio of lipid components, size, charge (Zeta potential), targeting ligands and combinations thereof.

In some embodiments, the lipid carrier vehicle is a liposome. In some embodiments, the liposome comprises one or more cationic lipids, one or more non-cationic lipids, one or more cholesterol-based lipids and one or more PEG-modified lipids. In some embodiments, the one or more cationic lipid is an ionizable lipid. In some embodiments, the one or more cationic lipid is a cleavable lipid. In some embodiments, the one or more cationic lipid is a cholesterol-derived cationic lipid. In some embodiments, the one or more cationic lipids are selected from C12-200, HGT4003, HGT5000, HGT5001, RE-1, RE-2, RE-3, ICE, GL-67, DLinKC2-DMA, DODAP, DODMA, DLinDMA, CLinDMA and combinations thereof.

In some embodiments, the composition further comprises a pulmonary surfactant. In some embodiments, the composition is formulated as respirable particles. In some embodiments, the respirable particles have a size less than about 500 μm (e.g., less than about 450 μm, 400 μm, 350 μm, 300 μm, 250 μm, 200 μm, 150 μm, 100 μm, or 50 μm). In some embodiments, the composition is formulated as a nebulizable lipid. In some embodiments, the composition is formulated as a dry powder.

In various embodiments, the invention also provides a composition comprising mRNA encoding a protein and a lipid carrier vehicle as described herein for use in a method of delivery of messenger RNA (mRNA) to a non-lung cell or tissue, wherein the method comprises a step of administering the composition to the lung of a subject and further wherein the administering to the lung results in the delivery of the mRNA and/or protein to the non-lung cell or tissue.

In various embodiments, the invention provides a composition comprising mRNA encoding a protein and a lipid carrier vehicle as described herein for use in a method for delivery of therapeutic protein to a non-lung cell or tissue, wherein the method comprises a step of administering the composition to the lung of a subject.

In various embodiments, the invention provides a composition comprising mRNA encoding a protein and a lipid carrier vehicle as described herein for use in a method for inducing the production of a protein in a non-lung cell or tissue, wherein the method comprises a step of administering the composition to the lung.

In various embodiments, the invention provides a composition comprising mRNA encoding a protein and a lipid carrier vehicle as described herein for use in treating a disease or disorder, wherein the method comprises a step of administering the composition to the lung and further wherein the administering to the lung results in the delivery of mRNA and/or protein to a non-lung cell or tissue affected by the disease or disorder.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DEFINITIONS

Figure 1:
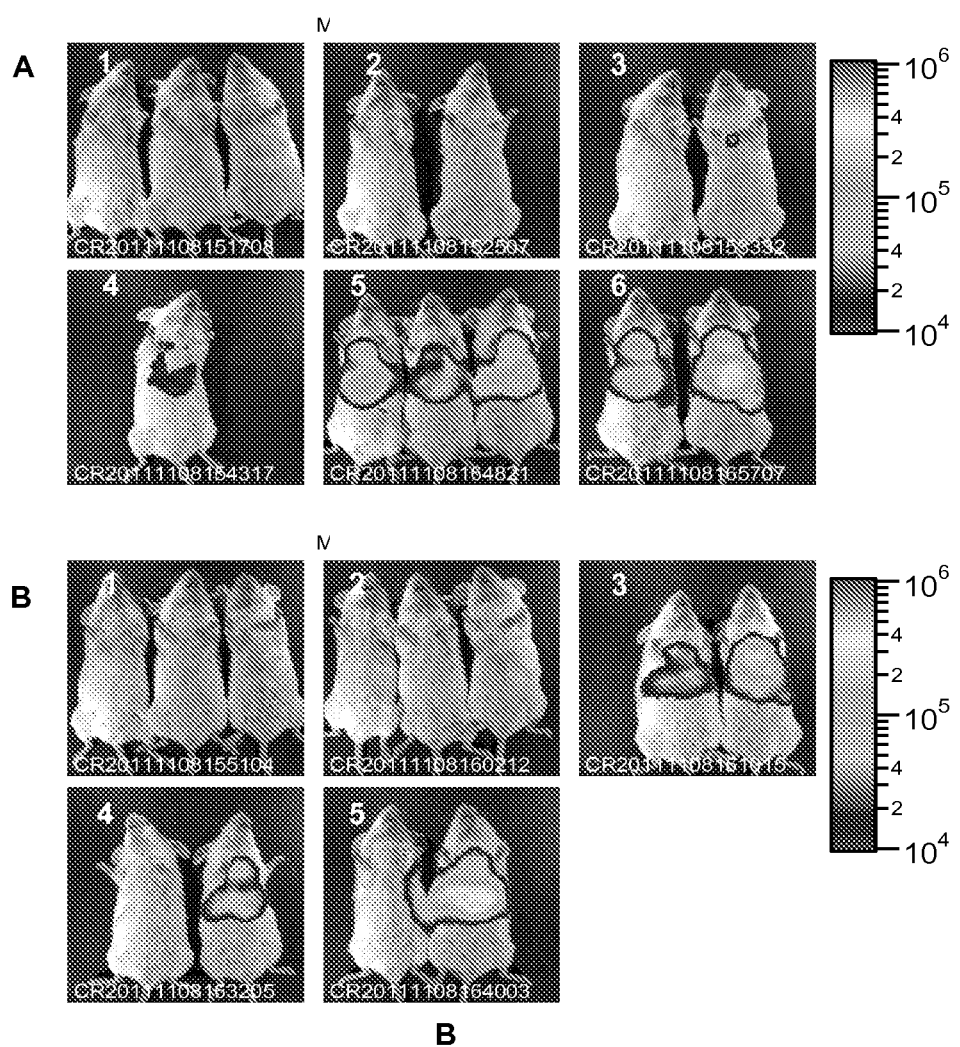
FIG. 1 shows bioluminescence Imaging (BLI) of mice at 6 hrs post intratracheal (IT) spray application. (A) Panels 1, 2, 3 show protein production in mice treated with naked FFL mRNA compared with protein production in mice treated with FFL mRNA in C12-200:DOPE:Cholesterol:DMG-PEG2000 (40:30:25:5) nanoparticles (NPs) in panels 4, 5, 6. (B) Panels 1, 2 (naked modified FFL mRNA) compared to panels 3, 4, 5 (modified FFL mRNA in C12-200 based NPs).

In order for the present invention to be more readily understood, certain terms are first defined below. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regiment, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In this application, the terms "expression" and "production," and grammatical equivalent, are used inter-changeably.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Protein: As used herein, the term "protein" of "therapeutic protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition (e.g., influenza). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION

The present invention provides, among other things, methods and compositions for systemic delivery of mRNA and/or its protein product based on pulmonary delivery. In some embodiments, the present invention provides a method of administering a composition comprising mRNA and a lipid carrier vehicle to the lungs of a subject, for delivery of the mRNA and/or protein to non-lung cells and tissues. In some embodiments, mRNA encoding a single protein are delivered. In some embodiments one or more mRNA species encoding one or more proteins are delivered. In some embodiments, the mRNA is delivered using a single lipid carrier vehicle (e.g. liposome or lipid-derived nanoparticle). In some embodiments the mRNA is delivered using a one or more lipid carrier vehicles.

Various aspects of the invention are described in detail in the following sections. The use of sections is not meant to limit the invention. Each section can apply to any aspect of the invention. In this application, the use of "or" means "and/or" unless stated otherwise.

mRNA and mRNA Synthesis mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for a desired mRNA and a termination signal.

Desired mRNA sequence according to the invention may be determined and incorporated into a DNA template using standard methods. For example, starting from a desired amino acid sequence a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

mRNA according to the present invention may be synthesized as unmodified or modified mRNA. In some embodiments, the mRNA may include one or more chemical or structural modifications to abrogate mRNA interaction with toll-like receptors TLR3, TLR7, TLR8, and retinoid-inducible gene I (RIG-I) to reduce immunogenicity as well as improve stability of the mRNA.

For example, in certain embodiments, the mRNA may be modified as described in U.S. patent publication 2009/0286852 (incorporated herein by reference), to comprise one or more pseudouridine residues. Kormann et al., Nature Biotechnology 29(2):154-157 (2011) describe replacement of uridine and cytidine with 2-thiouridine and 5-methylcytidine to synergistically decrease mRNA binding to pattern recognition receptors TLR3, TLR7, TLR8, and RIG-I and increase stability of the mRNA. See EP2459231. In yet other embodiments, the mRNA may be modified to reduce immunogenicity as described in European Application EP10742089 (incorporated herein by reference).

In other embodiments, modifications of mRNA can include, for example, modifications of the nucleotides of the RNA. An modified mRNA according to the invention can thus include, for example, backbone modifications, sugar modifications or base modifications. In some embodiments, mRNAs encoding a protein of interest may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxy-acetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference. See G. Tavernier et al., *J. Controlled Release* 150:238-247 (2011) and WO 2010/053572, incorporated herein by reference. See also US 2009/0286852 providing an extensive list of modified nucleosides, at ¶¶55, and 68-75 and WO 2008/052770 (incorporated herein by reference) describing numerous mRNA modifications for increasing mRNA stability and protein production.

In some embodiments, mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

In certain embodiments, stabilizing modifications may be made to either or both the 3' and 5' ends of the mRNA and include, e.g., end capping, polyA tail, replacement of unstable non-coding sequences (such as adenylate uridylate rich elements (AREs) or addition or 3' or 5' untranslated sequences from stable mRNA (such as, e.g., β-globin, actin, GAPDH, tubulin, histone, or citric acid cycle enzyme mRNA). Stabilizing modifications may also be made within the mRNA, and include, e.g., codon optimization and/or modification of the Kozak sequence, and/or incorporation of modified nucleosides (such as, e.g., pyrrolo-pyrimidine, C5-iodouridine, 2-amino adenosine, and 2-thiothymidine). In certain embodiments, the modified mRNA used in the methods and compositions of the invention include a 5' untranslated sequence from CMV immediate-early 1 (IE1) gene: XCAGAUCGCCUGGAGACGCCAUCCACGCU-GUUUUGACCUCCAUAGAAGACACC GGGAC-CGAUCCAGCCUCCGCGGCCGGGAACGGUG-CAUUGGAACGCGGAUUCCC CGUGCCAAGAGUG-ACUCACCGUCCUUGACACG, wherein X, if present is GGA (SEQ ID NO:1), or a sequence that is at least 90% or at least 95% identical to SEQ ID NO:1, or a and/or a 3'untranslated sequence from human growth hormone (hGH) gene: CGGGUGGCAUCCCUGUGACCCCUC-CCCAGUGCCUCUCCUGGCCCUGGAAGUUG CCA-CUCCAGUGCCCACCAGCCUUGUC-CUAAUAAAAUUAAGUUGCAUC (SEQ ID NO:2), or a sequence that is at least 90% or at least 95% identical to SEQ ID NO:2, to improve the nuclease resistance and/or improve the half-life of the mRNA. In addition to increasing the stability of the mRNA polynucleotide sequence, it has been surprisingly discovered the inclusion of the untranslated sequence of CMV immediate-early 1 (IE1) gene and/or the untranslated sequence from the hGH gene further enhances the translation of the mRNA.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs of the current invention include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs of the current invention include a 3' poly(A) tail structure. A poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs of the current invention include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs of the current invention include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Proteins Encoded by mRNAs

The mRNAs used in the compositions and methods of the invention may be used to express full length, truncated, native or modified protein for delivery to non-lung tissue and cells. In some embodiments, the mRNA comprises at least one mRNA species encoding a protein (i.e. a therapeutic protein). In some embodiments, the mRNA comprises a plurality of mRNA species, encoding one or more gene products. In some embodiments, the mRNA comprises at least two mRNA species, each encoding a different gene product. In some embodiments, the mRNA encodes a full length protein. In some embodiments, the mRNA encode a truncated version of the naturally occurring full length protein. In some embodiments, the mRNA encode one or more truncated protein from different gene products in a single transcript. In some embodiments, the mRNA encodes a chimeric protein, in which one or more protein sequences which are not naturally associated with the native protein are linked by a peptide bond in the resulting chimeric protein during expression. In some embodiments, the mRNA may be used to express a partial or full length protein comprising cellular activity at a level equal to or greater than that of the native protein. In some embodiments, the mRNA may be used to express a partial or full length protein with cellular activity at a level equal to or less than that of the native protein.

In some embodiments the mRNA encodes an intracellular protein. In some embodiments, the mRNA encodes a cytosolic protein. In some embodiments, the mRNA encodes a protein associated with the actin cytoskeleton. In some embodiments, the mRNA encodes a protein associated with the plasma membrane. In some specific embodiments, the mRNA encodes a transmembrane protein. In some specific embodiments the mRNA encodes an ion channel protein. In some embodiments, the mRNA encodes a perinuclear protein. In some embodiments, the mRNA encodes a nuclear protein. In some specific embodiments, the mRNA encodes a transcription factor. In some embodiments, the mRNA encodes a chaperone protein. In some embodiments, the mRNA encodes an intracellular enzyme (e.g., mRNA encoding an enzyme associated with urea cycle or lysosomal storage metabolic disorders). In some embodiments, the mRNA encodes a protein involved in cellular metabolism, DNA repair, transcription and/or translation. In some embodiments, the mRNA encodes an extracellular protein. In some embodiments, the mRNA encodes a protein associated with the extracellular matrix. In some embodiments the mRNA encodes a secreted protein. In specific embodiments, the mRNA used in the composition and methods of the invention may be used to express functional proteins or enzymes that are excreted or secreted by one or more target cells into the surrounding extracellular fluid (e.g., mRNA encoding hormones and neurotransmitters)

In some embodiments, the compositions and methods of the invention provide for delivery of mRNA encoding a secreted protein. In some embodiments, the compositions and methods of the invention provide for delivery of mRNA encoding one or more secreted proteins listed in Table 1; thus, compositions of the invention may comprise an mRNA encoding a protein listed in Table 1 (or a homolog thereof, as discussed below) along with other components set out herein, and methods of the invention may comprise preparing and/or administering a composition comprising an mRNA encoding a protein listed in Table 1 (or a homolog thereof, as discussed below) along with other components set out herein.

TABLE 1

Secreted Proteins

| Uniprot ID | Protein Name | Gene Name |
| --- | --- | --- |
| A1E959 | Odontogenic ameloblast-associated protein | ODAM |
| A1KZ92 | Peroxidasin-like protein | PXDNL |
| A1L453 | Serine protease 38 | PRSS38 |
| A1L4H1 | Soluble scavenger receptor cysteine-rich domain-containing protein SSC5D | SSC5D |
| A2RUU4 | Colipase-like protein 1 | CLPSL1 |
| A2VDF0 | Fucose mutarotase | FUOM |
| A2VEC9 | SCO-spondin | SSPO |
| A3KMH1 | von Willebrand factor A domain-containing protein 8 | VWA8 |
| A4D0S4 | Laminin subunit beta-4 | LAMB4 |
| A4D1T9 | Probable inactive serine protease 37 | PRSS37 |
| A5D8T8 | C-type lectin domain family 18 member A | CLEC18A |
| A6NC86 | phospholipase A2 inhibitor and Ly6/PLAUR domain-containing protein | PINLYP |
| A6NCI4 | von Willebrand factor A domain-containing protein 3A | VWA3A |
| A6ND01 | Probable folate receptor delta | FOLR4 |
| A6NDD2 | Beta-defensin 108B-like | |
| A6NE02 | BTB/POZ domain-containing protein 17 | BTBD17 |
| A6NEF6 | Growth hormone 1 | GH1 |
| A6NF02 | NPIP-like protein LOC730153 | |
| A6NFB4 | HCG1749481, isoform CRA_k | CSH1 |
| A6NFZ4 | Protein FAM24A | FAM24A |
| A6NG13 | Glycosyltransferase 54 domain-containing protein | |
| A6NGN9 | IgLON family member 5 | IGLON5 |
| A6NHN0 | Otolin-1 | OTOL1 |
| A6NHN6 | Nuclear pore complex-interacting protein-like 2 | NPIPL2 |
| A6NI73 | Leukocyte immunoglobulin-like receptor subfamily A member 5 | LILRA5 |
| A6NIT4 | Chorionic somatomammotropin hormone 2 isoform 2 | CSH2 |
| A6NJ69 | IgA-inducing protein homolog | IGIP |
| A6NKQ9 | Choriogonadotropin subunit beta variant 1 | CGB1 |
| A6NMZ7 | Collagen alpha-6(VI) chain | COL6A6 |
| A6NNS2 | Dehydrogenase/reductase SDR family member 7C | DHRS7C |
| A6XGL2 | Insulin A chain | INS |
| A8K0G1 | Protein Wnt | WNT7B |
| A8K2U0 | Alpha-2-macroglobulin-like protein 1 | A2ML1 |
| A8K7I4 | Calcium-activated chloride channel regulator 1 | CLCA1 |
| A8MTL9 | Serpin-like protein HMSD | HMSD |
| A8MV23 | Serpin E3 | SERPINE3 |
| A8MZH6 | Oocyte-secreted protein 1 homolog | OOSP1 |
| A8TX70 | Collagen alpha-5(VI) chain | COL6A5 |
| B0ZBE8 | Natriuretic peptide | NPPA |
| B1A4G9 | Somatotropin | GH1 |
| B1A4H2 | HCG1749481, isoform CRA_d | CSH1 |
| B1A4H9 | Chorionic somatomammotropin hormone | CSH2 |
| B1AJZ6 | Protein Wnt | WNT4 |
| B1AKI9 | Isthmin-1 | ISM1 |
| B2RNN3 | Complement C1q and tumor necrosis factor-related protein 9B | C1QTNF9B |
| B2RUY7 | von Willebrand factor C domain-containing protein 2-like | VWC2L |
| B3GLJ2 | Prostate and testis expressed protein 3 | PATE3 |
| B4DI03 | SEC11-like 3 (S. cerevisiae), isoform CRA_a | SEC11L3 |
| B4DJF9 | Protein Wnt | WNT4 |
| B4DUL4 | SEC11-like 1 (S. cerevisiae), isoform CRA_d | SEC11L1 |
| B5MCC8 | Protein Wnt | WNT10B |
| B8A595 | Protein Wnt | WNT7B |
| B8A597 | Protein Wnt | WNT7B |
| B8A598 | Protein Wnt | WNT7B |
| B9A064 | Immunoglobulin lambda-like polypeptide 5 | IGLL5 |
| C9J3H3 | Protein Wnt | WNT10B |
| C9J8I8 | Protein Wnt | WNT5A |
| C9JAF2 | Insulin-like growth factor II Ala-25 Del | IGF2 |
| C9JCI2 | Protein Wnt | WNT10B |
| C9JL84 | HERV-H LTR-associating protein 1 | HHLA1 |
| C9JNR5 | Insulin A chain | INS |
| C9JUI2 | Protein Wnt | WNT2 |
| D6RF47 | Protein Wnt | WNT8A |

TABLE 1-continued

Secreted Proteins

| Uniprot ID | Protein Name | Gene Name |
| --- | --- | --- |
| D6RF94 | Protein Wnt | WNT8A |
| E2RYF7 | Protein PBMUCL2 | HCG22 |
| E5RFR1 | PENK(114-133) | PENK |
| E7EML9 | Serine protease 44 | PRSS44 |
| E7EPC3 | Protein Wnt | WNT9B |
| E7EVP0 | Nociceptin | PNOC |
| E9PD02 | Insulin-like growth factor I | IGF1 |
| E9PH60 | Protein Wnt | WNT16 |
| E9PJL6 | Protein Wnt | WNT11 |
| F5GYM2 | Protein Wnt | WNT5B |
| F5H034 | Protein Wnt | WNT5B |
| F5H364 | Protein Wnt | WNT5B |
| F5H7Q6 | Protein Wnt | WNT5B |
| F8WCM5 | Protein INS-IGF2 | INS-IGF2 |
| F8WDR1 | Protein Wnt | WNT2 |
| H0Y663 | Protein Wnt | WNT4 |
| H0YK72 | Signal peptidase complex catalytic subunit SEC11A | SEC11A |
| H0YK83 | Signal peptidase complex catalytic subunit SEC11A | SEC11A |
| H0YM39 | Chorionic somatomammotropin hormone | CSH2 |
| H0YMT7 | Chorionic somatomammotropin hormone | CSH1 |
| H0YN17 | Chorionic somatomammotropin hormone | CSH2 |
| H0YNA5 | Signal peptidase complex catalytic subunit SEC11A | SEC11A |
| H0YNG3 | Signal peptidase complex catalytic subunit SEC11A | SEC11A |
| H0YNX5 | Signal peptidase complex catalytic subunit SEC11A | SEC11A |
| H7BZB8 | Protein Wnt | WNT10A |
| H9KV56 | Choriogonadotropin subunit beta variant 2 | CGB2 |
| I3L0L8 | Protein Wnt | WNT9B |
| J3KNZ1 | Choriogonadotropin subunit beta variant 1 | CGB1 |
| J3KP00 | Choriogonadotropin subunit beta | CGB7 |
| J3QT02 | Choriogonadotropin subunit beta variant 1 | CGB1 |
| O00175 | C-C motif chemokine 24 | CCL24 |
| O00182 | Galectin-9 | LGALS9 |
| O00187 | Mannan-binding lectin serine protease 2 | MASP2 |
| O00230 | Cortistatin | CORT |
| O00253 | Agouti-related protein | AGRP |
| O00270 | 12-(S)-hydroxy-5,8,10,14-eicosatetraenoic acid receptor | GPR31 |
| O00292 | Left-right determination factor 2 | LEFTY2 |
| O00294 | Tubby-related protein 1 | TULP1 |
| O00295 | Tubby-related protein 2 | TULP2 |
| O00300 | Tumor necrosis factor receptor superfamily member 11B | TNFRSF11B |
| O00339 | Matrilin-2 | MATN2 |
| O00391 | Sulfhydryl oxidase 1 | QSOX1 |
| O00468 | Agrin | AGRN |
| O00515 | Ladinin-1 | LAD1 |
| O00533 | Processed neural cell adhesion molecule L1-like protein | CHL1 |
| O00584 | Ribonuclease T2 | RNASET2 |
| O00585 | C-C motif chemokine 21 | CCL21 |
| O00602 | Ficolin-1 | FCN1 |
| O00622 | Protein CYR61 | CYR61 |
| O00626 | MDC(5-69) | CCL22 |
| O00634 | Netrin-3 | NTN3 |
| O00744 | Protein Wnt-10b | WNT10B |
| O00755 | Protein Wnt-7a | WNT7A |
| O14498 | Immunoglobulin superfamily containing leucine-rich repeat protein | ISLR |
| O14511 | Pro-neuregulin-2, membrane-bound isoform | NRG2 |
| O14594 | Neurocan core protein | NCAN |
| O14625 | C-X-C motif chemokine 11 | CXCL11 |
| O14638 | Ectonucleotide pyrophosphatase/phosphodiesterase family member 3 | ENPP3 |
| O14656 | Torsin-1A | TOR1A |
| O14657 | Torsin-1B | TOR1B |
| O14786 | Neuropilin-1 | NRP1 |
| O14788 | Tumor necrosis factor ligand superfamily member 11, membrane form | TNFSF11 |
| O14791 | Apolipoprotein L1 | APOL1 |
| O14793 | Growth/differentiation factor 8 | MSTN |

TABLE 1-continued

Secreted Proteins

| Uniprot ID | Protein Name | Gene Name |
| --- | --- | --- |
| O14904 | Protein Wnt-9a | WNT9A |
| O14905 | Protein Wnt-9b | WNT9B |
| O14944 | Proepiregulin | EREG |
| O14960 | Leukocyte cell-derived chemotaxin-2 | LECT2 |
| O15018 | Processed PDZ domain-containing protein 2 | PDZD2 |
| O15041 | Semaphorin-3E | SEMA3E |
| O15072 | A disintegrin and metalloproteinase with thrombospondin motifs 3 | ADAMTS3 |
| O15123 | Angiopoietin-2 | ANGPT2 |
| O15130 | Neuropeptide FF | NPFF |
| O15197 | Ephrin type-B receptor 6 | EPHB6 |
| O15204 | ADAM DEC1 | ADAMDEC1 |
| O15230 | Laminin subunit alpha-5 | LAMA5 |
| O15232 | Matrilin-3 | MATN3 |
| O15240 | Neuroendocrine regulatory peptide-1 | VGF |
| O15263 | Beta-defensin 4A | DEFB4A |
| O15335 | Chondroadherin | CHAD |
| O15393 | Transmembrane protease serine 2 catalytic chain | TMPRSS2 |
| O15444 | C-C motif chemokine 25 | CCL25 |
| O15467 | C-C motif chemokine 16 | CCL16 |
| O15496 | Group 10 secretory phospholipase A2 | PLA2G10 |
| O15520 | Fibroblast growth factor 10 | FGF10 |
| O15537 | Retinoschisin | RS1 |
| O43157 | Plexin-B1 | PLXNB1 |
| O43184 | Disintegrin and metalloproteinase domain-containing protein 12 | ADAM12 |
| O43240 | Kallikrein-10 | KLK10 |
| O43278 | Kunitz-type protease inhibitor 1 | SPINT1 |
| O43320 | Fibroblast growth factor 16 | FGF16 |
| O43323 | Desert hedgehog protein C-product | DHH |
| O43405 | Cochlin | COCH |
| O43508 | Tumor necrosis factor ligand superfamily member 12, membrane form | TNFSF12 |
| O43555 | Progonadoliberin-2 | GNRH2 |
| O43557 | Tumor necrosis factor ligand superfamily member 14, soluble form | TNFSF14 |
| O43692 | Peptidase inhibitor 15 | PI15 |
| O43699 | Sialic acid-binding Ig-like lectin 6 | SIGLEC6 |
| O43820 | Hyaluronidase-3 | HYAL3 |
| O43827 | Angiopoietin-related protein 7 | ANGPTL7 |
| O43852 | Calumenin | CALU |
| O43854 | EGF-like repeat and discoidin I-like domain-containing protein 3 | EDIL3 |
| O43866 | CD5 antigen-like | CD5L |
| O43897 | Tolloid-like protein 1 | TLL1 |
| O43915 | Vascular endothelial growth factor D | FIGF |
| O43927 | C-X-C motif chemokine 13 | CXCL13 |
| O60218 | Aldo-keto reductase family 1 member B10 | AKR1B10 |
| O60235 | Transmembrane protease serine 11D | TMPRSS11D |
| O60258 | Fibroblast growth factor 17 | FGF17 |
| O60259 | Kallikrein-8 | KLK8 |
| O60383 | Growth/differentiation factor 9 | GDF9 |
| O60469 | Down syndrome cell adhesion molecule | DSCAM |
| O60542 | Persephin | PSPN |
| O60565 | Gremlin-1 | GREM1 |
| O60575 | Serine protease inhibitor Kazal-type 4 | SPINK4 |
| O60676 | Cystatin-8 | CST8 |
| O60687 | Sushi repeat-containing protein SRPX2 | SRPX2 |
| O60844 | Zymogen granule membrane protein 16 | ZG16 |
| O60882 | Matrix metalloproteinase-20 | MMP20 |
| O60938 | Keratocan | KERA |
| O75015 | Low affinity immunoglobulin gamma Fc region receptor III-B | FCGR3B |
| O75077 | Disintegrin and metalloproteinase domain-containing protein 23 | ADAM23 |
| O75093 | Slit homolog 1 protein | SLIT1 |
| O75094 | Slit homolog 3 protein | SLIT3 |
| O75095 | Multiple epidermal growth factor-like domains protein 6 | MEGF6 |
| O75173 | A disintegrin and metalloproteinase with thrombospondin motifs 4 | ADAMTS4 |
| O75200 | Nuclear pore complex-interacting protein-like 1 | NPIPL1 |
| O75339 | Cartilage intermediate layer protein 1 C1 | CILP |
| O75354 | Ectonucleoside triphosphate diphosphohydrolase 6 | ENTPD6 |
| O75386 | Tubby-related protein 3 | TULP3 |

TABLE 1-continued

Secreted Proteins

| Uniprot ID | Protein Name | Gene Name |
|---|---|---|
| O75398 | Deformed epidermal autoregulatory factor 1 homolog | DEAF1 |
| O75443 | Alpha-tectorin | TECTA |
| O75445 | Usherin | USH2A |
| O75462 | Cytokine receptor-like factor 1 | CRLF1 |
| O75487 | Glypican-4 | GPC4 |
| O75493 | Carbonic anhydrase-related protein 11 | CA11 |
| O75594 | Peptidoglycan recognition protein 1 | PGLYRP1 |
| O75596 | C-type lectin domain family 3 member A | CLEC3A |
| O75610 | Left-right determination factor 1 | LEFTY1 |
| O75629 | Protein CREG1 | CREG1 |
| O75636 | Ficolin-3 | FCN3 |
| O75711 | Scrapie-responsive protein 1 | SCRG1 |
| O75715 | Epididymal secretory glutathione peroxidase | GPX5 |
| O75718 | Cartilage-associated protein | CRTAP |
| O75829 | Chondrosurfactant protein | LECT1 |
| O75830 | Serpin I2 | SERPINI2 |
| O75882 | Attractin | ATRN |
| O75888 | Tumor necrosis factor ligand superfamily member 13 | TNFSF13 |
| O75900 | Matrix metalloproteinase-23 | MMP23A |
| O75951 | Lysozyme-like protein 6 | LYZL6 |
| O75973 | C1q-related factor | C1QL1 |
| O76038 | Secretagogin | SCGN |
| O76061 | Stanniocalcin-2 | STC2 |
| O76076 | WNT1-inducible-signaling pathway protein 2 | WISP2 |
| O76093 | Fibroblast growth factor 18 | FGF18 |
| O76096 | Cystatin-F | CST7 |
| O94769 | Extracellular matrix protein 2 | ECM2 |
| O94813 | Slit homolog 2 protein C-product | SLIT2 |
| O94907 | Dickkopf-related protein 1 | DKK1 |
| O94919 | Endonuclease domain-containing 1 protein | ENDOD1 |
| O94964 | N-terminal form | SOGA1 |
| O95025 | Semaphorin-3D | SEMA3D |
| O95084 | Serine protease 23 | PRSS23 |
| O95150 | Tumor necrosis factor ligand superfamily member 15 | TNFSF15 |
| O95156 | Neurexophilin-2 | NXPH2 |
| O95157 | Neurexophilin-3 | NXPH3 |
| O95158 | Neurexophilin-4 | NXPH4 |
| O95388 | WNT1-inducible-signaling pathway protein 1 | WISP1 |
| O95389 | WNT1-inducible-signaling pathway protein 3 | WISP3 |
| O95390 | Growth/differentiation factor 11 | GDF11 |
| O95393 | Bone morphogenetic protein 10 | BMP10 |
| O95399 | Urotensin-2 | UTS2 |
| O95407 | Tumor necrosis factor receptor superfamily member 6B | TNFRSF6B |
| O95428 | Papilin | PAPLN |
| O95445 | Apolipoprotein M | APOM |
| O95450 | A disintegrin and metalloproteinase with thrombospondin motifs 2 | ADAMTS2 |
| O95460 | Matrilin-4 | MATN4 |
| O95467 | LHAL tetrapeptide | GNAS |
| O95631 | Netrin-1 | NTN1 |
| O95633 | Follistatin-related protein 3 | FSTL3 |
| O95711 | Lymphocyte antigen 86 | LY86 |
| O95715 | C-X-C motif chemokine 14 | CXCL14 |
| O95750 | Fibroblast growth factor 19 | FGF19 |
| O95760 | Interleukin-33 | IL33 |
| O95813 | Cerberus | CER1 |
| O95841 | Angiopoietin-related protein 1 | ANGPTL1 |
| O95897 | Noelin-2 | OLFM2 |
| O95925 | Eppin | EPPIN |
| O95965 | Integrin beta-like protein 1 | ITGBL1 |
| O95967 | EGF-containing fibulin-like extracellular matrix protein 2 | EFEMP2 |
| O95968 | Secretoglobin family 1D member 1 | SCGB1D1 |
| O95969 | Secretoglobin family 1D member 2 | SCGB1D2 |
| O95970 | Leucine-rich glioma-inactivated protein 1 | LGI1 |
| O95972 | Bone morphogenetic protein 15 | BMP15 |
| O95994 | Anterior gradient protein 2 homolog | AGR2 |
| O95998 | Interleukin-18-binding protein | IL18BP |
| O96009 | Napsin-A | NAPSA |
| O96014 | Protein Wnt-11 | WNT11 |
| P00450 | Ceruloplasmin | CP |
| P00451 | Factor VIIIa light chain | F8 |

TABLE 1-continued

Secreted Proteins

| Uniprot ID | Protein Name | Gene Name |
|---|---|---|
| P00488 | Coagulation factor XIII A chain | F13A1 |
| P00533 | Epidermal growth factor receptor | EGFR |
| P00709 | Alpha-lactalbumin | LALBA |
| P00734 | Prothrombin | F2 |
| P00738 | Haptoglobin beta chain | HP |
| P00739 | Haptoglobin-related protein | HPR |
| P00740 | Coagulation factor IXa heavy chain | F9 |
| P00742 | Factor X heavy chain | F10 |
| P00746 | Complement factor D | CFD |
| P00747 | Plasmin light chain B | PLG |
| P00748 | Coagulation factor XIIa light chain | F12 |
| P00749 | Urokinase-type plasminogen activator long chain A | PLAU |
| P00750 | Tissue-type plasminogen activator | PLAT |
| P00751 | Complement factor B Ba fragment | CFB |
| P00797 | Renin | REN |
| P00973 | 2'-5'-oligoadenylate synthase 1 | OAS1 |
| P00995 | Pancreatic secretory trypsin inhibitor | SPINK1 |
| P01008 | Antithrombin-III | SERPINC1 |
| P01009 | Alpha-1-antitrypsin | SERPINA1 |
| P01011 | Alpha-1-antichymotrypsin His-Pro-less | SERPINA3 |
| P01019 | Angiotensin-1 | AGT |
| P01023 | Alpha-2-macroglobulin | A2M |
| P01024 | Acylation stimulating protein | C3 |
| P01031 | Complement C5 beta chain | C5 |
| P01033 | Metalloproteinase inhibitor 1 | TIMP1 |
| P01034 | Cystatin-C | CST3 |
| P01036 | Cystatin-S | CST4 |
| P01037 | Cystatin-SN | CST1 |
| P01042 | Kininogen-1 light chain | KNG1 |
| P01127 | Platelet-derived growth factor subunit B | PDGFB |
| P01135 | Transforming growth factor alpha | TGFA |
| P01137 | Transforming growth factor beta-1 | TGFB1 |
| P01138 | Beta-nerve growth factor | NGF |
| P01148 | Gonadoliberin-1 | GNRH1 |
| P01160 | Atrial natriuretic factor | NPPA |
| P01178 | Oxytocin | OXT |
| P01185 | Vasopressin-neurophysin 2-copeptin | AVP |
| P01189 | Corticotropin | POMC |
| P01210 | PENK(237-258) | PENK |
| P01213 | Alpha-neoendorphin | PDYN |
| P01215 | Glycoprotein hormones alpha chain | CGA |
| P01222 | Thyrotropin subunit beta | TSHB |
| P01225 | Follitropin subunit beta | FSHB |
| P01229 | Lutropin subunit beta | LHB |
| P01233 | Choriogonadotropin subunit beta | CGB8 |
| P01236 | Prolactin | PRL |
| P01241 | Somatotropin | GH1 |
| P01242 | Growth hormone variant | GH2 |
| P01243 | Chorionic somatomammotropin hormone | CSH2 |
| P01258 | Katacalcin | CALCA |
| P01266 | Thyroglobulin | TG |
| P01270 | Parathyroid hormone | PTH |
| P01275 | Glucagon | GCG |
| P01282 | Intestinal peptide PHM-27 | VIP |
| P01286 | Somatoliberin | GHRH |
| P01298 | Pancreatic prohormone | PPY |
| P01303 | C-flanking peptide of NPY | NPY |
| P01308 | Insulin | INS |
| P01344 | Insulin-like growth factor II | IGF2 |
| P01350 | Big gastrin | GAST |
| P01374 | Lymphotoxin-alpha | LTA |
| P01375 | C-domain 1 | TNF |
| P01562 | Interferon alpha-1/13 | IFNA1 |
| P01563 | Interferon alpha-2 | IFNA2 |
| P01566 | Interferon alpha-10 | IFNA10 |
| P01567 | Interferon alpha-7 | IFNA7 |
| P01568 | Interferon alpha-21 | IFNA21 |
| P01569 | Interferon alpha-5 | IFNA5 |
| P01570 | Interferon alpha-14 | IFNA14 |
| P01571 | Interferon alpha-17 | IFNA17 |
| P01574 | Interferon beta | IFNB1 |
| P01579 | Interferon gamma | IFNG |
| P01583 | Interleukin-1 alpha | IL1A |
| P01584 | Interleukin-1 beta | IL1B |
| P01588 | Erythropoietin | EPO |

TABLE 1-continued

Secreted Proteins

| Uniprot ID | Protein Name | Gene Name |
|---|---|---|
| P01591 | Immunoglobulin J chain | IGJ |
| P01732 | T-cell surface glycoprotein CD8 alpha chain | CD8A |
| P01833 | Polymeric immunoglobulin receptor | PIGR |
| P01857 | Ig gamma-1 chain C region | IGHG1 |
| P01859 | Ig gamma-2 chain C region | IGHG2 |
| P01860 | Ig gamma-3 chain C region | IGHG3 |
| P01861 | Ig gamma-4 chain C region | IGHG4 |
| P01871 | Ig mu chain C region | IGHM |
| P01880 | Ig delta chain C region | IGHD |
| P02452 | Collagen alpha-1(I) chain | COL1A1 |
| P02458 | Chondrocalcin | COL2A1 |
| P02461 | Collagen alpha-1(III) chain | COL3A1 |
| P02462 | Collagen alpha-1(IV) chain | COL4A1 |
| P02647 | Apolipoprotein A-I | APOA1 |
| P02649 | Apolipoprotein E | APOE |
| P02652 | Apolipoprotein A-II | APOA2 |
| P02654 | Apolipoprotein C-I | APOC1 |
| P02655 | Apolipoprotein C-II | APOC2 |
| P02656 | Apolipoprotein C-III | APOC3 |
| P02671 | Fibrinogen alpha chain | FGA |
| P02675 | Fibrinopeptide B | FGB |
| P02679 | Fibrinogen gamma chain | FGG |
| P02741 | C-reactive protein | CRP |
| P02743 | Serum amyloid P-component(1-203) | APCS |
| P02745 | Complement C1q subcomponent subunit A | C1QA |
| P02746 | Complement C1q subcomponent subunit B | C1QB |
| P02747 | Complement C1q subcomponent subunit C | C1QC |
| P02748 | Complement component C9b | C9 |
| P02749 | Beta-2-glycoprotein 1 | APOH |
| P02750 | Leucine-rich alpha-2-glycoprotein | LRG1 |
| P02751 | Ugl-Y2 | FN1 |
| P02753 | Retinol-binding protein 4 | RBP4 |
| P02760 | Trypstatin | AMBP |
| P02763 | Alpha-1-acid glycoprotein 1 | ORM1 |
| P02765 | Alpha-2-HS-glycoprotein chain A | AHSG |
| P02766 | Transthyretin | TTR |
| P02768 | Serum albumin | ALB |
| P02771 | Alpha-fetoprotein | AFP |
| P02774 | Vitamin D-binding protein | GC |
| P02775 | Connective tissue-activating peptide III | PPBP |
| P02776 | Platelet factor 4 | PF4 |
| P02778 | CXCL10(1-73) | CXCL10 |
| P02786 | Transferrin receptor protein 1 | TFRC |
| P02787 | Serotransferrin | TF |
| P02788 | Lactoferroxin-C | LTF |
| P02790 | Hemopexin | HPX |
| P02808 | Statherin | STATH |
| P02810 | Salivary acidic proline-rich phosphoprotein 1/2 | PRH2 |
| P02812 | Basic salivary proline-rich protein 2 | PRB2 |
| P02814 | Peptide D1A | SMR3B |
| P02818 | Osteocalcin | BGLAP |
| P03950 | Angiogenin | ANG |
| P03951 | Coagulation factor XIa heavy chain | F11 |
| P03952 | Plasma kallikrein | KLKB1 |
| P03956 | 27 kDa interstitial collagenase | MMP1 |
| P03971 | Muellerian-inhibiting factor | AMH |
| P03973 | Antileukoproteinase | SLPI |
| P04003 | C4b-binding protein alpha chain | C4BPA |
| P04004 | Somatomedin-B | VTN |
| P04054 | Phospholipase A2 | PLA2G1B |
| P04085 | Platelet-derived growth factor subunit A | PDGFA |
| P04090 | Relaxin A chain | RLN2 |
| P04114 | Apolipoprotein B-100 | APOB |
| P04118 | Colipase | CLPS |
| P04141 | Granulocyte-macrophage colony-stimulating factor | CSF2 |
| P04155 | Trefoil factor 1 | TFF1 |
| P04180 | Phosphatidylcholine-sterol acyltransferase | LCAT |
| P04196 | Histidine-rich glycoprotein | HRG |
| P04217 | Alpha-1B-glycoprotein | A1BG |
| P04275 | von Willebrand antigen 2 | VWF |
| P04278 | Sex hormone-binding globulin | SHBG |
| P04279 | Alpha-inhibin-31 | SEMG1 |
| P04280 | Basic salivary proline-rich protein 1 | PRB1 |
| P04628 | Proto-oncogene Wnt-1 | WNT1 |
| P04745 | Alpha-amylase 1 | AMY1A |

TABLE 1-continued

Secreted Proteins

| Uniprot ID | Protein Name | Gene Name |
| --- | --- | --- |
| P04746 | Pancreatic alpha-amylase | AMY2A |
| P04808 | Prorelaxin H1 | RLN1 |
| P05000 | Interferon omega-1 | IFNW1 |
| P05013 | Interferon alpha-6 | IFNA6 |
| P05014 | Interferon alpha-4 | IFNA4 |
| P05015 | Interferon alpha-16 | IFNA16 |
| P05019 | Insulin-like growth factor I | IGF1 |
| P05060 | GAWK peptide | CHGB |
| P05090 | Apolipoprotein D | APOD |
| P05109 | Protein S100-A8 | S100A8 |
| P05111 | Inhibin alpha chain | INHA |
| P05112 | Interleukin-4 | IL4 |
| P05113 | Interleukin-5 | IL5 |
| P05120 | Plasminogen activator inhibitor 2 | SERPINB2 |
| P05121 | Plasminogen activator inhibitor 1 | SERPINE1 |
| P05154 | Plasma serine protease inhibitor | SERPINA5 |
| P05155 | Plasma protease C1 inhibitor | SERPING1 |
| P05156 | Complement factor I heavy chain | CFI |
| P05160 | Coagulation factor XIII B chain | F13B |
| P05161 | Ubiquitin-like protein ISG15 | ISG15 |
| P05230 | Fibroblast growth factor 1 | FGF1 |
| P05231 | Interleukin-6 | IL6 |
| P05305 | Big endothelin-1 | EDN1 |
| P05408 | C-terminal peptide | SCG5 |
| P05451 | Lithostathine-1-alpha | REG1A |
| P05452 | Tetranectin | CLEC3B |
| P05543 | Thyroxine-binding globulin | SERPINA7 |
| P05814 | Beta-casein | CSN2 |
| P05997 | Collagen alpha-2(V) chain | COL5A2 |
| P06276 | Cholinesterase | BCHE |
| P06307 | Cholecystokinin-12 | CCK |
| P06396 | Gelsolin | GSN |
| P06681 | Complement C2 | C2 |
| P06702 | Protein S100-A9 | S100A9 |
| P06727 | Apolipoprotein A-IV | APOA4 |
| P06734 | Low affinity immunoglobulin epsilon Fc receptor soluble form | FCER2 |
| P06744 | Glucose-6-phosphate isomerase | GPI |
| P06850 | Corticoliberin | CRH |
| P06858 | Lipoprotein lipase | LPL |
| P06881 | Calcitonin gene-related peptide 1 | CALCA |
| P07093 | Glia-derived nexin | SERPINE2 |
| P07098 | Gastric triacylglycerol lipase | LIPF |
| P07225 | Vitamin K-dependent protein S | PROS1 |
| P07237 | Protein disulfide-isomerase | P4HB |
| P07288 | Prostate-specific antigen | KLK3 |
| P07306 | Asialoglycoprotein receptor 1 | ASGR1 |
| P07355 | Annexin A2 | ANXA2 |
| P07357 | Complement component C8 alpha chain | C8A |
| P07358 | Complement component C8 beta chain | C8B |
| P07360 | Complement component C8 gamma chain | C8G |
| P07477 | Alpha-trypsin chain 2 | PRSS1 |
| P07478 | Trypsin-2 | PRSS2 |
| P07492 | Neuromedin-C | GRP |
| P07498 | Kappa-casein | CSN3 |
| P07585 | Decorin | DCN |
| P07911 | Uromodulin | UMOD |
| P07942 | Laminin subunit beta-1 | LAMB1 |
| P07988 | Pulmonary surfactant-associated protein B | SFTPB |
| P07998 | Ribonuclease pancreatic | RNASE1 |
| P08118 | Beta-microseminoprotein | MSMB |
| P08123 | Collagen alpha-2(I) chain | COL1A2 |
| P08185 | Corticosteroid-binding globulin | SERPINA6 |
| P08217 | Chymotrypsin-like elastase family member 2A | CELA2A |
| P08218 | Chymotrypsin-like elastase family member 2B | CELA2B |
| P08253 | 72 kDa type IV collagenase | MMP2 |
| P08254 | Stromelysin-1 | MMP3 |
| P08294 | Extracellular superoxide dismutase [Cu—Zn] | SOD3 |
| P08476 | Inhibin beta A chain | INHBA |
| P08493 | Matrix Gla protein | MGP |
| P08572 | Collagen alpha-2(IV) chain | COL4A2 |
| P08581 | Hepatocyte growth factor receptor | MET |
| P08603 | Complement factor H | CFH |
| P08620 | Fibroblast growth factor 4 | FGF4 |
| P08637 | Low affinity immunoglobulin gamma Fc region receptor III-A | FCGR3A |

TABLE 1-continued

Secreted Proteins

| Uniprot ID | Protein Name | Gene Name |
| --- | --- | --- |
| P08697 | Alpha-2-antiplasmin | SERPINF2 |
| P08700 | Interleukin-3 | IL3 |
| P08709 | Coagulation factor VII | F7 |
| P08833 | Insulin-like growth factor-binding protein 1 | IGFBP1 |
| P08887 | Interleukin-6 receptor subunit alpha | IL6R |
| P08949 | Neuromedin-B-32 | NMB |
| P08F94 | Fibrocystin | PKHD1 |
| P09038 | Fibroblast growth factor 2 | FGF2 |
| P09228 | Cystatin-SA | CST2 |
| P09237 | Matrilysin | MMP7 |
| P09238 | Stromelysin-2 | MMP10 |
| P09341 | Growth-regulated alpha protein | CXCL1 |
| P09382 | Galectin-1 | LGALS1 |
| P09466 | Glycodelin | PAEP |
| P09486 | SPARC | SPARC |
| P09529 | Inhibin beta B chain | INHBB |
| P09544 | Protein Wnt-2 | WNT2 |
| P09603 | Processed macrophage colony-stimulating factor 1 | CSF1 |
| P09681 | Gastric inhibitory polypeptide | GIP |
| P09683 | Secretin | SCT |
| P09919 | Granulocyte colony-stimulating factor | CSF3 |
| P0C091 | FRAS1-related extracellular matrix protein 3 | FREM3 |
| P0C0L4 | C4d-A | C4A |
| P0C0L5 | Complement C4-B alpha chain | C4B |
| P0C0P6 | Neuropeptide S | NPS |
| P0C7L1 | Serine protease inhibitor Kazal-type 8 | SPINK8 |
| P0C862 | Complement C1q and tumor necrosis factor-related protein 9A | C1QTNF9 |
| P0C8F1 | Prostate and testis expressed protein 4 | PATE4 |
| P0CG01 | Gastrokine-3 | GKN3P |
| P0CG36 | Cryptic family protein 1B | CFC1B |
| P0CG37 | Cryptic protein | CFC1 |
| P0CJ68 | Humanin-like protein 1 | MTRNR2L1 |
| P0CJ69 | Humanin-like protein 2 | MTRNR2L2 |
| P0CJ70 | Humanin-like protein 3 | MTRNR2L3 |
| P0CJ71 | Humanin-like protein 4 | MTRNR2L4 |
| P0CJ72 | Humanin-like protein 5 | MTRNR2L5 |
| P0CJ73 | Humanin-like protein 6 | MTRNR2L6 |
| P0CJ74 | Humanin-like protein 7 | MTRNR2L7 |
| P0CJ75 | Humanin-like protein 8 | MTRNR2L8 |
| P0CJ76 | Humanin-like protein 9 | MTRNR2L9 |
| P0CJ77 | Humanin-like protein 10 | MTRNR2L10 |
| P0DJD7 | Pepsin A-4 | PGA4 |
| P0DJD8 | Pepsin A-3 | PGA3 |
| P0DJD9 | Pepsin A-5 | PGA5 |
| P0DJI8 | Amyloid protein A | SAA1 |
| P0DJI9 | Serum amyloid A-2 protein | SAA2 |
| P10082 | Peptide YY(3-36) | PYY |
| P10092 | Calcitonin gene-related peptide 2 | CALCB |
| P10124 | Serglycin | SRGN |
| P10145 | MDNCF-a | IL8 |
| P10147 | MIP-1-alpha(4-69) | CCL3 |
| P10163 | Peptide P-D | PRB4 |
| P10451 | Osteopontin | SPP1 |
| P10599 | Thioredoxin | TXN |
| P10600 | Transforming growth factor beta-3 | TGFB3 |
| P10643 | Complement component C7 | C7 |
| P10645 | Vasostatin-2 | CHGA |
| P10646 | Tissue factor pathway inhibitor | TFPI |
| P10720 | Platelet factor 4 variant(4-74) | PF4V1 |
| P10745 | Retinol-binding protein 3 | RBP3 |
| P10767 | Fibroblast growth factor 6 | FGF6 |
| P10909 | Clusterin alpha chain | CLU |
| P10912 | Growth hormone receptor | GHR |
| P10915 | Hyaluronan and proteoglycan link protein 1 | HAPLN1 |
| P10966 | T-cell surface glycoprotein CD8 beta chain | CD8B |
| P10997 | Islet amyloid polypeptide | IAPP |
| P11047 | Laminin subunit gamma-1 | LAMC1 |
| P11150 | Hepatic triacylglycerol lipase | LIPC |
| P11226 | Mannose-binding protein C | MBL2 |
| P11464 | Pregnancy-specific beta-1-glycoprotein 1 | PSG1 |
| P11465 | Pregnancy-specific beta-1-glycoprotein 2 | PSG2 |
| P11487 | Fibroblast growth factor 3 | FGF3 |
| P11597 | Cholesteryl ester transfer protein | CETP |
| P11684 | Uteroglobin | SCGB1A1 |
| P11686 | Pulmonary surfactant-associated protein C | SFTPC |

TABLE 1-continued

Secreted Proteins

| Uniprot ID | Protein Name | Gene Name |
|---|---|---|
| P12034 | Fibroblast growth factor 5 | FGF5 |
| P12107 | Collagen alpha-1(XI) chain | COL11A1 |
| P12109 | Collagen alpha-1(VI) chain | COL6A1 |
| P12110 | Collagen alpha-2(VI) chain | COL6A2 |
| P12111 | Collagen alpha-3(VI) chain | COL6A3 |
| P12259 | Coagulation factor V | F5 |
| P12272 | PTHrP[1-36] | PTHLH |
| P12273 | Prolactin-inducible protein | PIP |
| P12544 | Granzyme A | GZMA |
| P12643 | Bone morphogenetic protein 2 | BMP2 |
| P12644 | Bone morphogenetic protein 4 | BMP4 |
| P12645 | Bone morphogenetic protein 3 | BMP3 |
| P12724 | Eosinophil cationic protein | RNASE3 |
| P12821 | Angiotensin-converting enzyme, soluble form | ACE |
| P12838 | Neutrophil defensin 4 | DEFA4 |
| P12872 | Motilin | MLN |
| P13232 | Interleukin-7 | IL7 |
| P13236 | C-C motif chemokine 4 | CCL4 |
| P13284 | Gamma-interferon-inducible lysosomal thiol reductase | IFI30 |
| P13500 | C-C motif chemokine 2 | CCL2 |
| P13501 | C-C motif chemokine 5 | CCL5 |
| P13521 | Secretogranin-2 | SCG2 |
| P13591 | Neural cell adhesion molecule 1 | NCAM1 |
| P13611 | Versican core protein | VCAN |
| P13671 | Complement component C6 | C6 |
| P13688 | Carcinoembryonic antigen-related cell adhesion molecule 1 | CEACAM1 |
| P13725 | Oncostatin-M | OSM |
| P13726 | Tissue factor | F3 |
| P13727 | Eosinophil granule major basic protein | PRG2 |
| P13942 | Collagen alpha-2(XI) chain | COL11A2 |
| P13987 | CD59 glycoprotein | CD59 |
| P14138 | Endothelin-3 | EDN3 |
| P14174 | Macrophage migration inhibitory factor | MIF |
| P14207 | Folate receptor beta | FOLR2 |
| P14222 | Perforin-1 | PRF1 |
| P14543 | Nidogen-1 | NID1 |
| P14555 | Phospholipase A2, membrane associated | PLA2G2A |
| P14625 | Endoplasmin | HSP90B1 |
| P14735 | Insulin-degrading enzyme | IDE |
| P14778 | Interleukin-1 receptor type 1, soluble form | IL1R1 |
| P14780 | 82 kDa matrix metalloproteinase-9 | MMP9 |
| P15018 | Leukemia inhibitory factor | LIF |
| P15085 | Carboxypeptidase A1 | CPA1 |
| P15086 | Carboxypeptidase B | CPB1 |
| P15151 | Poliovirus receptor | PVR |
| P15169 | Carboxypeptidase N catalytic chain | CPN1 |
| P15248 | Interleukin-9 | IL9 |
| P15291 | N-acetyllactosamine synthase | B4GALT1 |
| P15309 | PAPf39 | ACPP |
| P15328 | Folate receptor alpha | FOLR1 |
| P15374 | Ubiquitin carboxyl-terminal hydrolase isozyme L3 | UCHL3 |
| P15502 | Elastin | ELN |
| P15509 | Granulocyte-macrophage colony-stimulating factor receptor subunit alpha | CSF2RA |
| P15515 | Histatin-1 | HTN1 |
| P15516 | His3-(31-51)-peptide | HTN3 |
| P15692 | Vascular endothelial growth factor A | VEGFA |
| P15814 | Immunoglobulin lambda-like polypeptide 1 | IGLL1 |
| P15907 | Beta-galactoside alpha-2,6-sialyltransferase 1 | ST6GAL1 |
| P15941 | Mucin-1 subunit beta | MUC1 |
| P16035 | Metalloproteinase inhibitor 2 | TIMP2 |
| P16112 | Aggrecan core protein 2 | ACAN |
| P16233 | Pancreatic triacylglycerol lipase | PNLIP |
| P16442 | Histo-blood group ABO system transferase | ABO |
| P16471 | Prolactin receptor | PRLR |
| P16562 | Cysteine-rich secretory protein 2 | CRISP2 |
| P16619 | C-C motif chemokine 3-like 1 | CCL3L1 |
| P16860 | BNP(3-29) | NPPB |
| P16870 | Carboxypeptidase E | CPE |
| P16871 | Interleukin-7 receptor subunit alpha | IL7R |
| P17213 | Bactericidal permeability-increasing protein | BPI |
| P17538 | Chymotrypsinogen B | CTRB1 |
| P17931 | Galectin-3 | LGALS3 |
| P17936 | Insulin-like growth factor-binding protein 3 | IGFBP3 |

TABLE 1-continued

Secreted Proteins

| Uniprot ID | Protein Name | Gene Name |
|---|---|---|
| P17948 | Vascular endothelial growth factor receptor 1 | FLT1 |
| P18065 | Insulin-like growth factor-binding protein 2 | IGFBP2 |
| P18075 | Bone morphogenetic protein 7 | BMP7 |
| P18428 | Lipopolysaccharide-binding protein | LBP |
| P18509 | PACAP-related peptide | ADCYAP1 |
| P18510 | Interleukin-1 receptor antagonist protein | IL1RN |
| P18827 | Syndecan-1 | SDC1 |
| P19021 | Peptidylglycine alpha-hydroxylating monooxygenase | PAM |
| P19235 | Erythropoietin receptor | EPOR |
| P19438 | Tumor necrosis factor-binding protein 1 | TNFRSF1A |
| P19652 | Alpha-1-acid glycoprotein 2 | ORM2 |
| P19801 | Amiloride-sensitive amine oxidase [copper-containing] | ABP1 |
| P19823 | Inter-alpha-trypsin inhibitor heavy chain H2 | ITIH2 |
| P19827 | Inter-alpha-trypsin inhibitor heavy chain H1 | ITIH1 |
| P19835 | Bile salt-activated lipase | CEL |
| P19875 | C-X-C motif chemokine 2 | CXCL2 |
| P19876 | C-X-C motif chemokine 3 | CXCL3 |
| P19883 | Follistatin | FST |
| P19957 | Elafin | PI3 |
| P19961 | Alpha-amylase 2B | AMY2B |
| P20061 | Transcobalamin-1 | TCN1 |
| P20062 | Transcobalamin-2 | TCN2 |
| P20142 | Gastricsin | PGC |
| P20155 | Serine protease inhibitor Kazal-type 2 | SPINK2 |
| P20231 | Tryptase beta-2 | TPSB2 |
| P20333 | Tumor necrosis factor receptor superfamily member 1B | TNFRSF1B |
| P20366 | Substance P | TAC1 |
| P20382 | Melanin-concentrating hormone | PMCH |
| P20396 | Thyroliberin | TRH |
| P20742 | Pregnancy zone protein | PZP |
| P20774 | Mimecan | OGN |
| P20783 | Neurotrophin-3 | NTF3 |
| P20800 | Endothelin-2 | EDN2 |
| P20809 | Interleukin-11 | IL11 |
| P20827 | Ephrin-A1 | EFNA1 |
| P20849 | Collagen alpha-1(IX) chain | COL9A1 |
| P20851 | C4b-binding protein beta chain | C4BPB |
| P20908 | Collagen alpha-1(V) chain | COL5A1 |
| P21128 | Poly(U)-specific endoribonuclease | ENDOU |
| P21246 | Pleiotrophin | PTN |
| P21583 | Kit ligand | KITLG |
| P21741 | Midkine | MDK |
| P21754 | Zona pellucida sperm-binding protein 3 | ZP3 |
| P21781 | Fibroblast growth factor 7 | FGF7 |
| P21802 | Fibroblast growth factor receptor 2 | FGFR2 |
| P21810 | Biglycan | BGN |
| P21815 | Bone sialoprotein 2 | IBSP |
| P21860 | Receptor tyrosine-protein kinase erbB-3 | ERBB3 |
| P21941 | Cartilage matrix protein | MATN1 |
| P22003 | Bone morphogenetic protein 5 | BMP5 |
| P22004 | Bone morphogenetic protein 6 | BMP6 |
| P22079 | Lactoperoxidase | LPO |
| P22105 | Tenascin-X | TNXB |
| P22301 | Interleukin-10 | IL10 |
| P22303 | Acetylcholinesterase | ACHE |
| P22352 | Glutathione peroxidase 3 | GPX3 |
| P22362 | C-C motif chemokine 1 | CCL1 |
| P22455 | Fibroblast growth factor receptor 4 | FGFR4 |
| P22466 | Galanin message-associated peptide | GAL |
| P22692 | Insulin-like growth factor-binding protein 4 | IGFBP4 |
| P22749 | Granulysin | GNLY |
| P22792 | Carboxypeptidase N subunit 2 | CPN2 |
| P22891 | Vitamin K-dependent protein Z | PROZ |
| P22894 | Neutrophil collagenase | MMP8 |
| P23142 | Fibulin-1 | FBLN1 |
| P23280 | Carbonic anhydrase 6 | CA6 |
| P23352 | Anosmin-1 | KAL1 |
| P23435 | Cerebellin-1 | CBLN1 |
| P23560 | Brain-derived neurotrophic factor | BDNF |
| P23582 | C-type natriuretic peptide | NPPC |
| P23946 | Chymase | CMA1 |
| P24043 | Laminin subunit alpha-2 | LAMA2 |
| P24071 | Immunoglobulin alpha Fc receptor | FCAR |

TABLE 1-continued

Secreted Proteins

| Uniprot ID | Protein Name | Gene Name |
|---|---|---|
| P24347 | Stromelysin-3 | MMP11 |
| P24387 | Corticotropin-releasing factor-binding protein | CRHBP |
| P24592 | Insulin-like growth factor-binding protein 6 | IGFBP6 |
| P24593 | Insulin-like growth factor-binding protein 5 | IGFBP5 |
| P24821 | Tenascin | TNC |
| P24855 | Deoxyribonuclease-1 | DNASE1 |
| P25067 | Collagen alpha-2(VIII) chain | COL8A2 |
| P25311 | Zinc-alpha-2-glycoprotein | AZGP1 |
| P25391 | Laminin subunit alpha-1 | LAMA1 |
| P25445 | Tumor necrosis factor receptor superfamily member 6 | FAS |
| P25940 | Collagen alpha-3(V) chain | COL5A3 |
| P25942 | Tumor necrosis factor receptor superfamily member 5 | CD40 |
| P26022 | Pentraxin-related protein PTX3 | PTX3 |
| P26927 | Hepatocyte growth factor-like protein beta chain | MST1 |
| P27169 | Serum paraoxonase/arylesterase 1 | PON1 |
| P27352 | Gastric intrinsic factor | GIF |
| P27487 | Dipeptidyl peptidase 4 membrane form | DPP4 |
| P27539 | Embryonic growth/differentiation factor 1 | GDF1 |
| P27658 | Vastatin | COL8A1 |
| P27797 | Calreticulin | CALR |
| P27918 | Properdin | CFP |
| P28039 | Acyloxyacyl hydrolase | AOAH |
| P28300 | Protein-lysine 6-oxidase | LOX |
| P28325 | Cystatin-D | CST5 |
| P28799 | Granulin-1 | GRN |
| P29122 | Proprotein convertase subtilisin/kexin type 6 | PCSK6 |
| P29279 | Connective tissue growth factor | CTGF |
| P29320 | Ephrin type-A receptor 3 | EPHA3 |
| P29400 | Collagen alpha-5(IV) chain | COL4A5 |
| P29459 | Interleukin-12 subunit alpha | IL12A |
| P29460 | Interleukin-12 subunit beta | IL12B |
| P29508 | Serpin B3 | SERPINB3 |
| P29622 | Kallistatin | SERPINA4 |
| P29965 | CD40 ligand, soluble form | CD40LG |
| P30990 | Neurotensin/neuromedin N | NTS |
| P31025 | Lipocalin-1 | LCN1 |
| P31151 | Protein S100-A7 | S100A7 |
| P31371 | Fibroblast growth factor 9 | FGF9 |
| P31431 | Syndecan-4 | SDC4 |
| P31947 | 14-3-3 protein sigma | SFN |
| P32455 | Interferon-induced guanylate-binding protein 1 | GBP1 |
| P32881 | Interferon alpha-8 | IFNA8 |
| P34096 | Ribonuclease 4 | RNASE4 |
| P34130 | Neurotrophin-4 | NTF4 |
| P34820 | Bone morphogenetic protein 8B | BMP8B |
| P35030 | Trypsin-3 | PRSS3 |
| P35052 | Secreted glypican-1 | GPC1 |
| P35070 | Betacellulin | BTC |
| P35225 | Interleukin-13 | IL13 |
| P35247 | Pulmonary surfactant-associated protein D | SFTPD |
| P35318 | ADM | ADM |
| P35542 | Serum amyloid A-4 protein | SAA4 |
| P35555 | Fibrillin-1 | FBN1 |
| P35556 | Fibrillin-2 | FBN2 |
| P35625 | Metalloproteinase inhibitor 3 | TIMP3 |
| P35858 | Insulin-like growth factor-binding protein complex acid labile subunit | IGFALS |
| P35916 | Vascular endothelial growth factor receptor 3 | FLT4 |
| P35968 | Vascular endothelial growth factor receptor 2 | KDR |
| P36222 | Chitinase-3-like protein 1 | CHI3L1 |
| P36952 | Serpin B5 | SERPINB5 |
| P36955 | Pigment epithelium-derived factor | SERPINF1 |
| P36980 | Complement factor H-related protein 2 | CFHR2 |
| P39059 | Collagen alpha-1(XV) chain | COL15A1 |
| P39060 | Collagen alpha-1(XVIII) chain | COL18A1 |
| P39877 | Calcium-dependent phospholipase A2 | PLA2G5 |
| P39900 | Macrophage metalloelastase | MMP12 |
| P39905 | Glial cell line-derived neurotrophic factor | GDNF |
| P40225 | Thrombopoietin | THPO |
| P40967 | M-alpha | PMEL |
| P41159 | Leptin | LEP |
| P41221 | Protein Wnt-5a | WNT5A |
| P41222 | Prostaglandin-H2 D-isomerase | PTGDS |
| P41271 | Neuroblastoma suppressor of tumorigenicity 1 | NBL1 |

TABLE 1-continued

Secreted Proteins

| Uniprot ID | Protein Name | Gene Name |
|---|---|---|
| P41439 | Folate receptor gamma | FOLR3 |
| P42127 | Agouti-signaling protein | ASIP |
| P42702 | Leukemia inhibitory factor receptor | LIFR |
| P42830 | ENA-78(9-78) | CXCL5 |
| P43026 | Growth/differentiation factor 5 | GDF5 |
| P43251 | Biotinidase | BTD |
| P43652 | Afamin | AFM |
| P45452 | Collagenase 3 | MMP13 |
| P47710 | Casoxin-D | CSN1S1 |
| P47929 | Galectin-7 | LGALS7B |
| P47972 | Neuronal pentraxin-2 | NPTX2 |
| P47989 | Xanthine oxidase | XDH |
| P47992 | Lymphotactin | XCL1 |
| P48023 | Tumor necrosis factor ligand superfamily member 6, membrane form | FASLG |
| P48052 | Carboxypeptidase A2 | CPA2 |
| P48061 | Stromal cell-derived factor 1 | CXCL12 |
| P48304 | Lithostathine-1-beta | REG1B |
| P48307 | Tissue factor pathway inhibitor 2 | TFPI2 |
| P48357 | Leptin receptor | LEPR |
| P48594 | Serpin B4 | SERPINB4 |
| P48645 | Neuromedin-U-25 | NMU |
| P48740 | Mannan-binding lectin serine protease 1 | MASP1 |
| P48745 | Protein NOV homolog | NOV |
| P48960 | CD97 antigen subunit beta | CD97 |
| P49223 | Kunitz-type protease inhibitor 3 | SPINT3 |
| P49747 | Cartilage oligomeric matrix protein | COMP |
| P49763 | Placenta growth factor | PGF |
| P49765 | Vascular endothelial growth factor B | VEGFB |
| P49767 | Vascular endothelial growth factor C | VEGFC |
| P49771 | Fms-related tyrosine kinase 3 ligand | FLT3LG |
| P49862 | Kallikrein-7 | KLK7 |
| P49863 | Granzyme K | GZMK |
| P49908 | Selenoprotein P | SEPP1 |
| P49913 | Antibacterial protein FALL-39 | CAMP |
| P50607 | Tubby protein homolog | TUB |
| P51124 | Granzyme M | GZMM |
| P51512 | Matrix metalloproteinase-16 | MMP16 |
| P51654 | Glypican-3 | GPC3 |
| P51671 | Eotaxin | CCL11 |
| P51884 | Lumican | LUM |
| P51888 | Prolargin | PRELP |
| P52798 | Ephrin-A4 | EFNA4 |
| P52823 | Stanniocalcin-1 | STC1 |
| P53420 | Collagen alpha-4(IV) chain | COL4A4 |
| P53621 | Coatomer subunit alpha | COPA |
| P54108 | Cysteine-rich secretory protein 3 | CRISP3 |
| P54315 | Pancreatic lipase-related protein 1 | PNLIPRP1 |
| P54317 | Pancreatic lipase-related protein 2 | PNLIPRP2 |
| P54793 | Arylsulfatase F | ARSF |
| P55000 | Secreted Ly-6/uPAR-related protein 1 | SLURP1 |
| P55001 | Microfibrillar-associated protein 2 | MFAP2 |
| P55056 | Apolipoprotein C-IV | APOC4 |
| P55058 | Phospholipid transfer protein | PLTP |
| P55075 | Fibroblast growth factor 8 | FGF8 |
| P55081 | Microfibrillar-associated protein 1 | MFAP1 |
| P55083 | Microfibril-associated glycoprotein 4 | MFAP4 |
| P55107 | Bone morphogenetic protein 3B | GDF10 |
| P55145 | Mesencephalic astrocyte-derived neurotrophic factor | MANF |
| P55259 | Pancreatic secretory granule membrane major glycoprotein GP2 | GP2 |
| P55268 | Laminin subunit beta-2 | LAMB2 |
| P55773 | CCL23(30-99) | CCL23 |
| P55774 | C-C motif chemokine 18 | CCL18 |
| P55789 | FAD-linked sulfhydryl oxidase ALR | GFER |
| P56703 | Proto-oncogene Wnt-3 | WNT3 |
| P56704 | Protein Wnt-3a | WNT3A |
| P56705 | Protein Wnt-4 | WNT4 |
| P56706 | Protein Wnt-7b | WNT7B |
| P56730 | Neurotrypsin | PRSS12 |
| P56851 | Epididymal secretory protein E3-beta | EDDM3B |
| P56975 | Neuregulin-3 | NRG3 |
| P58062 | Serine protease inhibitor Kazal-type 7 | SPINK7 |
| P58215 | Lysyl oxidase homolog 3 | LOXL3 |
| P58294 | Prokineticin-1 | PROK1 |

TABLE 1-continued

Secreted Proteins

| Uniprot ID | Protein Name | Gene Name |
|---|---|---|
| P58335 | Anthrax toxin receptor 2 | ANTXR2 |
| P58397 | A disintegrin and metalloproteinase with thrombospondin motifs 12 | ADAMTS12 |
| P58417 | Neurexophilin-1 | NXPH1 |
| P58499 | Protein FAM3B | FAM3B |
| P59510 | A disintegrin and metalloproteinase with thrombospondin motifs 20 | ADAMTS20 |
| P59665 | Neutrophil defensin 1 | DEFA1B |
| P59666 | Neutrophil defensin 3 | DEFA3 |
| P59796 | Glutathione peroxidase 6 | GPX6 |
| P59826 | BPI fold-containing family B member 3 | BPIFB3 |
| P59827 | BPI fold-containing family B member 4 | BPIFB4 |
| P59861 | Beta-defensin 131 | DEFB131 |
| P60022 | Beta-defensin 1 | DEFB1 |
| P60153 | Inactive ribonuclease-like protein 9 | RNASE9 |
| P60827 | Complement C1q tumor necrosis factor-related protein 8 | C1QTNF8 |
| P60852 | Zona pellucida sperm-binding protein 1 | ZP1 |
| P60985 | Keratinocyte differentiation-associated protein | KRTDAP |
| P61109 | Kidney androgen-regulated protein | KAP |
| P61278 | Somatostatin-14 | SST |
| P61366 | Osteocrin | OSTN |
| P61626 | Lysozyme C | LYZ |
| P61769 | Beta-2-microglobulin | B2M |
| P61812 | Transforming growth factor beta-2 | TGFB2 |
| P61916 | Epididymal secretory protein E1 | NPC2 |
| P62502 | Epididymal-specific lipocalin-6 | LCN6 |
| P62937 | Peptidyl-prolyl cis-trans isomerase A | PPIA |
| P67809 | Nuclease-sensitive element-binding protein 1 | YBX1 |
| P67812 | Signal peptidase complex catalytic subunit SEC11A | SEC11A |
| P78310 | Coxsackievirus and adenovirus receptor | CXADR |
| P78333 | Secreted glypican-5 | GPC5 |
| P78380 | Oxidized low-density lipoprotein receptor 1 | OLR1 |
| P78423 | Processed fractalkine | CX3CL1 |
| P78509 | Reelin | RELN |
| P78556 | CCL20(2-70) | CCL20 |
| P80075 | MCP-2(6-76) | CCL8 |
| P80098 | C-C motif chemokine 7 | CCL7 |
| P80108 | Phosphatidylinositol-glycan-specific phospholipase D | GPLD1 |
| P80162 | C-X-C motif chemokine 6 | CXCL6 |
| P80188 | Neutrophil gelatinase-associated lipocalin | LCN2 |
| P80303 | Nucleobindin-2 | NUCB2 |
| P80511 | Calcitermin | S100A12 |
| P81172 | Hepcidin-25 | HAMP |
| P81277 | Prolactin-releasing peptide | PRLH |
| P81534 | Beta-defensin 103 | DEFB103A |
| P81605 | Dermcidin | DCD |
| P82279 | Protein crumbs homolog 1 | CRB1 |
| P82987 | ADAMTS-like protein 3 | ADAMTSL3 |
| P83105 | Serine protease HTRA4 | HTRA4 |
| P83110 | Serine protease HTRA3 | HTRA3 |
| P83859 | Orexigenic neuropeptide QRFP | QRFP |
| P98088 | Mucin-5AC | MUC5AC |
| P98095 | Fibulin-2 | FBLN2 |
| P98160 | Basement membrane-specific heparan sulfate proteoglycan core protein | HSPG2 |
| P98173 | Protein FAM3A | FAM3A |
| Q00604 | Norrin | NDP |
| Q00796 | Sorbitol dehydrogenase | SORD |
| Q00887 | Pregnancy-specific beta-1-glycoprotein 9 | PSG9 |
| Q00888 | Pregnancy-specific beta-1-glycoprotein 4 | PSG4 |
| Q00889 | Pregnancy-specific beta-1-glycoprotein 6 | PSG6 |
| Q01523 | HD5(56-94) | DEFA5 |
| Q01524 | Defensin-6 | DEFA6 |
| Q01955 | Collagen alpha-3(IV) chain | COL4A3 |
| Q02297 | Pro-neuregulin-1, membrane-bound isoform | NRG1 |
| Q02325 | Plasminogen-like protein B | PLGLB1 |
| Q02383 | Semenogelin-2 | SEMG2 |
| Q02388 | Collagen alpha-1(VII) chain | COL7A1 |
| Q02505 | Mucin-3A | MUC3A |
| Q02509 | Otoconin-90 | OC90 |
| Q02747 | Guanylin | GUCA2A |
| Q02763 | Angiopoietin-1 receptor | TEK |
| Q02817 | Mucin-2 | MUC2 |

TABLE 1-continued

Secreted Proteins

| Uniprot ID | Protein Name | Gene Name |
| --- | --- | --- |
| Q02985 | Complement factor H-related protein 3 | CFHR3 |
| Q03167 | Transforming growth factor beta receptor type 3 | TGFBR3 |
| Q03403 | Trefoil factor 2 | TFF2 |
| Q03405 | Urokinase plasminogen activator surface receptor | PLAUR |
| Q03591 | Complement factor H-related protein 1 | CFHR1 |
| Q03692 | Collagen alpha-1(X) chain | COL10A1 |
| Q04118 | Basic salivary proline-rich protein 3 | PRB3 |
| Q04756 | Hepatocyte growth factor activator short chain | HGFAC |
| Q04900 | Sialomucin core protein 24 | CD164 |
| Q05315 | Eosinophil lysophospholipase | CLC |
| Q05707 | Collagen alpha-1 (XIV) chain | COL14A1 |
| Q05996 | Processed zona pellucida sperm-binding protein 2 | ZP2 |
| Q06033 | Inter-alpha-trypsin inhibitor heavy chain H3 | ITIH3 |
| Q06141 | Regenerating islet-derived protein 3-alpha | REG3A |
| Q06828 | Fibromodulin | FMOD |
| Q07092 | Collagen alpha-1(XVI) chain | COL16A1 |
| Q07325 | C-X-C motif chemokine 9 | CXCL9 |
| Q07507 | Dermatopontin | DPT |
| Q075Z2 | Binder of sperm protein homolog 1 | BSPH1 |
| Q07654 | Trefoil factor 3 | TFF3 |
| Q07699 | Sodium channel subunit beta-1 | SCN1B |
| Q08345 | Epithelial discoidin domain-containing receptor 1 | DDR1 |
| Q08380 | Galectin-3-binding protein | LGALS3BP |
| Q08397 | Lysyl oxidase homolog 1 | LOXL1 |
| Q08431 | Lactadherin | MFGE8 |
| Q08629 | Testican-1 | SPOCK1 |
| Q08648 | Sperm-associated antigen 11B | SPAG11B |
| Q08830 | Fibrinogen-like protein 1 | FGL1 |
| Q10471 | Polypeptide N-acetylgalactosaminyltransferase 2 | GALNT2 |
| Q10472 | Polypeptide N-acetylgalactosaminyltransferase 1 | GALNT1 |
| Q11201 | CMP-N-acetylneuraminate-beta-galactosamide-alpha-2,3-sialyltransferase 1 | ST3GAL1 |
| Q11203 | CMP-N-acetylneuraminate-beta-1,4-galactoside alpha-2,3-sialyltransferase | ST3GAL3 |
| Q11206 | CMP-N-acetylneuraminate-beta-galactosamide-alpha-2,3-sialyltransferase 4 | ST3GAL4 |
| Q12794 | Hyaluronidase-1 | HYAL1 |
| Q12805 | EGF-containing fibulin-like extracellular matrix protein 1 | EFEMP1 |
| Q12836 | Zona pellucida sperm-binding protein 4 | ZP4 |
| Q12841 | Follistatin-related protein 1 | FSTL1 |
| Q12904 | Aminoacyl tRNA synthase complex-interacting multifunctional protein 1 | AIMP1 |
| Q13018 | Soluble secretory phospholipase A2 receptor | PLA2R1 |
| Q13072 | B melanoma antigen 1 | BAGE |
| Q13093 | Platelet-activating factor acetylhydrolase | PLA2G7 |
| Q13103 | Secreted phosphoprotein 24 | SPP2 |
| Q13162 | Peroxiredoxin-4 | PRDX4 |
| Q13201 | Platelet glycoprotein Ia* | MMRN1 |
| Q13214 | Semaphorin-3B | SEMA3B |
| Q13219 | Pappalysin-1 | PAPPA |
| Q13231 | Chitotriosidase-1 | CHIT1 |
| Q13253 | Noggin | NOG |
| Q13261 | Interleukin-15 receptor subunit alpha | IL15RA |
| Q13275 | Semaphorin-3F | SEMA3F |
| Q13291 | Signaling lymphocytic activation molecule | SLAMF1 |
| Q13316 | Dentin matrix acidic phosphoprotein 1 | DMP1 |
| Q13361 | Microfibrillar-associated protein 5 | MFAP5 |
| Q13410 | Butyrophilin subfamily 1 member A1 | BTN1A1 |
| Q13421 | Mesothelin, cleaved form | MSLN |
| Q13429 | Insulin-like growth factor I | IGF-I |
| Q13443 | Disintegrin and metalloproteinase domain-containing protein 9 | ADAM9 |
| Q13519 | Neuropeptide 1 | PNOC |
| Q13751 | Laminin subunit beta-3 | LAMB3 |
| Q13753 | Laminin subunit gamma-2 | LAMC2 |
| Q13790 | Apolipoprotein F | APOF |
| Q13822 | Ectonucleotide pyrophosphatase/phosphodiesterase family member 2 | ENPP2 |
| Q14031 | Collagen alpha-6(IV) chain | COL4A6 |
| Q14050 | Collagen alpha-3(IX) chain | COL9A3 |
| Q14055 | Collagen alpha-2(IX) chain | COL9A2 |
| Q14112 | Nidogen-2 | NID2 |
| Q14114 | Low-density lipoprotein receptor-related protein 8 | LRP8 |
| Q14118 | Dystroglycan | DAG1 |

TABLE 1-continued

Secreted Proteins

| Uniprot ID | Protein Name | Gene Name |
| --- | --- | --- |
| Q14314 | Fibroleukin | FGL2 |
| Q14393 | Growth arrest-specific protein 6 | GAS6 |
| Q14406 | Chorionic somatomammotropin hormone-like 1 | CSHL1 |
| Q14507 | Epididymal secretory protein E3-alpha | EDDM3A |
| Q14508 | WAP four-disulfide core domain protein 2 | WFDC2 |
| Q14512 | Fibroblast growth factor-binding protein 1 | FGFBP1 |
| Q14515 | SPARC-like protein 1 | SPARCL1 |
| Q14520 | Hyaluronan-binding protein 2 27 kDa light chain | HABP2 |
| Q14563 | Semaphorin-3A | SEMA3A |
| Q14623 | Indian hedgehog protein | IHH |
| Q14624 | Inter-alpha-trypsin inhibitor heavy chain H4 | ITIH4 |
| Q14667 | UPF0378 protein KIAA0100 | KIAA0100 |
| Q14703 | Membrane-bound transcription factor site-1 protease | MBTPS1 |
| Q14766 | Latent-transforming growth factor beta-binding protein 1 | LTBP1 |
| Q14767 | Latent-transforming growth factor beta-binding protein 2 | LTBP2 |
| Q14773 | Intercellular adhesion molecule 4 | ICAM4 |
| Q14993 | Collagen alpha-1(XIX) chain | COL19A1 |
| Q14CN2 | Calcium-activated chloride channel regulator 4, 110 kDa form | CLCA4 |
| Q15046 | Lysine--tRNA ligase | KARS |
| Q15063 | Periostin | POSTN |
| Q15109 | Advanced glycosylation end product-specific receptor | AGER |
| Q15113 | Procollagen C-endopeptidase enhancer 1 | PCOLCE |
| Q15166 | Serum paraoxonase/lactonase 3 | PON3 |
| Q15195 | Plasminogen-like protein A | PLGLA |
| Q15198 | Platelet-derived growth factor receptor-like protein | PDGFRL |
| Q15223 | Poliovirus receptor-related protein 1 | PVRL1 |
| Q15238 | Pregnancy-specific beta-1-glycoprotein 5 | PSG5 |
| Q15363 | Transmembrane emp24 domain-containing protein 2 | TMED2 |
| Q15375 | Ephrin type-A receptor 7 | EPHA7 |
| Q15389 | Angiopoietin-1 | ANGPT1 |
| Q15465 | Sonic hedgehog protein | SHH |
| Q15485 | Ficolin-2 | FCN2 |
| Q15517 | Corneodesmosin | CDSN |
| Q15582 | Transforming growth factor-beta-induced protein ig-h3 | TGFBI |
| Q15661 | Tryptase alpha/beta-1 | TPSAB1 |
| Q15726 | Metastin | KISS1 |
| Q15782 | Chitinase-3-like protein 2 | CHI3L2 |
| Q15828 | Cystatin-M | CST6 |
| Q15846 | Clusterin-like protein 1 | CLUL1 |
| Q15848 | Adiponectin | ADIPOQ |
| Q16206 | Protein disulfide-thiol oxidoreductase | ENOX2 |
| Q16270 | Insulin-like growth factor-binding protein 7 | IGFBP7 |
| Q16363 | Laminin subunit alpha-4 | LAMA4 |
| Q16378 | Proline-rich protein 4 | PRR4 |
| Q16557 | Pregnancy-specific beta-1-glycoprotein 3 | PSG3 |
| Q16568 | CART(42-89) | CARTPT |
| Q16610 | Extracellular matrix protein 1 | ECM1 |
| Q16619 | Cardiotrophin-1 | CTF1 |
| Q16623 | Syntaxin-1A | STX1A |
| Q16627 | HCC-1(9-74) | CCL14 |
| Q16651 | Prostasin light chain | PRSS8 |
| Q16661 | Guanylate cyclase C-activating peptide 2 | GUCA2B |
| Q16663 | CCL15(29-92) | CCL15 |
| Q16674 | Melanoma-derived growth regulatory protein | MIA |
| Q16769 | Glutaminyl-peptide cyclotransferase | QPCT |
| Q16787 | Laminin subunit alpha-3 | LAMA3 |
| Q16842 | CMP-N-acetylneuraminate-beta-galactosamide-alpha-2,3-sialyltransferase 2 | ST3GAL2 |
| Q17RR3 | Pancreatic lipase-related protein 3 | PNLIPRP3 |
| Q17RW2 | Collagen alpha-1(XXIV) chain | COL24A1 |
| Q17RY6 | Lymphocyte antigen 6K | LY6K |
| Q1L6U9 | Prostate-associated microseminoprotein | MSMP |
| Q1W4C9 | Serine protease inhibitor Kazal-type 13 | SPINK13 |
| Q1ZYL8 | Izumo sperm-egg fusion protein 4 | IZUMO4 |
| Q29960 | HLA class I histocompatibility antigen, Cw-16 alpha chain | HLA-C |
| Q2I0M5 | R-spondin-4 | RSPO4 |
| Q2L4Q9 | Serine protease 53 | PRSS53 |
| Q2MKA7 | R-spondin-1 | RSPO1 |
| Q2MV58 | Tectonic-1 | TCTN1 |

TABLE 1-continued

Secreted Proteins

| Uniprot ID | Protein Name | Gene Name |
| --- | --- | --- |
| Q2TAL6 | Brorin | VWC2 |
| Q2UY09 | Collagen alpha-1(XXVIII) chain | COL28A1 |
| Q2VPA4 | Complement component receptor 1-like protein | CR1L |
| Q2WEN9 | Carcinoembryonic antigen-related cell adhesion molecule 16 | CEACAM16 |
| Q30KP8 | Beta-defensin 136 | DEFB136 |
| Q30KP9 | Beta-defensin 135 | DEFB135 |
| Q30KQ1 | Beta-defensin 133 | DEFB133 |
| Q30KQ2 | Beta-defensin 130 | DEFB130 |
| Q30KQ4 | Beta-defensin 116 | DEFB116 |
| Q30KQ5 | Beta-defensin 115 | DEFB115 |
| Q30KQ6 | Beta-defensin 114 | DEFB114 |
| Q30KQ7 | Beta-defensin 113 | DEFB113 |
| Q30KQ8 | Beta-defensin 112 | DEFB112 |
| Q30KQ9 | Beta-defensin 110 | DEFB110 |
| Q30KR1 | Beta-defensin 109 | DEFB109P1 |
| Q32P28 | Prolyl 3-hydroxylase 1 | LEPRE1 |
| Q3B7J2 | Glucose-fructose oxidoreductase domain-containing protein 2 | GFOD2 |
| Q3SY79 | Protein Wnt | WNT3A |
| Q3T906 | N-acetylglucosamine-1-phosphotransferase subunits alpha/beta | GNPTAB |
| Q495T6 | Membrane metallo-endopeptidase-like 1 | MMEL1 |
| Q49AH0 | Cerebral dopamine neurotrophic factor | CDNF |
| Q4G0G5 | Secretoglobin family 2B member 2 | SCGB2B2 |
| Q4G0M1 | Protein FAM132B | FAM132B |
| Q4LDE5 | Sushi, von Willebrand factor type A, EGF and pentraxin domain-containing protein 1 | SVEP1 |
| Q4QY38 | Beta-defensin 134 | DEFB134 |
| Q4VAJ4 | Protein Wnt | WNT10B |
| Q4W5P6 | Protein TMEM155 | TMEM155 |
| Q4ZHG4 | Fibronectin type III domain-containing protein 1 | FNDC1 |
| Q53H76 | Phospholipase A1 member A | PLA1A |
| Q53RD9 | Fibulin-7 | FBLN7 |
| Q53S33 | BolA-like protein 3 | BOLA3 |
| Q5BLP8 | Neuropeptide-like protein C4orf48 | C4orf48 |
| Q5DT21 | Serine protease inhibitor Kazal-type 9 | SPINK9 |
| Q5EBL8 | PDZ domain-containing protein 11 | PDZD11 |
| Q5FYB0 | Arylsulfatase J | ARSJ |
| Q5FYB1 | Arylsulfatase I | ARSI |
| Q5GAN3 | Ribonuclease-like protein 13 | RNASE13 |
| Q5GAN4 | Ribonuclease-like protein 12 | RNASE12 |
| Q5GAN6 | Ribonuclease-like protein 10 | RNASE10 |
| Q5GFL6 | von Willebrand factor A domain-containing protein 2 | VWA2 |
| Q5H8A3 | Neuromedin-S | NMS |
| Q5H8C1 | FRAS1-related extracellular matrix protein 1 | FREM1 |
| Q5IJ48 | Protein crumbs homolog 2 | CRB2 |
| Q5J5C9 | Beta-defensin 121 | DEFB121 |
| Q5JS37 | NHL repeat-containing protein 3 | NHLRC3 |
| Q5JTB6 | Placenta-specific protein 9 | PLAC9 |
| Q5JU69 | Torsin-2A | TOR2A |
| Q5JXM2 | Methyltransferase-like protein 24 | METTL24 |
| Q5JZY3 | Ephrin type-A receptor 10 | EPHA10 |
| Q5K4E3 | Polyserase-2 | PRSS36 |
| Q5SRR4 | Lymphocyte antigen 6 complex locus protein G5c | LY6G5C |
| Q5T1H1 | Protein eyes shut homolog | EYS |
| Q5T4F7 | Secreted frizzled-related protein 5 | SFRP5 |
| Q5T4W7 | Artemin | ARTN |
| Q5T7M4 | Protein FAM132A | FAM132A |
| Q5TEH8 | Protein Wnt | WNT2B |
| Q5TIE3 | von Willebrand factor A domain-containing protein 5B1 | VWA5B1 |
| Q5UCC4 | ER membrane protein complex subunit 10 | EMC10 |
| Q5VST6 | Abhydrolase domain-containing protein FAM108B1 | FAM108B1 |
| Q5VTL7 | Fibronectin type III domain-containing protein 7 | FNDC7 |
| Q5VUM1 | UPF0369 protein C6orf57 | C6orf57 |
| Q5VV43 | Dyslexia-associated protein KIAA0319 | KIAA0319 |
| Q5VWW1 | Complement C1q-like protein 3 | C1QL3 |
| Q5VXI9 | Lipase member N | LIPN |
| Q5VXJ0 | Lipase member K | LIPK |
| Q5VXM1 | CUB domain-containing protein 2 | CDCP2 |
| Q5VYX0 | Renalase | RNLS |
| Q5VYY2 | Lipase member M | LIPM |
| Q5W186 | Cystatin-9 | CST9 |

TABLE 1-continued

Secreted Proteins

| Uniprot ID | Protein Name | Gene Name |
|---|---|---|
| Q5W5W9 | Regulated endocrine-specific protein 18 | RESP18 |
| Q5XG92 | Carboxylesterase 4A | CES4A |
| Q63HQ2 | Pikachurin | EGFLAM |
| Q641Q3 | Meteorin-like protein | METRNL |
| Q66K79 | Carboxypeptidase Z | CPZ |
| Q685J3 | Mucin-17 | MUC17 |
| Q68BL7 | Olfactomedin-like protein 2A | OLFML2A |
| Q68BL8 | Olfactomedin-like protein 2B | OLFML2B |
| Q68DV7 | E3 ubiquitin-protein ligase RNF43 | RNF43 |
| Q6B9Z1 | Insulin growth factor-like family member 4 | IGFL4 |
| Q6BAA4 | Fc receptor-like B | FCRLB |
| Q6E0U4 | Dermokine | DMKN |
| Q6EMK4 | Vasorin | VASN |
| Q6FHJ7 | Secreted frizzled-related protein 4 | SFRP4 |
| Q6GPI1 | Chymotrypsin B2 chain B | CTRB2 |
| Q6GTS8 | Probable carboxypeptidase PM20D1 | PM20D1 |
| Q6H9L7 | Isthmin-2 | ISM2 |
| Q6IE36 | Ovostatin homolog 2 | OVOS2 |
| Q6IE37 | Ovostatin homolog 1 | OVOS1 |
| Q6IE38 | Serine protease inhibitor Kazal-type 14 | SPINK14 |
| Q6ISS4 | Leukocyte-associated immunoglobulin-like receptor 2 | LAIR2 |
| Q6JVE5 | Epididymal-specific lipocalin-12 | LCN12 |
| Q6JVE6 | Epididymal-specific lipocalin-10 | LCN10 |
| Q6JVE9 | Epididymal-specific lipocalin-8 | LCN8 |
| Q6KF10 | Growth/differentiation factor 6 | GDF6 |
| Q6MZW2 | Follistatin-related protein 4 | FSTL4 |
| Q6NSX1 | Coiled-coil domain-containing protein 70 | CCDC70 |
| Q6NT32 | Carboxylesterase 5A | CES5A |
| Q6NT52 | Choriogonadotropin subunit beta variant 2 | CGB2 |
| Q6NUI6 | Chondroactherin-like protein | CHADL |
| Q6NUJ1 | Saposin A-like | PSAPL1 |
| Q6P093 | Arylacetamide deacetylase-like 2 | AADACL2 |
| Q6P4A8 | Phospholipase B-like 1 | PLBD1 |
| Q6P5S2 | UPF0762 protein C6orf58 | C6orf58 |
| Q6P988 | Protein notum homolog | NOTUM |
| Q6PCB0 | von Willebrand factor A domain-containing protein 1 | VWA1 |
| Q6PDA7 | Sperm-associated antigen 11A | SPAG11A |
| Q6PEW0 | Inactive serine protease 54 | PRSS54 |
| Q6PEZ8 | Podocan-like protein 1 | PODNL1 |
| Q6PKH6 | Dehydrogenase/reductase SDR family member 4-like 2 | DHRS4L2 |
| Q6Q788 | Apolipoprotein A-V | APOA5 |
| Q6SPF0 | Atherin | SAMD1 |
| Q6UDR6 | Kunitz-type protease inhibitor 4 | SPINT4 |
| Q6URK8 | Testis, prostate and placenta-expressed protein | TEPP |
| Q6UW01 | Cerebellin-3 | CBLN3 |
| Q6UW10 | Surfactant-associated protein 2 | SFTA2 |
| Q6UW15 | Regenerating islet-derived protein 3-gamma | REG3G |
| Q6UW32 | Insulin growth factor-like family member 1 | IGFL1 |
| Q6UW78 | UPF0723 protein C11orf83 | C11orf83 |
| Q6UW88 | Epigen | EPGN |
| Q6UWE3 | Colipase-like protein 2 | CLPSL2 |
| Q6UWF7 | NXPE family member 4 | NXPE4 |
| Q6UWF9 | Protein FAM180A | FAM180A |
| Q6UWM5 | GLIPR1-like protein 1 | GLIPR1L1 |
| Q6UWN8 | Serine protease inhibitor Kazal-type 6 | SPINK6 |
| Q6UWP2 | Dehydrogenase/reductase SDR family member 11 | DHRS11 |
| Q6UWP8 | Suprabasin | SBSN |
| Q6UWQ5 | Lysozyme-like protein 1 | LYZL1 |
| Q6UWQ7 | Insulin growth factor-like family member 2 | IGFL2 |
| Q6UWR7 | Ectonucleotide pyrophosphatase/phosphodiesterase family member 6 soluble form | ENPP6 |
| Q6UWT2 | Adropin | ENHO |
| Q6UWU2 | Beta-galactosidase-1-like protein | GLB1L |
| Q6UWW0 | Lipocalin-15 | LCN15 |
| Q6UWX4 | HHIP-like protein 2 | HHIPL2 |
| Q6UWY0 | Arylsulfatase K | ARSK |
| Q6UWY2 | Serine protease 57 | PRSS57 |
| Q6UWY5 | Olfactomedin-like protein 1 | OLFML1 |
| Q6UX06 | Olfactomedin-4 | OLFM4 |
| Q6UX07 | Dehydrogenase/reductase SDR family member 13 | DHRS13 |
| Q6UX39 | Amelotin | AMTN |
| Q6UX46 | Protein FAM150B | FAM150B |

TABLE 1-continued

Secreted Proteins

| Uniprot ID | Protein Name | Gene Name |
|---|---|---|
| Q6UX73 | UPF0764 protein C16orf89 | C16orf89 |
| Q6UXB0 | Protein FAM131A | FAM131A |
| Q6UXB1 | Insulin growth factor-like family member 3 | IGFL3 |
| Q6UXB2 | VEGF co-regulated chemokine 1 | CXCL17 |
| Q6UXF7 | C-type lectin domain family 18 member B | CLEC18B |
| Q6UXH0 | Hepatocellular carcinoma-associated protein TD26 | C19orf80 |
| Q6UXH1 | Cysteine-rich with EGF-like domain protein 2 | CRELD2 |
| Q6UXH8 | Collagen and calcium-binding EGF domain-containing protein 1 | CCBE1 |
| Q6UXH9 | Inactive serine protease PAMR1 | PAMR1 |
| Q6UXI7 | Vitrin | VIT |
| Q6UXI9 | Nephronectin | NPNT |
| Q6UXN2 | Trem-like transcript 4 protein | TREML4 |
| Q6UXS0 | C-type lectin domain family 19 member A | CLEC19A |
| Q6UXT8 | Protein FAM150A | FAM150A |
| Q6UXT9 | Abhydrolase domain-containing protein 15 | ABHD15 |
| Q6UXV4 | Apolipoprotein O-like | APOOL |
| Q6UXX5 | Inter-alpha-trypsin inhibitor heavy chain H6 | ITIH6 |
| Q6UXX9 | R-spondin-2 | RSPO2 |
| Q6UY14 | ADAMTS-like protein 4 | ADAMTSL4 |
| Q6UY27 | Prostate and testis expressed protein 2 | PATE2 |
| Q6W4X9 | Mucin-6 | MUC6 |
| Q6WN34 | Chordin-like protein 2 | CHRDL2 |
| Q6WRI0 | Immunoglobulin superfamily member 10 | IGSF10 |
| Q6X4U4 | Sclerostin domain-containing protein 1 | SOSTDC1 |
| Q6X784 | Zona pellucida-binding protein 2 | ZPBP2 |
| Q6XE38 | Secretoglobin family 1D member 4 | SCGB1D4 |
| Q6XPR3 | Repetin | RPTN |
| Q6XZB0 | Lipase member I | LIPI |
| Q6ZMM2 | ADAMTS-like protein 5 | ADAMTSL5 |
| Q6ZMP0 | Thrombospondin type-1 domain-containing protein 4 | THSD4 |
| Q6ZNF0 | Iron/zinc purple acid phosphatase-like protein | PAPL |
| Q6ZRI0 | Otogelin | OTOG |
| Q6ZRP7 | Sulfhydryl oxidase 2 | QSOX2 |
| Q6ZWJ8 | Kielin/chordin-like protein | KCP |
| Q75N90 | Fibrillin-3 | FBN3 |
| Q76SI0 | Urotensin-2B | UTS2D |
| Q76B58 | Protein FAM5C | FAM5C |
| Q76LX8 | A disintegrin and metalloproteinase with thrombospondin motifs 13 | ADAMTS13 |
| Q76M96 | Coiled-coil domain-containing protein 80 | CCDC80 |
| Q7L1S5 | Carbohydrate sulfotransferase 9 | CHST9 |
| Q7L513 | Fc receptor-like A | FCRLA |
| Q7L8A9 | Vasohibin-1 | VASH1 |
| Q7RTM1 | Otopetrin-1 | OTOP1 |
| Q7RTW8 | Otoancorin | OTOA |
| Q7RTY5 | Serine protease 48 | PRSS48 |
| Q7RTY7 | Ovochymase-1 | OVCH1 |
| Q7RTZ1 | Ovochymase-2 | OVCH2 |
| Q7Z304 | MAM domain-containing protein 2 | MAMDC2 |
| Q7Z3S9 | Notch homolog 2 N-terminal-like protein | NOTCH2NL |
| Q7Z4H4 | Intermedin-short | ADM2 |
| Q7Z4P5 | Growth/differentiation factor 7 | GDF7 |
| Q7Z4R8 | UPF0669 protein C6orf120 | C6orf120 |
| Q7Z4W2 | Lysozyme-like protein 2 | LYZL2 |
| Q7Z5A4 | Serine protease 42 | PRSS42 |
| Q7Z5A7 | Protein FAM19A5 | FAM19A5 |
| Q7Z5A8 | Protein FAM19A3 | FAM19A3 |
| Q7Z5A9 | Protein FAM19A1 | FAM19A1 |
| Q7Z5J1 | Hydroxysteroid 11-beta-dehydrogenase 1-like protein | HSD11B1L |
| Q7Z5L0 | Vitelline membrane outer layer protein 1 homolog | VMO1 |
| Q7Z5L3 | Complement C1q-like protein 2 | C1QL2 |
| Q7Z5L7 | Podocan | PODN |
| Q7Z5P4 | 17-beta-hydroxysteroid dehydrogenase 13 | HSD17B13 |
| Q7Z5P9 | Mucin-19 | MUC19 |
| Q7Z5Y6 | Bone morphogenetic protein 8A | BMP8A |
| Q7Z7B7 | Beta-defensin 132 | DEFB132 |
| Q7Z7B8 | Beta-defensin 128 | DEFB128 |
| Q7Z7C8 | Transcription initiation factor TFIID subunit 8 | TAF8 |
| Q7Z7H5 | Transmembrane emp24 domain-containing protein 4 | TMED4 |
| Q86SG7 | Lysozyme g-like protein 2 | LYG2 |
| Q86SI9 | Protein CEI | C5orf38 |
| Q86TE4 | Leucine zipper protein 2 | LUZP2 |
| Q86TH1 | ADAMTS-like protein 2 | ADAMTSL2 |

TABLE 1-continued

Secreted Proteins

| Uniprot ID | Protein Name | Gene Name |
| --- | --- | --- |
| Q86U17 | Serpin A11 | SERPINA11 |
| Q86UU9 | Endokinin-A | TAC4 |
| Q86UW8 | Hyaluronan and proteoglycan link protein 4 | HAPLN4 |
| Q86UX2 | Inter-alpha-trypsin inhibitor heavy chain H5 | ITIH5 |
| Q86V24 | Adiponectin receptor protein 2 | ADIPOR2 |
| Q86VB7 | Soluble CD163 | CD163 |
| Q86VR8 | Four-jointed box protein 1 | FJX1 |
| Q86WD7 | Serpin A9 | SERPINA9 |
| Q86WN2 | Interferon epsilon | IFNE |
| Q86WS3 | Placenta-specific 1-like protein | PLAC1L |
| Q86X52 | Chondroitin sulfate synthase 1 | CHSY1 |
| Q86XP6 | Gastrokine-2 | GKN2 |
| Q86XS5 | Angiopoietin-related protein 5 | ANGPTL5 |
| Q86Y27 | B melanoma antigen 5 | BAGE5 |
| Q86Y28 | B melanoma antigen 4 | BAGE4 |
| Q86Y29 | B melanoma antigen 3 | BAGE3 |
| Q86Y30 | B melanoma antigen 2 | BAGE2 |
| Q86Y38 | Xylosyltransferase 1 | XYLT1 |
| Q86Y78 | Ly6/PLAUR domain-containing protein 6 | LYPD6 |
| Q86YD3 | Transmembrane protein 25 | TMEM25 |
| Q86YJ6 | Threonine synthase-like 2 | THNSL2 |
| Q86YW7 | Glycoprotein hormone beta-5 | GPHB5 |
| Q86Z23 | Complement C1q-like protein 4 | C1QL4 |
| Q8IU57 | Interleukin-28 receptor subunit alpha | IL28RA |
| Q8IUA0 | WAP four-disulfide core domain protein 8 | WFDC8 |
| Q8IUB2 | WAP four-disulfide core domain protein 3 | WFDC3 |
| Q8IUB3 | Protein WFDC10B | WFDC10B |
| Q8IUB5 | WAP four-disulfide core domain protein 13 | WFDC13 |
| Q8IUH2 | Protein CREG2 | CREG2 |
| Q8IUK5 | Plexin domain-containing protein 1 | PLXDC1 |
| Q8IUL8 | Cartilage intermediate layer protein 2 C2 | CILP2 |
| Q8IUX7 | Adipocyte enhancer-binding protein 1 | AEBP1 |
| Q8IUX8 | Epidermal growth factor-like protein 6 | EGFL6 |
| Q8IVL8 | Carboxypeptidase O | CPO |
| Q8IVN8 | Somatomedin-B and thrombospondin type-1 domain-containing protein | SBSPON |
| Q8IVW8 | Protein spinster homolog 2 | SPNS2 |
| Q8IW75 | Serpin A12 | SERPINA12 |
| Q8IW92 | Beta-galactosidase-1-like protein 2 | GLB1L2 |
| Q8IWL1 | Pulmonary surfactant-associated protein A2 | SFTPA2 |
| Q8IWL2 | Pulmonary surfactant-associated protein A1 | SFTPA1 |
| Q8IWV2 | Contactin-4 | CNTN4 |
| Q8IWY4 | Signal peptide, CUB and EGF-like domain-containing protein 1 | SCUBE1 |
| Q8IX30 | Signal peptide, CUB and EGF-like domain-containing protein 3 | SCUBE3 |
| Q8IXA5 | Sperm acrosome membrane-associated protein 3, membrane form | SPACA3 |
| Q8IXB1 | DnaJ homolog subfamily C member 10 | DNAJC10 |
| Q8IXL6 | Extracellular serine/threonine protein kinase Fam20C | FAM20C |
| Q8IYD9 | Lung adenoma susceptibility protein 2 | LAS2 |
| Q8IYP2 | Serine protease 58 | PRSS58 |
| Q8IYS5 | Osteoclast-associated immunoglobulin-like receptor | OSCAR |
| Q8IZC6 | Collagen alpha-1(XXVII) chain | COL27A1 |
| Q8IZJ3 | C3 and PZP-like alpha-2-macroglobulin domain-containing protein 8 | CPAMD8 |
| Q8IZN7 | Beta-defensin 107 | DEFB107B |
| Q8N0V4 | Leucine-rich repeat LGI family member 2 | LGI2 |
| Q8N104 | Beta-defensin 106 | DEFB106B |
| Q8N119 | Matrix metalloproteinase-21 | MMP21 |
| Q8N129 | Protein canopy homolog 4 | CNPY4 |
| Q8N135 | Leucine-rich repeat LGI family member 4 | LGI4 |
| Q8N145 | Leucine-rich repeat LGI family member 3 | LGI3 |
| Q8N158 | Glypican-2 | GPC2 |
| Q8N1E2 | Lysozyme g-like protein 1 | LYG1 |
| Q8N2E2 | von Willebrand factor D and EGF domain-containing protein | VWDE |
| Q8N2E6 | Prosalusin | TOR2A |
| Q8N2S1 | Latent-transforming growth factor beta-binding protein 4 | LTBP4 |
| Q8N302 | Angiogenic factor with G patch and FHA domains 1 | AGGF1 |
| Q8N307 | Mucin-20 | MUC20 |
| Q8N323 | NXPE family member 1 | NXPE1 |
| Q8N387 | Mucin-15 | MUC15 |

TABLE 1-continued

Secreted Proteins

| Uniprot ID | Protein Name | Gene Name |
|---|---|---|
| Q8N3Z0 | Inactive serine protease 35 | PRSS35 |
| Q8N436 | Inactive carboxypeptidase-like protein X2 | CPXM2 |
| Q8N474 | Secreted frizzled-related protein 1 | SFRP1 |
| Q8N475 | Follistatin-related protein 5 | FSTL5 |
| Q8N4F0 | BPI fold-containing family B member 2 | BPIFB2 |
| Q8N4T0 | Carboxypeptidase A6 | CPA6 |
| Q8N5W8 | Protein FAM24B | FAM24B |
| Q8N687 | Beta-defensin 125 | DEFB125 |
| Q8N688 | Beta-defensin 123 | DEFB123 |
| Q8N690 | Beta-defensin 119 | DEFB119 |
| Q8N6C5 | Immunoglobulin superfamily member 1 | IGSF1 |
| Q8N6C8 | Leukocyte immunoglobulin-like receptor subfamily A member 3 | LILRA3 |
| Q8N6G6 | ADAMTS-like protein 1 | ADAMTSL1 |
| Q8N6Y2 | Leucine-rich repeat-containing protein 17 | LRRC17 |
| Q8N729 | Neuropeptide W-23 | NPW |
| Q8N8U9 | BMP-binding endothelial regulator protein | BMPER |
| Q8N907 | DAN domain family member 5 | DAND5 |
| Q8NAT1 | Glycosyltransferase-like domain-containing protein 2 | GTDC2 |
| Q8NAU1 | Fibronectin type III domain-containing protein 5 | FNDC5 |
| Q8NB37 | Parkinson disease 7 domain-containing protein 1 | PDDC1 |
| Q8NBI3 | Draxin | DRAXIN |
| Q8NBM8 | Prenylcysteine oxidase-like | PCYOX1L |
| Q8NBP7 | Proprotein convertase subtilisin/kexin type 9 | PCSK9 |
| Q8NBQ5 | Estradiol 17-beta-dehydrogenase 11 | HSD17B11 |
| Q8NBV8 | Synaptotagmin-8 | SYT8 |
| Q8NCC3 | Group XV phospholipase A2 | PLA2G15 |
| Q8NCF0 | C-type lectin domain family 18 member C | CLEC18C |
| Q8NCW5 | NAD(P)H-hydrate epimerase | APOA1BP |
| Q8NDA2 | Hemicentin-2 | HMCN2 |
| Q8NDX9 | Lymphocyte antigen 6 complex locus protein G5b | LY6G5B |
| Q8NDZ4 | Deleted in autism protein 1 | C3orf58 |
| Q8NEB7 | Acrosin-binding protein | ACRBP |
| Q8NES8 | Beta-defensin 124 | DEFB124 |
| Q8NET1 | Beta-defensin 108B | DEFB108B |
| Q8NEX5 | Protein WFDC9 | WFDC9 |
| Q8NEX6 | Protein WFDC11 | WFDC11 |
| Q8NF86 | Serine protease 33 | PRSS33 |
| Q8NFM7 | Interleukin-17 receptor D | IL17RD |
| Q8NFQ5 | BPI fold-containing family B member 6 | BPIFB6 |
| Q8NFQ6 | BPI fold-containing family C protein | BPIFC |
| Q8NFU4 | Follicular dendritic cell secreted peptide | FDCSP |
| Q8NFW1 | Collagen alpha-1(XXII) chain | COL22A1 |
| Q8NG35 | Beta-defensin 105 | DEFB105B |
| Q8NG41 | Neuropeptide B-23 | NPB |
| Q8NHW6 | Otospiralin | OTOS |
| Q8NI99 | Angiopoietin-related protein 6 | ANGPTL6 |
| Q8TAA1 | Probable ribonuclease 11 | RNASE11 |
| Q8TAG5 | V-set and transmembrane domain-containing protein 2A | VSTM2A |
| Q8TAL6 | Fin bud initiation factor homolog | FIBIN |
| Q8TAT2 | Fibroblast growth factor-binding protein 3 | FGFBP3 |
| Q8TAX7 | Mucin-7 | MUC7 |
| Q8TB22 | Spermatogenesis-associated protein 20 | SPATA20 |
| Q8TB73 | Protein NDNF | NDNF |
| Q8TB96 | T-cell immunomodulatory protein | ITFG1 |
| Q8TC92 | Protein disulfide-thiol oxidoreductase | ENOX1 |
| Q8TCV5 | WAP four-disulfide core domain protein 5 | WFDC5 |
| Q8TD06 | Anterior gradient protein 3 homolog | AGR3 |
| Q8TD33 | Secretoglobin family 1C member 1 | SCGB1C1 |
| Q8TD46 | Cell surface glycoprotein CD200 receptor 1 | CD200R1 |
| Q8TDE3 | Ribonuclease 8 | RNASE8 |
| Q8TDF5 | Neuropilin and tolloid-like protein 1 | NETO1 |
| Q8TDL5 | BPI fold-containing family B member 1 | BPIFB1 |
| Q8TE56 | A disintegrin and metalloproteinase with thrombospondin motifs 17 | ADAMTS17 |
| Q8TE57 | A disintegrin and metalloproteinase with thrombospondin motifs 16 | ADAMTS16 |
| Q8TE58 | A disintegrin and metalloproteinase with thrombospondin motifs 15 | ADAMTS15 |
| Q8TE59 | A disintegrin and metalloproteinase with thrombospondin motifs 19 | ADAMTS19 |
| Q8TE60 | A disintegrin and metalloproteinase with thrombospondin motifs 18 | ADAMTS18 |
| Q8TE99 | Acid phosphatase-like protein 2 | ACPL2 |

TABLE 1-continued

Secreted Proteins

| Uniprot ID | Protein Name | Gene Name |
|---|---|---|
| Q8TER0 | Sushi, nidogen and EGF-like domain-containing protein 1 | SNED1 |
| Q8TEU8 | WAP, kazal, immunoglobulin, kunitz and NTR domain-containing protein 2 | WFIKKN2 |
| Q8WTQ1 | Beta-defensin 104 | DEFB104B |
| Q8WTR8 | Netrin-5 | NTN5 |
| Q8WTU2 | Scavenger receptor cysteine-rich domain-containing group B protein | SRCRB4D |
| Q8WU66 | Protein TSPEAR | TSPEAR |
| Q8WUA8 | Tsukushin | TSKU |
| Q8WUF8 | Protein FAM172A | FAM172A |
| Q8WUJ1 | Neuferricin | CYB5D2 |
| Q8WUY1 | UPF0670 protein THEM6 | THEM6 |
| Q8WVN6 | Secreted and transmembrane protein 1 | SECTM1 |
| Q8WVQ1 | Soluble calcium-activated nucleotidase 1 | CANT1 |
| Q8WWA0 | Intelectin-1 | ITLN1 |
| Q8WWG1 | Neuregulin-4 | NRG4 |
| Q8WWQ2 | Inactive heparanase-2 | HPSE2 |
| Q8WWU7 | Intelectin-2 | ITLN2 |
| Q8WWY7 | WAP four-disulfide core domain protein 12 | WFDC12 |
| Q8WWY8 | Lipase member H | LIPH |
| Q8WWZ8 | Oncoprotein-induced transcript 3 protein | OIT3 |
| Q8WX39 | Epididymal-specific lipocalin-9 | LCN9 |
| Q8WXA2 | Prostate and testis expressed protein 1 | PATE1 |
| Q8WXD2 | Secretogranin-3 | SCG3 |
| Q8WXF3 | Relaxin-3 A chain | RLN3 |
| Q8WXI7 | Mucin-16 | MUC16 |
| Q8WXQ8 | Carboxypeptidase A5 | CPA5 |
| Q8WXS8 | A disintegrin and metalloproteinase with thrombospondin motifs 14 | ADAMTS14 |
| Q92484 | Acid sphingomyelinase-like phosphodiesterase 3a | SMPDL3A |
| Q92485 | Acid sphingomyelinase-like phosphodiesterase 3b | SMPDL3B |
| Q92496 | Complement factor H-related protein 4 | CFHR4 |
| Q92520 | Protein FAM3C | FAM3C |
| Q92563 | Testican-2 | SPOCK2 |
| Q92583 | C-C motif chemokine 17 | CCL17 |
| Q92626 | Peroxidasin homolog | PXDN |
| Q92743 | Serine protease HTRA1 | HTRA1 |
| Q92752 | Tenascin-R | TNR |
| Q92765 | Secreted frizzled-related protein 3 | FRZB |
| Q92819 | Hyaluronan synthase 2 | HAS2 |
| Q92820 | Gamma-glutamyl hydrolase | GGH |
| Q92824 | Proprotein convertase subtilisin/kexin type 5 | PCSK5 |
| Q92832 | Protein kinase C-binding protein NELL1 | NELL1 |
| Q92838 | Ectodysplasin-A, membrane form | EDA |
| Q92874 | Deoxyribonuclease-1-like 2 | DNASE1L2 |
| Q92876 | Kallikrein-6 | KLK6 |
| Q92913 | Fibroblast growth factor 13 | FGF13 |
| Q92954 | Proteoglycan 4 C-terminal part | PRG4 |
| Q93038 | Tumor necrosis factor receptor superfamily member 25 | TNFRSF25 |
| Q93091 | Ribonuclease K6 | RNASE6 |
| Q93097 | Protein Wnt-2b | WNT2B |
| Q93098 | Protein Wnt-8b | WNT8B |
| Q95460 | Major histocompatibility complex class I-related gene protein | MR1 |
| Q969D9 | Thymic stromal lymphopoietin | TSLP |
| Q969E1 | Liver-expressed antimicrobial peptide 2 | LEAP2 |
| Q969H8 | UPF0556 protein C19orf10 | C19orf10 |
| Q969Y0 | NXPE family member 3 | NXPE3 |
| Q96A54 | Adiponectin receptor protein 1 | ADIPOR1 |
| Q96A83 | Collagen alpha-1(XXVI) chain | EMID2 |
| Q96A84 | EMI domain-containing protein 1 | EMID1 |
| Q96A98 | Tuberoinfundibular peptide of 39 residues | PTH2 |
| Q96A99 | Pentraxin-4 | PTX4 |
| Q96BH3 | Epididymal sperm-binding protein 1 | ELSPBP1 |
| Q96BQ1 | Protein FAM3D | FAM3D |
| Q96CG8 | Collagen triple helix repeat-containing protein 1 | CTHRC1 |
| Q96DA0 | Zymogen granule protein 16 homolog B | ZG16B |
| Q96DN2 | von Willebrand factor C and EGF domain-containing protein | VWCE |
| Q96DR5 | BPI fold-containing family A member 2 | BPIFA2 |
| Q96DR8 | Mucin-like protein 1 | MUCL1 |
| Q96DX4 | RING finger and SPRY domain-containing protein 1 | RSPRY1 |
| Q96EE4 | Coiled-coil domain-containing protein 126 | CCDC126 |

TABLE 1-continued

Secreted Proteins

| Uniprot ID | Protein Name | Gene Name |
|---|---|---|
| Q96GS6 | Abhydrolase domain-containing protein FAM108A1 | FAM108A1 |
| Q96GW7 | Brevican core protein | BCAN |
| Q96HF1 | Secreted frizzled-related protein 2 | SFRP2 |
| Q96I82 | Kazal-type serine protease inhibitor domain-containing protein 1 | KAZALD1 |
| Q96ID5 | Immunoglobulin superfamily member 21 | IGSF21 |
| Q96II8 | Leucine-rich repeat and calponin homology domain-containing protein 3 | LRCH3 |
| Q96IY4 | Carboxypeptidase B2 | CPB2 |
| Q96JB6 | Lysyl oxidase homolog 4 | LOXL4 |
| Q96JK4 | HHIP-like protein 1 | HHIPL1 |
| Q96KN2 | Beta-Ala-His dipeptidase | CNDP1 |
| Q96KW9 | Protein SPACA7 | SPACA7 |
| Q96KX0 | Lysozyme-like protein 4 | LYZL4 |
| Q96L15 | Ecto-ADP-ribosyltransferase 5 | ART5 |
| Q96LB8 | Peptidoglycan recognition protein 4 | PGLYRP4 |
| Q96LB9 | Peptidoglycan recognition protein 3 | PGLYRP3 |
| Q96LC7 | Sialic acid-binding Ig-like lectin 10 | SIGLEC10 |
| Q96LR4 | Protein FAM19A4 | FAM19A4 |
| Q96MK3 | Protein FAM20A | FAM20A |
| Q96MS3 | Glycosyltransferase 1 domain-containing protein 1 | GLT1D1 |
| Q96NY8 | Processed poliovirus receptor-related protein 4 | PVRL4 |
| Q96NZ8 | WAP, kazal, immunoglobulin, kunitz and NTR domain-containing protein 1 | WFIKKN1 |
| Q96NZ9 | Proline-rich acidic protein 1 | PRAP1 |
| Q96P44 | Collagen alpha-1(XXI) chain | COL21A1 |
| Q96PB7 | Noelin-3 | OLFM3 |
| Q96PC5 | Melanoma inhibitory activity protein 2 | MIA2 |
| Q96PD5 | N-acetylmuramoyl-L-alanine amidase | PGLYRP2 |
| Q96PH6 | Beta-defensin 118 | DEFB118 |
| Q96PL1 | Secretoglobin family 3A member 2 | SCGB3A2 |
| Q96PL2 | Beta-tectorin | TECTB |
| Q96QH8 | Sperm acrosome-associated protein 5 | SPACA5 |
| Q96QR1 | Secretoglobin family 3A member 1 | SCGB3A1 |
| Q96QU1 | Protocadherin-15 | PCDH15 |
| Q96QV1 | Hedgehog-interacting protein | HHIP |
| Q96RW7 | Hemicentin-1 | HMCN1 |
| Q96S42 | Nodal homolog | NODAL |
| Q96S86 | Hyaluronan and proteoglycan link protein 3 | HAPLN3 |
| Q96SL4 | Glutathione peroxidase 7 | GPX7 |
| Q96SM3 | Probable carboxypeptidase X1 | CPXM1 |
| Q96T91 | Glycoprotein hormone alpha-2 | GPHA2 |
| Q99062 | Granulocyte colony-stimulating factor receptor | CSF3R |
| Q99102 | Mucin-4 alpha chain | MUC4 |
| Q99217 | Amelogenin, X isoform | AMELX |
| Q99218 | Amelogenin, Y isoform | AMELY |
| Q99435 | Protein kinase C-binding protein NELL2 | NELL2 |
| Q99470 | Stromal cell-derived factor 2 | SDF2 |
| Q99542 | Matrix metalloproteinase-19 | MMP19 |
| Q99574 | Neuroserpin | SERPINI1 |
| Q99584 | Protein S100-A13 | S100A13 |
| Q99616 | C-C motif chemokine 13 | CCL13 |
| Q99645 | Epiphycan | EPYC |
| Q99674 | Cell growth regulator with EF hand domain protein 1 | CGREF1 |
| Q99715 | Collagen alpha-1(XII) chain | COL12A1 |
| Q99727 | Metalloproteinase inhibitor 4 | TIMP4 |
| Q99731 | C-C motif chemokine 19 | CCL19 |
| Q99748 | Neurturin | NRTN |
| Q99935 | Proline-rich protein 1 | PROL1 |
| Q99942 | E3 ubiquitin-protein ligase RNF5 | RNF5 |
| Q99944 | Epidermal growth factor-like protein 8 | EGFL8 |
| Q99954 | Submaxillary gland androgen-regulated protein 3A | SMR3A |
| Q99969 | Retinoic acid receptor responder protein 2 | RARRES2 |
| Q99972 | Myocilin | MYOC |
| Q99983 | Osteomodulin | OMD |
| Q99985 | Semaphorin-3C | SEMA3C |
| Q99988 | Growth/differentiation factor 15 | GDF15 |
| Q9BPW4 | Apolipoprotein L4 | APOL4 |
| Q9BQ08 | Resistin-like beta | RETNLB |
| Q9BQ16 | Testican-3 | SPOCK3 |
| Q9BQ51 | Programmed cell death 1 ligand 2 | PDCD1LG2 |
| Q9BQB4 | Sclerostin | SOST |
| Q9BQI4 | Coiled-coil domain-containing protein 3 | CCDC3 |
| Q9BQP9 | BPI fold-containing family A member 3 | BPIFA3 |

TABLE 1-continued

Secreted Proteins

| Uniprot ID | Protein Name | Gene Name |
|---|---|---|
| Q9BQR3 | Serine protease 27 | PRSS27 |
| Q9BQY6 | WAP four-disulfide core domain protein 6 | WFDC6 |
| Q9BRR6 | ADP-dependent glucokinase | ADPGK |
| Q9BS86 | Zona pellucida-binding protein 1 | ZPBP |
| Q9BSG0 | Protease-associated domain-containing protein 1 | PRADC1 |
| Q9BSG5 | Retbindin | RTBDN |
| Q9BT30 | Probable alpha-ketoglutarate-dependent dioxygenase ABH7 | ALKBH7 |
| Q9BT56 | Spexin | C12orf39 |
| Q9BT67 | NEDD4 family-interacting protein 1 | NDFIP1 |
| Q9BTY2 | Plasma alpha-L-fucosidase | FUCA2 |
| Q9BU40 | Chordin-like protein 1 | CHRDL1 |
| Q9BUD6 | Spondin-2 | SPON2 |
| Q9BUN1 | Protein MENT | MENT |
| Q9BUR5 | Apolipoprotein O | APOO |
| Q9BV94 | ER degradation-enhancing alpha-mannosidase-like 2 | EDEM2 |
| Q9BWP8 | Collectin-11 | COLEC11 |
| Q9BWS9 | Chitinase domain-containing protein 1 | CHID1 |
| Q9BX67 | Junctional adhesion molecule C | JAM3 |
| Q9BX93 | Group XIIB secretory phospholipase A2-like protein | PLA2G12B |
| Q9BXI9 | Complement C1q tumor necrosis factor-related protein 6 | C1QTNF6 |
| Q9BXJ0 | Complement C1q tumor necrosis factor-related protein 5 | C1QTNF5 |
| Q9BXJ1 | Complement C1q tumor necrosis factor-related protein 1 | C1QTNF1 |
| Q9BXJ2 | Complement C1q tumor necrosis factor-related protein 7 | C1QTNF7 |
| Q9BXJ3 | Complement C1q tumor necrosis factor-related protein 4 | C1QTNF4 |
| Q9BXJ4 | Complement C1q tumor necrosis factor-related protein 3 | C1QTNF3 |
| Q9BXJ5 | Complement C1q tumor necrosis factor-related protein 2 | C1QTNF2 |
| Q9BXN1 | Asporin | ASPN |
| Q9BXP8 | Pappalysin-2 | PAPPA2 |
| Q9BXR6 | Complement factor H-related protein 5 | CFHR5 |
| Q9BXS0 | Collagen alpha-1(XXV) chain | COL25A1 |
| Q9BXX0 | EMILIN-2 | EMILIN2 |
| Q9BXY4 | R-spondin-3 | RSPO3 |
| Q9BY15 | EGF-like module-containing mucin-like hormone receptor-like 3 subunit beta | EMR3 |
| Q9BY50 | Signal peptidase complex catalytic subunit SEC11C | SEC11C |
| Q9BY76 | Angiopoietin-related protein 4 | ANGPTL4 |
| Q9BYF1 | Processed angiotensin-converting enzyme 2 | ACE2 |
| Q9BYJ0 | Fibroblast growth factor-binding protein 2 | FGFBP2 |
| Q9BYW3 | Beta-defensin 126 | DEFB126 |
| Q9BYX4 | Interferon-induced helicase C domain-containing protein 1 | IFIH1 |
| Q9BYZ8 | Regenerating islet-derived protein 4 | REG4 |
| Q9BZ76 | Contactin-associated protein-like 3 | CNTNAP3 |
| Q9BZG9 | Ly-6/neurotoxin-like protein 1 | LYNX1 |
| Q9BZJ3 | Tryptase delta | TPSD1 |
| Q9BZM1 | Group XIIA secretory phospholipase A2 | PLA2G12A |
| Q9BZM2 | Group IIF secretory phospholipase A2 | PLA2G2F |
| Q9BZM5 | NKG2D ligand 2 | ULBP2 |
| Q9BZP6 | Acidic mammalian chitinase | CHIA |
| Q9BZZ2 | Sialoadhesin | SIGLEC1 |
| Q9C0B6 | Protein FAM5B | FAM5B |
| Q9GZM7 | Tubulointerstitial nephritis antigen-like | TINAGL1 |
| Q9GZN4 | Brain-specific serine protease 4 | PRSS22 |
| Q9GZP0 | Platelet-derived growth factor D, receptor-binding form | PDGFD |
| Q9GZT5 | Protein Wnt-10a | WNT10A |
| Q9GZU5 | Nyctalopin | NYX |
| Q9GZV7 | Hyaluronan and proteoglycan link protein 2 | HAPLN2 |
| Q9GZV9 | Fibroblast growth factor 23 | FGF23 |
| Q9GZX9 | Twisted gastrulation protein homolog 1 | TWSG1 |
| Q9GZZ7 | GDNF family receptor alpha-4 | GFRA4 |
| Q9GZZ8 | Extracellular glycoprotein lacritin | LACRT |
| Q9H0B8 | Cysteine-rich secretory protein LCCL domain-containing 2 | CRISPLD2 |
| Q9H106 | Signal-regulatory protein delta | SIRPD |
| Q9H114 | Cystatin-like 1 | CSTL1 |

TABLE 1-continued

Secreted Proteins

| Uniprot ID | Protein Name | Gene Name |
|---|---|---|
| Q9H173 | Nucleotide exchange factor SIL1 | SIL1 |
| Q9H1E1 | Ribonuclease 7 | RNASE7 |
| Q9H1F0 | WAP four-disulfide core domain protein 10A | WFDC10A |
| Q9H1J5 | Protein Wnt-8a | WNT8A |
| Q9H1J7 | Protein Wnt-5b | WNT5B |
| Q9H1M3 | Beta-defensin 129 | DEFB129 |
| Q9H1M4 | Beta-defensin 127 | DEFB127 |
| Q9H1Z8 | Augurin | C2orf40 |
| Q9H239 | Matrix metalloproteinase-28 | MMP28 |
| Q9H2A7 | C-X-C motif chemokine 16 | CXCL16 |
| Q9H2A9 | Carbohydrate sulfotransferase 8 | CHST8 |
| Q9H2R5 | Kallikrein-15 | KLK15 |
| Q9H2X0 | Chordin | CHRD |
| Q9H2X3 | C-type lectin domain family 4 member M | CLEC4M |
| Q9H306 | Matrix metalloproteinase-27 | MMP27 |
| Q9H324 | A disintegrin and metalloproteinase with thrombospondin motifs 10 | ADAMTS10 |
| Q9H336 | Cysteine-rich secretory protein LCCL domain-containing 1 | CRISPLD1 |
| Q9H3E2 | Sorting nexin-25 | SNX25 |
| Q9H3R2 | Mucin-13 | MUC13 |
| Q9H3U7 | SPARC-related modular calcium-binding protein 2 | SMOC2 |
| Q9H3Y0 | Peptidase inhibitor R3HDML | R3HDML |
| Q9H4A4 | Aminopeptidase B | RNPEP |
| Q9H4F8 | SPARC-related modular calcium-binding protein 1 | SMOC1 |
| Q9H4G1 | Cystatin-9-like | CST9L |
| Q9H5V8 | CUB domain-containing protein 1 | CDCP1 |
| Q9H6B9 | Epoxide hydrolase 3 | EPHX3 |
| Q9H6E4 | Coiled-coil domain-containing protein 134 | CCDC134 |
| Q9H741 | UPF0454 protein C12orf49 | C12orf49 |
| Q9H772 | Gremlin-2 | GREM2 |
| Q9H7Y0 | Deleted in autism-related protein 1 | CXorf36 |
| Q9H8L6 | Multimerin-2 | MMRN2 |
| Q9H9S5 | Fukutin-related protein | FKRP |
| Q9HAT2 | Sialate O-acetylesterase | SIAE |
| Q9HB40 | Retinoid-inducible serine carboxypeptidase | SCPEP1 |
| Q9HB63 | Netrin-4 | NTN4 |
| Q9HBJ0 | Placenta-specific protein 1 | PLAC1 |
| Q9HC23 | Prokineticin-2 | PROK2 |
| Q9HC57 | WAP four-disulfide core domain protein 1 | WFDC1 |
| Q9HC73 | Cytokine receptor-like factor 2 | CRLF2 |
| Q9HC84 | Mucin-5B | MUC5B |
| Q9HCB6 | Spondin-1 | SPON1 |
| Q9HCQ7 | Neuropeptide NPSF | NPVF |
| Q9HCT0 | Fibroblast growth factor 22 | FGF22 |
| Q9HD89 | Resistin | RETN |
| Q9NNX1 | Tuftelin | TUFT1 |
| Q9NNX6 | CD209 antigen | CD209 |
| Q9NP55 | BPI fold-containing family A member 1 | BPIFA1 |
| Q9NP70 | Ameloblastin | AMBN |
| Q9NP95 | Fibroblast growth factor 20 | FGF20 |
| Q9NP99 | Triggering receptor expressed on myeloid cells 1 | TREM1 |
| Q9NPA2 | Matrix metalloproteinase-25 | MMP25 |
| Q9NPE2 | Neugrin | NGRN |
| Q9NPH0 | Lysophosphatidic acid phosphatase type 6 | ACP6 |
| Q9NPH6 | Odorant-binding protein 2b | OBP2B |
| Q9NQ30 | Endothelial cell-specific molecule 1 | ESM1 |
| Q9NQ36 | Signal peptide, CUB and EGF-like domain-containing protein 2 | SCUBE2 |
| Q9NQ38 | Serine protease inhibitor Kazal-type 5 | SPINK5 |
| Q9NQ76 | Matrix extracellular phosphoglycoprotein | MEPE |
| Q9NQ79 | Cartilage acidic protein 1 | CRTAC1 |
| Q9NR16 | Scavenger receptor cysteine-rich type 1 protein M160 | CD163L1 |
| Q9NR23 | Growth/differentiation factor 3 | GDF3 |
| Q9NR71 | Neutral ceramidase | ASAH2 |
| Q9NR99 | Matrix-remodeling-associated protein 5 | MXRA5 |
| Q9NRA1 | Platelet-derived growth factor C | PDGFC |
| Q9NRC9 | Otoraplin | OTOR |
| Q9NRE1 | Matrix metalloproteinase-26 | MMP26 |
| Q9NRJ3 | C-C motif chemokine 28 | CCL28 |
| Q9NRM1 | Enamelin | ENAM |
| Q9NRN5 | Olfactomedin-like protein 3 | OLFML3 |
| Q9NRR1 | Cytokine-like protein 1 | CYTL1 |
| Q9NS15 | Latent-transforming growth factor beta-binding protein 3 | LTBP3 |

TABLE 1-continued

Secreted Proteins

| Uniprot ID | Protein Name | Gene Name |
| --- | --- | --- |
| Q9NS62 | Thrombospondin type-1 domain-containing protein 1 | THSD1 |
| Q9NS71 | Gastrokine-1 | GKN1 |
| Q9NS98 | Semaphorin-3G | SEMA3G |
| Q9NSA1 | Fibroblast growth factor 21 | FGF21 |
| Q9NT22 | EMILIN-3 | EMILIN3 |
| Q9NTU7 | Cerebellin-4 | CBLN4 |
| Q9NVR0 | Kelch-like protein 11 | KLHL11 |
| Q9NWH7 | Spermatogenesis-associated protein 6 | SPATA6 |
| Q9NXC2 | Glucose-fructose oxidoreductase domain-containing protein 1 | GFOD1 |
| Q9NY56 | Odorant-binding protein 2a | OBP2A |
| Q9NY84 | Vascular non-inflammatory molecule 3 | VNN3 |
| Q9NZ20 | Group 3 secretory phospholipase A2 | PLA2G3 |
| Q9NZC2 | Triggering receptor expressed on myeloid cells 2 | TREM2 |
| Q9NZK5 | Adenosine deaminase CECR1 | CECR1 |
| Q9NZK7 | Group IIE secretory phospholipase A2 | PLA2G2E |
| Q9NZP8 | Complement C1r subcomponent-like protein | C1RL |
| Q9NZV1 | Cysteine-rich motor neuron 1 protein | CRIM1 |
| Q9NZW4 | Dentin sialoprotein | DSPP |
| Q9P0G3 | Kallikrein-14 | KLK14 |
| Q9P0W0 | Interferon kappa | IFNK |
| Q9P218 | Collagen alpha-1(XX) chain | COL20A1 |
| Q9P2C4 | Transmembrane protein 181 | TMEM181 |
| Q9P2K2 | Thioredoxin domain-containing protein 16 | TXNDC16 |
| Q9P2N4 | A disintegrin and metalloproteinase with thrombospondin motifs 9 | ADAMTS9 |
| Q9UBC7 | Galanin-like peptide | GALP |
| Q9UBD3 | Cytokine SCM-1 beta | XCL2 |
| Q9UBD9 | Cardiotrophin-like cytokine factor 1 | CLCF1 |
| Q9UBM4 | Opticin | OPTC |
| Q9UBP4 | Dickkopf-related protein 3 | DKK3 |
| Q9UBQ6 | Exostosin-like 2 | EXTL2 |
| Q9UBR5 | Chemokine-like factor | CKLF |
| Q9UBS5 | Gamma-aminobutyric acid type B receptor subunit 1 | GABBR1 |
| Q9UBT3 | Dickkopf-related protein 4 short form | DKK4 |
| Q9UBU2 | Dickkopf-related protein 2 | DKK2 |
| Q9UBU3 | Ghrelin-28 | GHRL |
| Q9UBV4 | Protein Wnt-16 | WNT16 |
| Q9UBX5 | Fibulin-5 | FBLN5 |
| Q9UBX7 | Kallikrein-11 | KLK11 |
| Q9UEF7 | Klotho | KL |
| Q9UFP1 | Protein FAM198A | FAM198A |
| Q9UGM3 | Deleted in malignant brain tumors 1 protein | DMBT1 |
| Q9UGM5 | Fetuin-B | FETUB |
| Q9UGP8 | Translocation protein SEC63 homolog | SEC63 |
| Q9UHF0 | Neurokinin-B | TAC3 |
| Q9UHF1 | Epidermal growth factor-like protein 7 | EGFL7 |
| Q9UHG2 | ProSAAS | PCSK1N |
| Q9UHI8 | A disintegrin and metalloproteinase with thrombospondin motifs 1 | ADAMTS1 |
| Q9UHL4 | Dipeptidyl peptidase 2 | DPP7 |
| Q9UI42 | Carboxypeptidase A4 | CPA4 |
| Q9UIG4 | Psoriasis susceptibility 1 candidate gene 2 protein | PSORS1C2 |
| Q9UIK5 | Tomoregulin-2 | TMEFF2 |
| Q9UIQ6 | Leucyl-cystinyl aminopeptidase, pregnancy serum form | LNPEP |
| Q9UJA9 | Ectonucleotide pyrophosphatase/phosphodiesterase family member 5 | ENPP5 |
| Q9UJH8 | Meteorin | METRN |
| Q9UJJ9 | N-acetylglucosamine-1-phosphotransferase subunit gamma | GNPTG |
| Q9UJW2 | Tubulointerstitial nephritis antigen | TINAG |
| Q9UK05 | Growth/differentiation factor 2 | GDF2 |
| Q9UK55 | Protein Z-dependent protease inhibitor | SERPINA10 |
| Q9UK85 | Dickkopf-like protein 1 | DKKL1 |
| Q9UKJ1 | Paired immunoglobulin-like type 2 receptor alpha | PILRA |
| Q9UKP4 | A disintegrin and metalloproteinase with thrombospondin motifs 7 | ADAMTS7 |
| Q9UKP5 | A disintegrin and metalloproteinase with thrombospondin motifs 6 | ADAMTS6 |
| Q9UKQ2 | Disintegrin and metalloproteinase domain-containing protein 28 | ADAM28 |
| Q9UKQ9 | Kallikrein-9 | KLK9 |

TABLE 1-continued

Secreted Proteins

| Uniprot ID | Protein Name | Gene Name |
|---|---|---|
| Q9UKR0 | Kallikrein-12 | KLK12 |
| Q9UKR3 | Kallikrein-13 | KLK13 |
| Q9UKU9 | Angiopoietin-related protein 2 | ANGPTL2 |
| Q9UKZ9 | Procollagen C-endopeptidase enhancer 2 | PCOLCE2 |
| Q9UL52 | Transmembrane protease serine 11E non-catalytic chain | TMPRSS11E |
| Q9ULC0 | Endomucin | EMCN |
| Q9ULI3 | Protein HEG homolog 1 | HEG1 |
| Q9ULZ1 | Apelin-13 | APLN |
| Q9ULZ9 | Matrix metalloproteinase-17 | MMP17 |
| Q9UM21 | Alpha-1,3-mannosyl-glycoprotein 4-beta-N-acetylglucosaminyltransferase A soluble form | MGAT4A |
| Q9UM22 | Mammalian ependymin-related protein 1 | EPDR1 |
| Q9UM73 | ALK tyrosine kinase receptor | ALK |
| Q9UMD9 | 97 kDa linear IgA disease antigen | COL17A1 |
| Q9UMX5 | Neudesin | NENF |
| Q9UN73 | Protocadherin alpha-6 | PCDHA6 |
| Q9UNA0 | A disintegrin and metalloproteinase with thrombospondin motifs 5 | ADAMTS5 |
| Q9UNI1 | Chymotrypsin-like elastase family member 1 | CELA1 |
| Q9UNK4 | Group IID secretory phospholipase A2 | PLA2G2D |
| Q9UP79 | A disintegrin and metalloproteinase with thrombospondin motifs 8 | ADAMTS8 |
| Q9UPZ6 | Thrombospondin type-1 domain-containing protein 7A | THSD7A |
| Q9UQ72 | Pregnancy-specific beta-1-glycoprotein 11 | PSG11 |
| Q9UQ74 | Pregnancy-specific beta-1-glycoprotein 8 | PSG8 |
| Q9UQC9 | Calcium-activated chloride channel regulator 2 | CLCA2 |
| Q9UQE7 | Structural maintenance of chromosomes protein 3 | SMC3 |
| Q9UQP3 | Tenascin-N | TNN |
| Q9Y223 | UDP-N-acetylglucosamine 2-epimerase | GNE |
| Q9Y240 | C-type lectin domain family 11 member A | CLEC11A |
| Q9Y251 | Heparanase 8 kDa subunit | HPSE |
| Q9Y258 | C-C motif chemokine 26 | CCL26 |
| Q9Y264 | Angiopoietin-4 | ANGPT4 |
| Q9Y275 | Tumor necrosis factor ligand superfamily member 13b, membrane form | TNFSF13B |
| Q9Y287 | BRI2 intracellular domain | ITM2B |
| Q9Y2E5 | Epididymis-specific alpha-mannosidase | MAN2B2 |
| Q9Y334 | von Willebrand factor A domain-containing protein 7 | VWA7 |
| Q9Y337 | Kallikrein-5 | KLK5 |
| Q9Y3B3 | Transmembrane emp24 domain-containing protein 7 | TMED7 |
| Q9Y3E2 | BolA-like protein 1 | BOLA1 |
| Q9Y426 | C2 domain-containing protein 2 | C2CD2 |
| Q9Y4K0 | Lysyl oxidase homolog 2 | LOXL2 |
| Q9Y4X3 | C-C motif chemokine 27 | CCL27 |
| Q9Y5C1 | Angiopoietin-related protein 3 | ANGPTL3 |
| Q9Y5I2 | Protocadherin alpha-10 | PCDHA10 |
| Q9Y5I3 | Protocadherin alpha-1 | PCDHA1 |
| Q9Y5K2 | Kallikrein-4 | KLK4 |
| Q9Y5L2 | Hypoxia-inducible lipid droplet-associated protein | HILPDA |
| Q9Y5Q5 | Atrial natriuretic peptide-converting enzyme | CORIN |
| Q9Y5R2 | Matrix metalloproteinase-24 | MMP24 |
| Q9Y5U5 | Tumor necrosis factor receptor superfamily member 18 | TNFRSF18 |
| Q9Y5W5 | Wnt inhibitory factor 1 | WIF1 |
| Q9Y5X9 | Endothelial lipase | LIPG |
| Q9Y625 | Secreted glypican-6 | GPC6 |
| Q9Y646 | Carboxypeptidase Q | CPQ |
| Q9Y6C2 | EMILIN-1 | EMILIN1 |
| Q9Y6F9 | Protein Wnt-6 | WNT6 |
| Q9Y6I9 | Testis-expressed sequence 264 protein | TEX264 |
| Q9Y6L7 | Tolloid-like protein 2 | TLL2 |
| Q9Y6N3 | Calcium-activated chloride channel regulator family member 3 | CLCA3P |
| Q9Y6N6 | Laminin subunit gamma-3 | LAMC3 |
| Q9Y6R7 | IgGFc-binding protein | FCGBP |
| Q9Y6Y9 | Lymphocyte antigen 96 | LY96 |
| Q9Y6Z7 | Collectin-10 | COLEC10 |

The Uniprot IDs set forth in Table 1 refer to the human versions the listed proteins and the sequences of each are available from the Uniprot database. Sequences of the listed proteins are also generally available for various animals, including various mammals and animals of veterinary or industrial interest. Accordingly, in some embodiments, compositions and methods of the invention provide for the delivery of one or more mRNAs encoding one or more proteins chosen from mammalian homologs or homologs from an animal of veterinary or industrial interest of the secreted proteins listed in Table 1; thus, compositions of the invention may comprise an mRNA encoding a protein chosen from mammalian homologs or homologs from an animal of veterinary or industrial interest of a protein listed in Table 1 along with other components set out herein, and methods of the invention may comprise preparing and/or administering a composition comprising an mRNA encoding a protein chosen from mammalian homologs or homologs from an animal of veterinary or industrial interest of a protein listed in Table 1 along with other components set out herein. In some embodiments, mammalian homologs are chosen from mouse, rat, hamster, gerbil, horse, pig, cow, llama, alpaca, mink, dog, cat, ferret, sheep, goat, or camel homologs. In some embodiments, the animal of veterinary or industrial interest is chosen from the mammals listed above and/or chicken, duck, turkey, salmon, catfish, or tilapia.

In some embodiments, the compositions and methods of the invention provide for the delivery of one or more mRNAs encoding one or more additional exemplary proteins listed in Table 2; thus, compositions of the invention may comprise an mRNA encoding a protein listed in Table 2 (or a homolog thereof, as discussed below) along with other components set out herein, and methods of the invention may comprise preparing and/or administering a composition comprising an mRNA encoding a protein chosen from the proteins listed in Table 2 (or a homolog thereof, as discussed below) along with other components set out herein.

TABLE 2

Additional Exemplary Proteins

| Uniprot ID | Protein Name | Gene Name |
| --- | --- | --- |
| A6NGW2 | Putative stereocilin-like protein | STRCP1 |
| A6NIE9 | Putative serine protease 29 | PRSS29P |
| A6NJ16 | Putative V-set and immunoglobulin domain-containing-like protein IGHV4OR15-8 | IGHV4OR15-8 |
| A6NJS3 | Putative V-set and immunoglobulin domain-containing-like protein IGHV1OR21-1 | IGHV1OR21-1 |
| A6NMY6 | Putative annexin A2-like protein | ANXA2P2 |
| A8MT79 | Putative zinc-alpha-2-glycoprotein-like 1 | |
| A8MWS1 | Putative killer cell immunoglobulin-like receptor like protein KIR3DP1 | KIR3DP1 |
| A8MXU0 | Putative beta-defensin 108A | DEFB108P1 |
| C9JUS6 | Putative adrenomedullin-5-like protein | ADM5 |
| P0C7V7 | Putative signal peptidase complex catalytic subunit SEC11B | SEC11B |
| P0C854 | Putative cat eye syndrome critical region protein 9 | CECR9 |
| Q13046 | Putative pregnancy-specific beta-1-glycoprotein 7 | PSG7 |
| Q16609 | Putative apolipoprotein(a)-like protein 2 | LPAL2 |
| Q2TV78 | Putative macrophage-stimulating protein MSTP9 | MST1P9 |
| Q5JQD4 | Putative peptide YY-3 | PYY3 |
| Q5R387 | Putative inactive group IIC secretory phospholipase A2 | PLA2G2C |
| Q5VSP4 | Putative lipocalin 1-like protein 1 | LCN1P1 |
| Q5W188 | Putative cystatin-9-like protein CST9LP1 | CST9LP1 |
| Q6UXR4 | Putative serpin A13 | SERPINA13P |
| Q86SH4 | Putative testis-specific prion protein | PRNT |
| Q86YQ2 | Putative latherin | LATH |
| Q8IVG9 | Putative humanin peptide | MT-RNR2 |
| Q8NHM4 | Putative trypsin-6 | TRY6 |

TABLE 2-continued

Additional Exemplary Proteins

| Uniprot ID | Protein Name | Gene Name |
| --- | --- | --- |
| Q8NHW4 | C-C motif chemokine 4-like | CCL4L2 |
| Q9H7L2 | Putative killer cell immunoglobulin-like receptor-like protein KIR3DX1 | KIR3DX1 |
| Q9NRI6 | Putative peptide YY-2 | PYY2 |
| Q9UF72 | Putative TP73 antisense gene protein 1 | TP73-AS1 |
| Q9UKY3 | Putative inactive carboxylesterase 4 | CES1P1 |

The Uniprot IDs set forth in Table 2 refer to the human versions the listed putative proteins and the sequences of each are available from the Uniprot database. Sequences of the listed proteins are also available for various animals, including various mammals and animals of veterinary or industrial interest. Accordingly, in some embodiments, compositions and methods of the invention provide for the delivery of one or more mRNAs encoding a protein chosen from mammalian homologs or homologs from an animal of veterinary or industrial interest of a protein listed in Table 2; thus, compositions of the invention may comprise an mRNA encoding a protein chosen from mammalian homologs or homologs from an animal of veterinary or industrial interest of a protein listed in Table 2 along with other components set out herein, and methods of the invention may comprise preparing and/or administering a composition comprising an mRNA encoding a protein chosen from mammalian homologs or homologs from an animal of veterinary or industrial interest of a protein listed in Table 2 along with other components set out herein. In some embodiments, mammalian homologs are chosen from mouse, rat, hamster, gerbil, horse, pig, cow, llama, alpaca, mink, dog, cat, ferret, sheep, goat, or camel homologs. In some embodiments, the animal of veterinary or industrial interest is chosen from the mammals listed above and/or chicken, duck, turkey, salmon, catfish, or tilapia.

In embodiments, the compositions and methods of the invention provide for the delivery of mRNA encoding a lysosomal protein chosen from Table 3. In some embodiments, the compositions and methods of the invention provide for the delivery of one or more mRNAs encoding one or more lysosomal and/or related proteins listed in Table 3; thus, compositions of the invention may comprise an mRNA encoding a protein listed in Table 3 (or a homolog thereof, as discussed below) along with other components set out herein, and methods of the invention may comprise preparing and/or administering a composition comprising an mRNA encoding a protein chosen from the proteins listed in Table 3 (or a homolog thereof, as discussed below) along with other components set out herein.

TABLE 3

Lysosomal and Related Proteins

α-fucosidase
α-galactosidase
α-glucosidase
α-Iduronidase
α-mannosidase
α-N-acetylgalactosaminidase (α-galactosidase B)
β-galactosidase
β-glucuronidase
β-hexosaminidase
β-mannosidase
3-hydroxy-3-methylglutaryl-CoA (HMG-CoA) lyase
3-methylcrotonyl-CoA carboxylase

TABLE 3-continued

Lysosomal and Related Proteins

3-O-sulfogalactosyl cerebroside sulfatase (arylsulfatase A)
acetyl-CoA transferase
acid alpha-glucosidase
acid ceramidase
acid lipase
acid phosphatase
acid sphingomyelinase
alpha-galactosidase A
arylsulfatase A
beta-galactosidase
beta-glucocerebrosidase
beta-hexosaminidase
biotinidase
cathepsin A
cathepsin K
CLN3
CLN5
CLN6
CLN8
CLN9
cystine transporter (cystinosin)
cytosolic protein beta3A subunit of the adaptor protein-3 complex, AP3
formyl-Glycine generating enzyme (FGE)
galactocerebrosidase
galactose-1-phosphate uridyltransferase (GALT)
galactose 6-sulfate sulfatase
(also known as N-acetylgalactosamine-6-sulfatase)
glucocerebrosidase
glucuronate sulfatase
glucuronidase
glycoprotein cleaving enzymes
glycosaminoglycan cleaving enzymes
glycosylasparaginase (aspartylglucosaminidase)
GM2-AP
Heparan-alpha-glucosaminide N-acetyltransferase (HGSNAT, TMEM76)
Heparan sulfatase
hexosaminidase A lysosomal proteases methylmalonyl-CoA mutase
hyaluronidase
Iduronate sulfatase
LAMP-2
lysosomal α-mannosidase
Lysosomal p40 (C2orf18)
Major facilitator superfamily domain containing 8 protein (MFSD8 or CLN7)
N-acetylgalactosamine 4-sulfatase
N-acetyl glucosamine 6-sulfatase
N-acetyl glucosaminidase
N-acetylglucosamine-1-phosphate transferase
NPC1
NPC2
palmitoyl-protein thioesterase
palmitoyl-protein thioesterase (CLN1)
Saposin A (Sphingolipid activator protein A)
Saposin B (Sphingolipid activator protein B)
Saposin C (Sphingolipid activator protein C)
Saposin D (Sphingolipid activator protein D)
sialic acid transporter (sialin)
sialidase
Sialin
sulfatase

TABLE 3-continued

Lysosomal and Related Proteins

Transmembrane protein 74 (TMEM74)
tripeptidyl-peptidase
tripeptidyl-peptidase I (CLN2)
UDP-N-acetylglucosamine-phosphotransferase Information regarding lysosomal proteins is available from Lubke et al., "Proteomics of the Lysosome," *Biochim Biophys Acta*. (2009) 1793: 625-635. In some embodiments, the protein listed in Table 3 and encoded by mRNA in the compositions and methods of the invention is a human protein. Sequences of the listed proteins are also available for various animals, including various mammals and animals of veterinary or industrial interest. Accordingly, in some embodiments, compositions and methods of the invention provide for the delivery of one or more mRNAs encoding a protein chosen from mammalian homologs or homologs from an animal of veterinary or industrial interest of a protein listed in Table 3; thus, compositions of the invention may comprise an mRNA encoding a protein chosen from mammalian homologs or homologs from an animal of veterinary or industrial interest of a protein listed in Table 3 along with other components set out herein, and methods of the invention may comprise preparing and/or administering a composition comprising an mRNA encoding a protein chosen from mammalian homologs or homologs from an animal of veterinary or industrial interest of a protein listed in Table S3 along with other components set out herein. In some embodiments, mammalian homologs are chosen from mouse, rat, hamster, gerbil, horse, pig, cow, llama, alpaca, mink, dog, cat, ferret, sheep, goat, or camel homologs. In some embodiments, the animal of veterinary or industrial interest is chosen from the mammals listed above and/or chicken, duck, turkey, salmon, catfish, or tilapia.

In some embodiments, the compositions and methods of the invention provide for the delivery of mRNA encoding a therapeutic protein (e.g., cytosolic, transmembrane or secreted) such as those listed in Table 4. In some embodiments, the compositions and methods of the invention provide for the delivery of an mRNA encoding a therapeutic protein useful in treating a disease or disorder (i.e., indication) listed in Table 4; thus, compositions of the invention may comprise an mRNA encoding a therapeutic protein listed or not listed in Table 4 (or a homolog thereof, as discussed below) along with other components set out herein for treating a disease or disorder (i.e., indication) listed in Table 4, and methods of the invention may comprise preparing and/or administering a composition comprising an mRNA encoding a such a protein (or a homolog thereof, as discussed below) along with other components set out herein for treatment of a disease or disorder listed in Table 4.

TABLE 4

Exemplary Indications and Related Proteins

| Indication | Therapeutic Protein |
|---|---|
| 3-Methylcrotonyl-CoA carboxylase deficiency | Methylcrotonoyl-CoA carboxylase |
| 3-Methylglutaconic aciduria | Methylglutaconyl-CoA hydratase |
| Actinic keratosis | |
| Acute intermittent porphyria | Porphobilinogen deaminase |
| Acute lymphocytic leukemia | |
| Acute myeloid leukemia | |
| Addison's disease | |

TABLE 4-continued

Exemplary Indications and Related Proteins

| Indication | Therapeutic Protein |
|---|---|
| Adenosine deaminase deficiency | Adenosine deaminase |
| Adrenoleukodystrophy | ABCD1 |
| Adrenomyeloneuropathy | |
| AIDS/HIV | |
| Alcohol use disorders | |
| Alkaptonuria | Homogentisate 1,2-dioxygenase |
| Allergic asthma | Anti-IgE mAb |
| Allergies (dermatitis, rhinitis) | |
| Alopecia areata | |
| Alpers' disease | POLG |
| Alpers-Huttenlocher syndrome | |
| Alpha 1-antitrypsin deficiency | Alpha 1 protease inhibitor |
| Alpha-mannosidosis | Alpha-D-mannosidase |
| Alport syndrome | |
| Alzheimer's disease | |
| Amyloid light-chain amyloidosis | |
| Amyotrophic lateral sclerosis (ALS) | |
| Anemia | Erythropoietin |
| Aortic valve stenosis | |
| Argininemia | Arginase |
| Argininosuccinic acidemia | Argininosuccinate lyase |
| Arrhythmogenic right ventricular dysplasia | |
| Autism | |
| Autosomal dominant and recessive progressive external ophthalmoplegia with mitochondrial DNA deletions | |
| Autosomal recessive polycystic kidney disease | ARPKD |
| Bacterial infections | |
| Basal cell carcinoma | |
| Batten disease | Battenin + others |
| B-cell chronic lymphocytic leukemia | |
| Becker muscular dystrophy | Dystrophin |
| Beta-thalassemia | Beta globin |
| Binge eating disorder | |
| Bipolar disorder | |
| Bladder cancer | |
| Blepharospasm, Cervical dystonia, Chronic migraine, more | Botulinum toxin |
| Bronchiolitis obliterans | |
| Brugada syndrome | |
| Buerger's disease | |
| CACNA1A | |
| CACNB4-related Episodic Ataxia Type 2 | |
| Cancer and depression | |
| Cancer and sexual dysfunction | |
| Cancer in pregnancy | |
| Carbamylphosphate synthetase deficiency | Carbamylphosphate synthetase |
| Carcinoma of the gallbladder | |
| Cardiomyopathy (diabetic) | |
| Cardiomyopathy (hypertrophic) | |
| Carnitine uptake defect | SLC22A5 |
| Catecholaminergic polymorphic ventricular tachycardia | |
| CDKL5-related Atypical Rett Syndrome | |
| Celiac disease | |
| Cellulitis | |
| Cerebrovascular disease | |
| Cervix uteri cancer | |
| Chronic fatigue syndrome | |
| Chronic graft versus host disease | |
| Chronic idiopathic urticaria | |
| Chronic immune thrombocytopenia | Thrombopoietin |
| Chronic kidney kisease | |
| Chronic liver disease | |
| Chronic lymphocytic leukemia | |
| Chronic myeloid leukemia | |
| Chronic pancreatitis | |
| Cirrhosis of the liver | |
| Citrullinemia, type I | Argininosuccinate synthase |
| Classic Rett Syndrome | |
| Classical galactosemia | Galactose-1-phosphate uridylyltransferase |
| Clostridium difficile associated diarrhea | |
| Clotting disorders | |
| COAD/COPD | |
| Cocaine addiction | |
| COL4A5-related disorders | |

TABLE 4-continued

Exemplary Indications and Related Proteins

| Indication | Therapeutic Protein |
|---|---|
| Cold contact urticaria | |
| Contraception, female | |
| Coronary artery diseases | |
| Corpus uteri cancer | |
| Corticobasal degeneration | |
| Crigler-Najjar syndrome | UDP-glucuronosyltransferase |
| Critical limb ischemia | |
| CTNS-related cystinosis | |
| Cutaneous lupus erythematosus | |
| Cutaneous neuroendocrine carcinoma (Merkel Cell) | |
| Cystic fibrosis | CFTR |
| Cystic fibrosis | Deoxyribonuclease I |
| Cystinosis | Cystinosin |
| Cystinuria | SLC7A9 |
| Dementia (Lewy body) | |
| Depression | |
| Diabetic foot infections | |
| Diabetic foot ulcer | |
| Diabetic peripheral neuropathy | |
| Diabetic ulcers | |
| Diarrhoeal diseases | |
| Diffuse large B-cell lymphoma | |
| DiGeorge syndrome | |
| Diverticulitis | |
| Drug use disorders | |
| Duchenne muscular dystrophy | Dystrophin |
| Dysarthria | |
| Dyskinesia (levodopa-induced) | |
| Early-onset autosomal dominant Alzheimer's disease | |
| Eczema | |
| Ehlers-Danlos syndrome, type 1 | |
| EIF2B1 | |
| EIF2B2 | |
| EIF2B3 | |
| EIF2B4 | |
| EIF2B5-related childhood ataxia with central nervous system hypomyelination/vanishing white matter | |
| Eosinophilic esophagitis | |
| Epilepsy | |
| Erectile dysfunction | |
| Erythropoietic protoporphyria | Ferrochelatase |
| Esophageal carcinoma | |
| Essential tremor | |
| Fabry disease | Alpha galactosidase |
| Familial adenomatous polyposis | APC |
| Familial chylomicronemia | Lipoprotein lipase |
| Familial dysbetalipoproteinemia | Apolipoprotein E |
| Familial isolated dilated cardiomyopathy | |
| Familial mediterranean fever | Pyrin (MEFV) |
| Familial melanoma | |
| Female infertility | Follicle stimulating hormone |
| Female sexual dysfunction | |
| Fibromyalgia | |
| FMR1-related disorders | |
| Fracture healing | |
| Fragile X Premature Ovarian Failure Syndrome | |
| Fragile X syndrome | FMRP |
| Fragile X-Associated Tremor/Ataxia Syndrome | |
| Friedreich's ataxia | |
| Frontotemporal dementia | |
| Fryns syndrome | |
| Galactocerebrosidase deficiencies | |
| GALE deficiency | Galactose epimerase |
| GALK deficiency | Galactokinase |
| GALT-related galactosemia | |
| Gastric cancer | |
| Gastroesophageal reflux disease | |
| Gaucher disease | Glucocerebrosidase |
| Gilbert syndrome | UDP-glucuronosyltransferase |
| Glioblastoma multiforme | |
| Glomerulonephritis | |
| Glutaric acidemia, type I | Glutaryl-CoA dehydrogenase |
| GM2 gangliosidosis | HEXA, HEXB |
| Gout | Urate oxidase |
| Graft versus host disease | |

TABLE 4-continued

Exemplary Indications and Related Proteins

| Indication | Therapeutic Protein |
|---|---|
| Growth hormone deficiency | Growth hormone 1/Growth hormone 2 |
| Head and neck cancer, Metastatic colorectal cancer | Anti-EGFr mAb |
| Hearing loss, adult onset | |
| Heart failure | |
| Hemachromatosis | HFE protein |
| Hemifacial spasm | |
| Hemolytic uremic syndrome | Anti-complement factor C5 mAb |
| Hemophilia A | Factor VIII |
| Hemophilia A, Hemophilia B | Factor VII |
| Hemophilia B | Factor IX |
| Hepatitis B, Hepatitis C | Interferon alpha |
| HER2+ breast cancer, gastric cancer | Anti-HER2 mAb |
| Hereditary angioedema | C1 esterase inhibitor |
| Hereditary hemorrhagic telangiectasia | |
| Hereditary hemorrhagic telangiectasia (AT) | |
| Hereditary spherocytosis | |
| Hidradenitis suppurativa | |
| Homocystinuria | Cystathionine beta-synthase |
| Homozygous familial hypercholesterolemia | LDL receptor |
| Hunter syndrome (MPS II) | Iduronate-2-sulfatase |
| Huntington disease | Huntingtin |
| Hurler syndrome (MPS I) | Alpha-L iduronidase |
| Hydrolethalus | |
| Hyperalgesia | |
| Hyperbilirubinemia | |
| Hyperhidrosis | |
| Hyperlipidemia | |
| Hypermethioninemia | Methionine adenosyltransferase |
| Hyperoxaluria, type I | Serine-pyruvate aminotransferase |
| Hypertension | |
| Hyperuricemia | |
| Hyponatremia | |
| Hypoparathyroidism | Parathyroid hormone |
| Hypophosphatasia | TNSALP |
| Idiopathic pulmonary fibrosis | |
| Iminoglycinuria | |
| Immunoglobulin deficiency | Immunoglobulin |
| Infection (adenovirus) | |
| Infection (anthrax prophylaxis) | |
| Infection (BK virus) | |
| Infection (Clostridium difficile prophylaxis) | |
| Infection (Dengue fever prophylaxis) | |
| Infection (Epstein-Barr virus) | |
| Infection (Hepatitis-D) | |
| Infection (Lyme disease prophylaxis) | |
| Infection (Smallpox virus) | |
| Infectious diseases vaccines | Infectious antigen |
| Inflammatory heart diseases | |
| Insomnia | |
| Interstitial cystitis | |
| Iron-deficiency anaemia | |
| Irritable bowel disease | |
| Ischaemic heart disease | |
| Isovaleric aciduria | Isovaleric acid CoA dehydrogenase deficiency |
| Jansky-Bielschowsky disease | |
| Juvenile Batten disease | |
| Juvenile Neuronal Ceroid Lipofuscinosis (JNCL) | |
| Juvenile rheumatoid arthritis | TNF-alpha inhibitors |
| Kennedy's disease (SBMA) | |
| Keratoconus | |
| Krabbe disease | Galactocerebrosidase |
| Leber's hereditary optic neuropathy | NADH dehydrogenase |
| Leiomyosarcoma | |
| Lennox-Gastaut syndrome | |
| Lesch-Nyhan syndrome | Hypoxanthine phosphoribosyltransferase 1 |
| Leukaemia | |
| Li-Fraumeni syndrome | TP53 |
| Lipoma | |
| Liposarcoma | |
| Liver cancer | |
| Long-chain 3-OH acyl-CoA dehydrogenase deficiency | Long-chain-3-hydroxyacyl-CoA dehydrogenase |
| Lower respiratory infections | |
| Lysosomal acid lipase deficiency | Lysosomal acid lipase |
| Macular degeneration | |
| Major depressive disorder | |

TABLE 4-continued

Exemplary Indications and Related Proteins

| Indication | Therapeutic Protein |
|---|---|
| Malignant fibrous histiocytoma | |
| Mantle cell lymphoma | |
| Maple syrup urine disease | 3-methyl-2-oxobutanoate dehydrogenase |
| Marfan syndrome | FBN1 |
| Maroteaux-Lamy syndrome (MPS VI) | N-acetylgalactosamine 4-sulfatase |
| Mastocytosis | |
| McArdle disease | Muscle glycogen phosphorylase |
| MECP2-related disorders | |
| MECP2-related Severe Neonatal Encephalopathy | |
| Medium-chain acyl-CoA dehydrogenase deficiency | Acyl-CoA dehydrogenase |
| Melanoma | Anti-CTLA4 mAb |
| Metachromatic leukodystrophy | Arylsulfatase A |
| Metastatic colorectal cancer, NSCLC, others | Anti-VEGF mAb |
| Methylmalonyl-CoA mutase deficiency | Methylmalonyl-CoA mutase |
| Migraine | |
| Mitochondrial oxidative phosphorylation disorders | |
| Morquio syndrome, type A (MPS IVA) | Galactose 6-sulfate sulfatase |
| Morquio syndrome, type B (MPS IVB) | Beta-galactosidase |
| Mouth and oropharynx cancers | |
| Multiple carboxylase deficiency | Biotin-methylcrotonoyl-CoA-carboxylase ligase |
| Multiple myeloma | |
| Multiple sclerosis | Anti-VLA-4 mAb |
| Multiple sclerosis | Interferon beta |
| Multiple system atrophy | |
| Myasthenia gravis | |
| Myelofibrosis | |
| Narcolepsy | |
| Neonatal bronchopulmonary dysplasia | |
| Neonatal infections | |
| Nephritis and nephrosis | |
| Neurofibromatosis, type 1 | NF-1 |
| Neuronal ceroid lipofuscinoses-related diseases | |
| Neutropenia | G-CSF |
| Niemann Pick disease, type A/B | SMPD1 |
| Niemann Pick disease, type C | NPC1 |
| Niemann-Pick disease Type C1 | |
| Nocturia | |
| Non-alcoholic fatty liver disease | |
| Non-Hodgkin lymphoma | Anti-CD20 mAb |
| Non-small cell lung cancer | |
| Notch-3 related cerebral autosomal dominant arteriopathy with subcortical infarcts and leukoencephalopathy (CADASIL) | |
| Obesity | |
| Ophthalmoparesis | |
| Opioid induced constipation | |
| Ornithine transcarbamylase deficiency | Ornithine transcarbamylase |
| Osteoarthritis | |
| Osteopetrosis | |
| Osteoporosis | Anti-RANKL mAb |
| Ovarian cancer | |
| Paget disease of bone | Sequestosome 1 |
| Pain | |
| Pancreatic carcinoma | |
| Panic disorder | |
| Parkinson disease | |
| Paroxysmal nocturnal hemoglobinuria | Anti-complement factor C5 Mab |
| Pediculosis capitis (head lice) | |
| Pelizaeus-Merzbacher disease | |
| Pemphigus vulgaris | |
| Peptic ulcer disease | |
| Peripheral neuropathy | |
| Peyronie's disease | |
| Phenylketonuria | Phenylalanine hydroxylase |
| Pneumococcal infection prophylaxis | |
| POLG-related sensory ataxic neuropathy | |
| Polycystic kidney disease | |
| Polycystic ovary syndrome | |
| Polycythaemia vera | |
| Polymerase G-related disorders | |
| Polymorphous light eruption | |
| Pompe disease | Alpha glucosidase |
| Porphyria cutanea tarda | Uroporphyrinogen decarboxylase |
| Post herpetic neuralgia | |
| Post-organ transplant | |
| Pouchitis | |

TABLE 4-continued

Exemplary Indications and Related Proteins

| Indication | Therapeutic Protein |
|---|---|
| PPM-X Syndrome | |
| Prader-Willi syndrome | |
| Preeclampsia | |
| Premature ejaculation | |
| Prematurity and low birth weight | |
| Primary ciliary dyskinesia | |
| Primary glomerular diseases | |
| Primary humoral immune deficiencies (e.g., CVID) | Immunoglobulin |
| Proctitis | |
| Progressive multifocal leukoencephalopathy | |
| Progressive supranuclear palsy | |
| Propionic acidemia | Propionyl-CoA carboxylase |
| Prostate cancer | |
| Psoriasis | Anti-IL-12 & IL-23 mAb |
| Psoriatic arthritis | TNF-alpha inhibitors |
| PTT-1 | |
| Pulmonary arterial hypertension | |
| Pulmonary arterial hypertension | |
| Raynaud's phenomenon | |
| Refractive errors | |
| Renal cell carcinoma | |
| Restless leg syndrome | |
| Retinitis pigmentosa | |
| Rheumatic heart disease | |
| Rheumatoid arthritis | Anti-interleukin-6 (IL-6) mAb |
| Rheumatoid arthritis | T-cell costimulation blocker |
| Rheumatoid arthritis | TNF-alpha inhibitor |
| Romano-Ward syndrome | |
| Rosacea | |
| Sanfilippo syndrome, type A (MPS IIIA) | Heparan N-sulfatase |
| Sanfilippo syndrome, type B (MPS IIIB) | N-acetyl-alpha-D-glucosaminidase |
| Santavuori-Haltia disease | |
| Schizophrenia | |
| Schnitzler syndrome | |
| Scleroderma | |
| SCN1A | |
| SCN1B-related seizure disorders | |
| Short-chain acyl-CoA dehydrogenase deficiency | Butyryl-CoA dehydrogenase |
| Sickle cell disease | Hemoglobin |
| SLC3A1-related disorders | |
| Small cell lung cancer | |
| SMN-1-related spinal muscular atrophy (SMA) | |
| Spinal muscular atrophy | Survival motor neuron protein |
| Squamous cell carcinoma of head and neck | |
| Stickler syndrome | |
| Stomach cancer | |
| Stroke prophylaxis | |
| Synovial sarcoma | |
| Systemic lupus erythematosus | Anti-BAFF |
| Systemic sclerosis | |
| Tetrahydrobiopterin-deficient hyperphenylalaninemia | Tetrahydrobiopterin |
| Thromboangiitis obliterans | |
| Thrombotic disorders | |
| Thyroid cancer | |
| TPP1 deficiencies | |
| Trachea, bronchus, lung cancers | |
| Tricuspid atresia | |
| TSC1 | |
| TSC2-related tuberous sclerosis | |
| Type 2 diabetes mellitus | Glucagon-like peptide 1 (GLP-1) agonist |
| Type 2 diabetes mellitus | Insulin |
| Tyrosinemia, type I | Fumarylacetoacetase |
| Ulcerative colitis | |
| Uterine fibroids | |
| Varicose veins | |
| Venous thromboembolism | |
| Very long-chain acyl-CoA dehydrogenase deficiency | Long-chain-acyl-CoA dehydrogenase |
| von Gierke's disease | Glucose-6-phosphatase |
| Von Hippel-Lindau disease | pVHL |
| Wegener granulomatosis | |
| Wilson disease | Wilson disease protein |
| X-Linked adrenal hypoplasia | |
| X-linked adrenoleukodystrophy | |
| X-linked agammaglobulinemia | Bruton's tyrosine kinase |

In some embodiments, one or more therapeutic proteins of the current invention are selected from Table 1, 2, 3 or 4. In some specific embodiments, one or more therapeutic proteins are selected from the group consisting of alpha galactosidase, erythropoietin, α1-antitrypsin, carboxypeptidase N, alpha-L-iduronidase, iduronate-2-sulfatase, N-acetylglucosamine-1-phosphate transferase, N-acetylglucosaminidase, lysosomal acid lipase, arylsulfatase-A alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase, galactocerebrosidase, human growth hormone, ornithine transcarbamylase (OTC), carbamyl phosphate synthetase-1 (CPS1), argininosuccinate synthetase-1 (ASS1), argininosuccinate lyase (ASL), arginase-1 (ARG1), cystic fibrosis transmembrane conductance regulator (CFTR), Factor VII, Factor VIII, Factor IX, heparan-N-sulfatase, and combinations thereof.

In some embodiments, the present invention is used to prevent, treat and/or cure a subject affected with a disease or disorder listed or associated with the proteins listed in Tables 1, 2, 3 or 4. Diseases or disorders for which the compositions and methods of the invention may be employed include, but are not limited to, disorders such as SMN1-related spinal muscular atrophy (SMA), amyotrophic lateral sclerosis (ALS), GALT-related galactosemia, Cystic Fibrosis (CF), SLC3A1-related disorders, cystinuria, COL4A5-related disorders, Alport syndrome, galactocerebrosidase deficiencies, X-linked adrenoleukodystrophy, adrenomyeloneuropathy, Friedreich's ataxia, Pelizaeus-Merzbacher disease, TSC1 or TSC2-related tuberous sclerosis, Sanfilippo B syndrome (MPS IIIB), CTNS-related cystinosis, the FMR1-related disorders, include Fragile X syndrome, Fragile X-Associated Tremor/Ataxia Syndrome, Fragile X Premature Ovarian Failure Syndrome, Prader-Willi syndrome, Fabry disease, hereditary hemorrhagic telangiectasia (AT), Niemann-Pick disease Type C1, neuronal ceroid lipofuscinoses-related diseases, Juvenile Neuronal Ceroid Lipofuscinosis (JNCL), Juvenile Batten disease, Santavuori-Haltia disease, Jansky-Bielschowsky disease, PTT-1 deficiency, TPP1 deficiency, EIF2B1, EIF2B2, EIF2B3, EIF2B4 and EIF2B5-related childhood ataxia with central nervous system hypomyelination/vanishing white matter, CACNA1A and CACNB4-related Episodic Ataxia Type 2, the MECP2-related disorders, Classic Rett Syndrome, MECP2-related Severe Neonatal Encephalopathy, PPM-X Syndrome, CDKL5-related Atypical Rett Syndrome, Kennedy's disease (SBMA), Notch-3 related cerebral autosomal dominant arteriopathy with subcortical infarcts and leukoencephalopathy (CADASIL), SCN1A and SCN1B-related seizure disorders, Polymerase G-related disorders, Alpers-Huttenlocher syndrome, POLG-related sensory ataxic neuropathy, dysarthria, ophthalmoparesis, autosomal dominant and recessive progressive external ophthalmoplegia with mitochondrial DNA deletions, X-Linked adrenal hypoplasia, X-linked agammaglobulinemia, Wilson's disease, and blood clotting disorders.

In certain embodiments, the mRNA used in the compositions and methods of the invention may encode an antibody. In some embodiments, the mRNA may encode a protein that is made up of subunits that are encoded by more than one gene. For example, the protein may be a heterodimer, wherein each chain or subunit of the is encoded by a separate gene. Alternatively, a single mRNA may be engineered to encode more than one subunit. In one embodiment, the mRNA may encode full length antibodies (both heavy and light chains of the variable and constant regions) or fragments of antibodies (e.g. Fab, Fv, or a single chain Fv (scFv) to confer immunity to a subject.

As used herein, the term "heavy chain" encompasses all types of naturally-occurring heavy chains of different classes of immunoglobulins, including but not limited to, IgM(μ), IgD (δ), IgG(γ), IgA(α), and IgE(ε), and biologically active variants thereof. Typically, a heavy chain according to the present invention contains the N-terminal variable region responsible for antigen recognition, typically including CDR 1, CDR 2 and CDR 3, separated by four framework regions (FR1, FR2, FR2, and FR4). Typically, the N-terminal variable region contains about 100 to 110 or more amino acids. In some embodiments, a heavy chain according to the present invention contains one or more of constant domains (e.g., $C_H1$, $C_H2$, and/or $C_H3$). In some embodiments, an mRNA encoding a heavy chain of an antibody is of or greater than 0.3 kb, 0.5 kb, 0.75 kb, 1.0 kb, 1.25 kb, 1.5 kb, 1.75 kb, 2.0 kb, 2.5 kb, 3.0 kb, 3.5 kb, 4.0 kb in length.

As used herein, the term "light chain" encompasses all types of naturally-occurring light chains of different classes of immunoglobulins, including but not limited to κ or λ isotypes, and biologically active variants thereof. Typically, a light chain according to the present invention comprises an N-terminal variable domain ($V_L$). In some embodiments, a light chain according to the present invention contains a C-terminal constant domain ($C_L$). In some embodiments, an mRNA encoding a light chain of an antibody is of or greater than 0.1 kb, 0.2 kb, 0.3 kb, 0.4 kb, 0.5 kb, 0.6 kb, 0.7 kb, 0.8 kb, 0.9 kb, 1.0 kb, 1.25 kb, 1.5 kb, 1.75 kb, 2.0 kb, 2.5 kb, or 3.0 kb in length.

According to the present invention, a heavy chain and light chain of an antibody may be encoded and delivered by a single mRNA or separate mRNAs. It is contemplated that it may be advantageous to deliver heavy chain encoding mRNA and light chain encoding mRNA at varying ratios in order to optimize production of fully assembled functional antibodies.

In some embodiments, the mRNA may additionally encode one or more secretory leader sequences which are operably linked to and direct secretion of an antibody, antibody fragment(s), or other protein(s). Suitable secretory leader sequences are described, for example, in US 2008/0286834 A1. While one embodiment of the present invention relates to methods and compositions useful for conferring immunity to a subject (e.g., via the translation of mRNA encoding functional antibodies), the inventions disclosed herein and contemplated hereby are broadly applicable. In an alternative embodiment the compositions of the present invention encode antibodies that may be used to transiently or chronically effect a functional response in subjects. For example, the mRNA of the present invention may encode a functional monoclonal or polyclonal antibody, which upon translation and secretion from target cell may be useful for targeting and/or inactivating a biological target (e.g., a stimulatory cytokine such as tumor necrosis factor).

Lipid Carrier Vehicles

The use of lipid carrier vehicles to facilitate the delivery of nucleic acids to target cells is contemplated by the present invention. Lipid carrier vehicles (e.g., liposomes and lipid-derived nanoparticles) are generally useful in a variety of applications in research, industry, and medicine, particularly for their use as transfer vehicles of diagnostic or therapeutic compounds in vivo (Lasic, Trends Biotechnol., 16: 307-321, 1998; Drummond et al., Pharmacol. Rev., 51: 691-743, 1999) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.).

In the context of the present invention, a lipid carrier vehicle typically serves to transport mRNA to a target cell. One unexpected and advantageous feature of the current invention, was the observation that pulmonary administration of mRNA, which is encapsulated within a lipid carrier vehicle, results in delivery of mRNA and/or the protein to non-lung tissue and cells. For the purposes of the present invention, the liposomal transfer vehicles are prepared to contain the desired nucleic acids. The process of incorporation of a desired entity (e.g., a nucleic acid) into a liposome is often referred to as "loading" (Lasic, et al., FEBS Lett., 312: 255-258, 1992). The liposome-incorporated nucleic acids may be completely or be partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments of the present invention, the selected transfer vehicle is capable of enhancing the stability of the mRNA contained therein. The liposome can allow the encapsulated mRNA to reach the target cell and/or may preferentially allow the encapsulated mRNA to reach non-lung tissue and cells, following pulmonary delivery.

In some embodiments, a suitable lipid carrier vehicle is formulated as a lipid nanoparticle. As used herein, the phrase "lipid nanoparticle" and "lipid carrier vehicle" and "lipid-derived nanoparticle" are all used interchangeably, and refer to a delivery vehicle comprising one or more lipids (e.g., cationic lipids, non-cationic lipids, cholesterol-based lipids, and PEG-modified lipids). The contemplated lipid nanoparticles may be prepared by including multi-component lipid mixtures of varying ratios employing one or more cationic lipids, non-cationic lipids, cholesterol-based lipids, and PEG-modified lipids. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides).

Cationic liposome/mRNA complexes can help to protect mRNA from enzymatic degradation and facilitate intracellular delivery by interacting with the negatively charged cell membrane. However, the cationic surface of these lipoplexes also mediates strong interactions with negatively charged proteins that serve to reduce the half-life of the lipoplexes in vivo. This effect may be reduced by employing one or more of a mechanism to reduce the interaction between the cationic liposome/mRNA complex and negatively charged proteins. In most embodiments, the delivery vehicles used in the compositions and methods of the invention comprise nanoparticles constructed from a combination of one or more cationic lipids, non-cationic lipids, such as neutral or helper lipids, and PEG-modified lipids.

Lipid Nanoparticles

In some embodiments, a suitable delivery vehicle is formulated as a lipid nanoparticle. Lipid nanoparticles of the current invention comprise one or more lipids (e.g., cationic lipids, non-cationic lipids, cholesterol-based lipids, and PEG-modified lipids). Also contemplated is the use of polymers as transfer vehicles, whether alone or in combination with other delivery vehicles. In some embodiments, the delivery vehicle is selected based upon its ability to facilitate pulmonary delivery and translocation to non-lung tissue.

As used herein, liposomal delivery vehicles, e.g. lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired mRNA to a target tissue. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

In certain embodiments of the invention, the carrier is formulated using a polymer as a carrier, alone or in combination with other carriers. Suitable polymers may include, for example, polyacrylates, polyalkylcyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDA, e.g., 25 kDa branched PEI (Sigma #408727).

In some embodiments, a suitable delivery vehicle contains a cationic lipid. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, CI 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z, 18Z)—N,N-dimethyl-6-(9Z,12Z)-octadeca-9,12-dien-1-yl) tetracosa-15,18-dien-1-amine (HGT5000), (15Z,18Z)—N, N-dimethyl-6-((9Z,12Z)-octadeca-9,12-dien-1-yl)tetracosa-4,15,18-trien-1-amine (HGT5001), and (15Z,18Z)—N,N- dimethyl-6-((9Z,12Z)-octadeca-9,12-dien-1-yl)tetracosa-5,15,18-trien-1-amine (HGT5002).

In some embodiments, the cationic lipid N-[1-(2,3-dioleyloxyl)propyl]-N,N,N-trimethylammonium chloride or "DOTMA" is used. (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "RE-1" (di((Z)-non-2-en-1-yl) 9-((4-(dimethylamino)butanoyl)oxy)heptadecanedioate) or "RE-2" ((6Z,25Z)-diethyl 16-((4-(dimethylamino)butanoyl)oxy)hentriaconta-6,25-dienedioate) or "RE-3" ((9Z,28Z)-dimethyl 19-((4-(dimethylamino)butanoyl)oxy)heptatriaconta-9,28-dienedioate) (See, US2012/0027803, herein incorporated by reference) or "GL-67" (Andries et al., Molecular Pharmaceutics, 9: 2136-2145 (2012); Zhao et al., "Cationic Liposomes in Different Structural Levels for Gene Delivery", Non-Vrial Gene Therapy, InTech publishing, 13: 293-318 (2011), both of which are herein incorporated by reference) or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-DMA", 2,2-dilinoleyl-4-dimethyl-aminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, the cationic lipid is not "GL-67".

In some embodiments, one or more of the cationic lipids present in such a composition comprise at least one of an imidazole, dialkylamino, or guanidinium moiety.

In some embodiments, one or more of the cationic lipids present in such a composition are chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)—N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, a suitable delivery vehicle contains one or more non-cationic lipids, In some embodiments, a non-cationic lipid is a neutral lipid, i.e., a lipid that does not carry a net charge in the conditions under which the composition is formulated and/or administered. Such exemplary non-cationic or neutral lipids can be chosen from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), and cholesterol.

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

In other embodiments, suitable lipid nanoparticles comprising one or more cleavable lipids, such as, for example, one or more cationic lipids or compounds that comprise a cleavable disulfide (S—S) functional group (e.g., HGT4001, HGT4002, HGT4003, HGT4004 and HGT4005), as further described in U.S. Provisional Application No. 61/494,745, the entire teachings of which are incorporated herein by reference in their entirety.

In addition, several reagents are commercially available to enhance transfection efficacy. Suitable examples include LIPOFECTIN (DOTMA:DOPE) (Invitrogen, Carlsbad, Calif.), LIPOFECTA INE (DOSPA:DOPE) (Invitrogen), LIPOFECTAMINE2000. (Invitrogen), FUGENE, TRANSFECTAM (DOGS), and EFFECTENE.

In some embodiments, the cationic lipid may comprise a molar ratio of about 1% to about 90%, about 2% to about 70%, about 5% to about 50%, about 10% to about 40% of the total lipid present in the transfer vehicle, or preferably about 20% to about 70% of the total lipid present in the transfer vehicle.

The use of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipids together which comprise the transfer vehicle (e.g., a lipid nanoparticle). Contemplated PEG-modified lipids include, but is not limited to, a polyethylene glycol chain of up to 5 kDa in length covalently attached to a lipid with alkyl chain(s) of C6-C20 length. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the liposomal transfer vehicle.

The present invention also contemplates the use of non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the transfer vehicle.

In particular embodiments, a suitable transfer vehicle (e.g., a lipid nanoparticle) is prepared by combining multiple lipid and/or polymer components. For example, a transfer vehicle may be prepared using C12-200, DOPE, chol, DMG-PEG2K at a molar ratio of 40:30:25:5, or DODAP, DOPE, cholesterol, DMG-PEG2K at a molar ratio of 18:56:20:6, or HGT5000, DOPE, chol, DMG-PEG2K at a molar ratio of 40:20:35:5, or HGT5001, DOPE, chol, DMG-PEG2K at a molar ratio of 40:20:35:5. The selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly. For example, in embodiments, the percentage of cationic lipid in the lipid nanoparticle may be greater than 10%, greater than 20%, greater than 30%, greater than 40%, greater than 50%, greater than 60%, or greater than 70%. The percentage of non-cationic lipid in the lipid nanoparticle may be greater than 5%, greater than 10%, greater than 20%, greater than 30%, or greater than 40%. The percentage of cholesterol in the lipid nanoparticle may be greater than 10%, greater than 20%, greater than 30%, or greater than 40%. The percentage of PEG-modified lipid in the lipid nanoparticle may be greater than 1%, greater than 2%, greater than 5%, greater than 10%, or greater than 20%.

In certain embodiments, suitable lipid nanoparticles of the invention comprise at least one of the following cationic lipids: C12-200, HGT4003, HGT5000, HGT5001, RE-1, RE-2, RE3, GL-67 and ICE. In some specific embodiments, a suitable lipid nanopartical is formulated without using the cationic lipid GL-67. In some embodiments, suitable transfer vehicle comprises cholesterol and/or a PEG-modified lipid. In some embodiments, suitable transfer vehicles comprises DMG-PEG2K. In some embodiments, suitable transfer vehicle comprises one of the following lipid combinations: C12-200, DOPE, cholesterol, DMG-PEG2K; DODAP, DOPE, cholesterol, DMG-PEG2K; HGT5000, DOPE, cholesterol, DMG-PEG2K; HGT5001, DOPE, cholesterol, DMG-PEG2K; XTC, DSPC, cholesterol, PEG-DMG; MC3, DSPC, cholesterol, PEG-DMG; and ALNY-100, DSPC, cholesterol, DLinKC2-DMA, DODMA, DLinDMA, CLinDMA PEG-DSG.

The lipid carrier vehicles for use in the compositions of the invention can be prepared by various techniques which are presently known in the art. Multilamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments of this invention, the compositions of the present invention comprise a transfer vehicle wherein the mRNA is associated on both the surface of the transfer vehicle and encapsulated within the same transfer vehicle. For example, during preparation of the compositions of the present invention, cationic liposomal transfer vehicles may associate with the mRNA through electrostatic interactions. For example, during preparation of the compositions of the present invention, cationic liposomal transfer vehicles may associate with the mRNA through electrostatic interactions.

In some embodiments, the compositions and methods of the invention comprise mRNA encapsulated in a lipid carrier vehicle. In some embodiments, the one or more mRNA species may be encapsulated in the same lipid carrier vehicle. In some embodiments, the one or more mRNA species may be encapsulated in different lipid carrier vehicles. In some embodiments, the mRNA is encapsulated in one or more lipid carrier vehicles, which differ in their lipid composition, molar ratio of lipid components, size, charge (Zeta potential), targeting ligands and/or combinations thereof. In some embodiments, the one or more lipid carrier vehicles may have a different composition of cationic lipids, neutral lipid, PEG-modified lipid and/or combinations thereof. In some embodiments the one or more lipid carrier vehicles may have a different molar ratio of cationic lipid, neutral lipid, cholesterol and PEG-modified lipid used to create the lipid carrier vehicle.

Delivery Methods

The route of delivery used in the methods of the invention allows for non-invasive, self-administration of the therapeutic compositions of the invention. The methods of the invention involve intratracheal or pulmonary administration by aerosolization, nebulization, or instillation of compositions comprising mRNA encoding a therapeutic protein in a suitable transfection or lipid carrier vehicles as described above.

Although the local cells and tissues of the lung represent a potential target capable of functioning as a biological depot or reservoir for production and secretion of the protein encoded by the mRNA, applicants have discovered that administration of the compositions of the invention to the lung via aerosolization, nebulization, or instillation results in the distribution of even non-secreted proteins outside the lung cells. Without wishing to be bound by any particular theory, it is contemplated that nanoparticle compositions of the invention pass, through the lung airway-blood barrier, resulting in translation of the intact nanoparticle to non-lung cells and tissues, such as, e.g., the heart, the liver, the spleen, where it results in the production of the encoded protein in these non-lung tissues. Thus, the utility of the compositions and methods of the invention extend beyond production of therapeutic protein in lung cells and tissues of the lung and can be used to delivery to non-lung target cells and/or tissues They are useful in the management and treatment of a large number of diseases, and in particular peripheral diseases which result from both secreted and non-secreted protein and/or enzyme deficiencies (e.g., one or more lysosomal storage disorders). In certain embodiments, the compositions of the invention, used in the methods of the invention result in the distribution of the mRNA encapsulated nanoparticles and production of the encoded protein in the liver, spleen, heart, and/or other non-lung cells. For example, administration of the compositions of the present inventions, such as, e.g., a nanoparticle comprising mRNA encoding beta galactosidase (a non-secreted protein), by aerosolization, nebulization, or instillation to the lung will result in the composition itself and its protein product (e.g., functional beta galactosidase protein) will be detectable in both the local cells and tissues of the lung, as well as in peripheral target cells, tissues and organs as a result of translocation of the mRNA and delivery vehicle to non-lung cells.

In certain embodiments, the compositions of the invention may be employed in the methods of the invention to specifically target peripheral cells or tissues. Following the pulmonary delivery, it is contemplated that the compositions of the invention cross the lung airway-blood barrier and distribute into cells other than the local lung cells. Accordingly, the compositions disclosed herein may be administered to a subject by way of the pulmonary route of administration, using a variety of approach known by those skilled in the art (e.g., by inhalation), and distribute to both the local target cells and tissues of the lung, as well as in peripheral non-lung cells and tissues (e.g., cells of the liver, spleen, kidneys, heart, skeletal muscle, lymph nodes, brain, cerebrospinal fluid, and plasma). As a result, both the local cells of the lung and the peripheral non-lung cells can serve as biological reservoirs or depots capable of producing and/or secreting a translation product encoded by one or more polynucleotides. Accordingly, the present inventions are not limited to the treatment of lung diseases or conditions, but rather can be used as a non-invasive means of facilitating the delivery of polynucleotides, or the production of enzymes and proteins encoded thereby, in peripheral organs, tissues and cells (e.g., hepatocytes) which would otherwise be achieved only by systemic administration. Exemplary peripheral non-lung cells include, but are not limited to, hepatocytes, epithelial cells, hematopoietic cells, epithelial cells, endothelial cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following administration of the composition to the subject, the protein product encoded by the mRNA (e.g., a functional protein or enzyme) is detectable in the peripheral target tissues for at least about one to seven days or longer following administration of the composition to the subject. The amount of protein product necessary to achieve a therapeutic effect will vary depending on the condition being treated, the protein encoded, and the condition of the patient. For example, the protein product may be detectable in the peripheral target tissues at a concentration (e.g., a therapeutic concentration) of at least 0.025-1.5 µg/ml (e.g., at least 0.050 µg/ml, at least 0.075 µg/ml, at least 0.1 µg/ml, at least 0.2 µg/ml, at least 0.3 µg/ml, at least 0.4 µg/ml, at least 0.5 µg/ml, at least 0.6 µg/ml, at least 0.7 µg/ml, at least 0.8 µg/ml, at least 0.9 µg/ml, at least 1.0 µg/ml, at least 1.1 µg/ml, at least 1.2 µg/ml, at least 1.3 µg/ml, at least 1.4 µg/ml, or at least 1.5 µg/ml), for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 days or longer following administration of the composition to the subject.

It has been demonstrated that nucleic acids can be delivered to the lungs by intratracheal administration of a liquid suspension of the nucleic acid composition and inhalation of an aerosol mist produced by a liquid nebulizer or the use of a dry powder apparatus such as that described in U.S. Pat. No. 5,780,014, incorporated herein by reference.

In certain embodiments, the compositions of the invention may be formulated such that they may be aerosolized or otherwise delivered as a particulate liquid or solid prior to or upon administration to the subject. Such compositions may be administered with the assistance of one or more suitable devices for administering such solid or liquid particulate compositions (such as, e.g., an aerosolized aqueous solution or suspension) to generate particles that are easily respirable or inhalable by the subject. In some embodiments, such devices (e.g., a metered dose inhaler, jet-nebulizer, ultrasonic nebulizer, dry-powder-inhalers, propellant-based inhaler or an insufflator) facilitate the administration of a predetermined mass, volume or dose of the compositions (e.g., about 0.5 mg/kg of mRNA per dose) to the subject. For example, in certain embodiments, the compositions of the invention are administered to a subject using a metered dose inhaler containing a suspension or solution comprising the composition and a suitable propellant. In certain embodiments, the compositions of the invention may be formulated as a particulate powder (e.g., respirable dry particles) intended for inhalation. In certain embodiments, compositions of the invention formulated as respirable particles are appropriately sized such that they may be respirable by the subject or delivered using a suitable device (e.g., a mean D50 or D90 particle size less than about 500 µm, 400 µm, 300 µm, 250 µm, 200 µm, 150 µm, 100 µm, 75 µm, 50 µm, 25 µm, 20 µm, 15 µm, 12.5 µm, 10 µm, 5 µm, 2.5 µm or smaller). In yet other embodiments, the compositions of the invention are formulated to include one or more pulmonary surfactants (e.g., lamellar bodies). In some embodiments, the compositions of the invention are administered to a subject such that a concentration of at least 0.05 mg/kg, at least 0.1 mg/kg, at least 0.5 mg/kg, at least 1.0 mg/kg, at least 2.0 mg/kg, at least 3.0 mg/kg, at least 4.0 mg/kg, at least 5.0 mg/kg, at least 6.0 mg/kg, at least 7.0 mg/kg, at least 8.0 mg/kg, at least 9.0 mg/kg, at least 10 mg/kg, at least 15 mg/kg, at least 20 mg/kg, at least 25 mg/kg, at least 30 mg/kg, at least 35 mg/kg, at least 40 mg/kg, at least 45 mg/kg, at least 50 mg/kg, at least 55 mg/kg, at least 60 mg/kg, at least 65 mg/kg, at least 70 mg/kg, at least 75 mg/kg, at least 80 mg/kg, at least 85 mg/kg, at least 90 mg/kg, at least 95 mg/kg, or at least 100 mg/kg body weight is administered in a single dose. In some embodiments, the compositions of the invention are administered to a subject such that a total amount of at least 0.1 mg, at least 0.5 mg, at least 1.0 mg, at least 2.0 mg, at least 3.0 mg, at least 4.0 mg, at least 5.0 mg, at least 6.0 mg, at least 7.0 mg, at least 8.0 mg, at least 9.0 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg or at least 100 mg mRNA is administered in one or more doses.

EXAMPLES

Example 1: Comparison of Unmodified and Modified mRNA in Naked Form or in Nanoparticles by Intratracheal Administration Overview: Mice were intratracheally (IT) sprayed either with unmodified or modified mRNA (25% of both cytidine-5'-triphosphate and uridine-5'-triphosphate were replaced by 5-methylcytidine-5'-triphosphate and 2-thiouridine-5'-triphosphate, respectively) coding for firefly luciferase (FFL) either in naked form or encapsulated in lipid based nanoparticles (NPs) for single dose administration. Luciferase production was measured by in vivo Bioluminescence Imaging (BLI) at different time points post IT spray. Organs from mice treated with C12-200 based NPs at a dose amounting to 20 μg/mouse were prepared for histopathological analysis. To assess biodistribution of complexes post IT spray, in vitro luciferase production was measured in the organs prepared from the euthanized mice treated with doses corresponding to 5 and 10 μg C12-200 based NPs per mouse.

A. IT Spray of Naked mRNA and mRNA in C12-200 Based Nanoparticles—20 ug Per Mouse Lipid Nanoparticle Formulation: Aliquots of 50 mg/mL ethanolic solutions of C12-200, DOPE, Choleterol, and DMG-PEG2000 were mixed in a molar ratio of 40:30:25:5, respectively, and diluted with ethanol to 3 mL final volume. Separately, an aqueous buffered solution (10 mM citrate/150 mM NaCl, pH 4.5) of FFL or modified FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C.

Messenger RNA was synthesized via in vitro transcription process using a cDNA template encoding FFL protein with predetermined untranslated regions. The resulting RNA construct was processed further incorporating a Cap 1 structure on the 5' end and a poly-A tail length of ~200 adenosine bases.

Modified messenger RNA was synthesized in a similar fashion as stated above with 25% of the uridine bases substituted with 2-thiouridine triphosphate and 25% of the cytidine bases substituted with 5-methylcytidine triphosphate.

Female Balb/c mice were purchased from Elevage-Janvier, France. The mice were 10 weeks old at the start of the experiment. Mice were weighed prior to the start of the experiment and assigned to one of the following four group (n=6 mice per group): group I-IT spray with FFL mRNA; group II-IT spray with modified FFL mRNA; group III-IT spray with FFL-mRNA in C12-200 based lipid nanoparticle; group IV-IT spray with modified FFL-mRNA in C12-200 based lipid nanoparticle. Each mouse was sprayed with 20 μg of the respective mRNA/NPs. The required amount of mRNA/NPs per group were suspended just before application in DEPC treated (0.1%) RNase free water (Serva, Catalog number: 39798, Lot P060383), to a total volume of 50 μl/mouse. NPs were also characterized by size and zeta potential measurements. These measurements were performed in water and are tabulated as Table 5.

TABLE 5

Particle size and zeta potential measurements made in PBS

| | Size (nm) ± polydispersity | Zeta Potential |
|---|---|---|
| FFL-NP | 81.64 ± 0.177 | +50 ± 6.36 |
| FFL-mod-NP | 84.14 ± 0.197 | +52.5 ± 16.2 |

Figure 2:
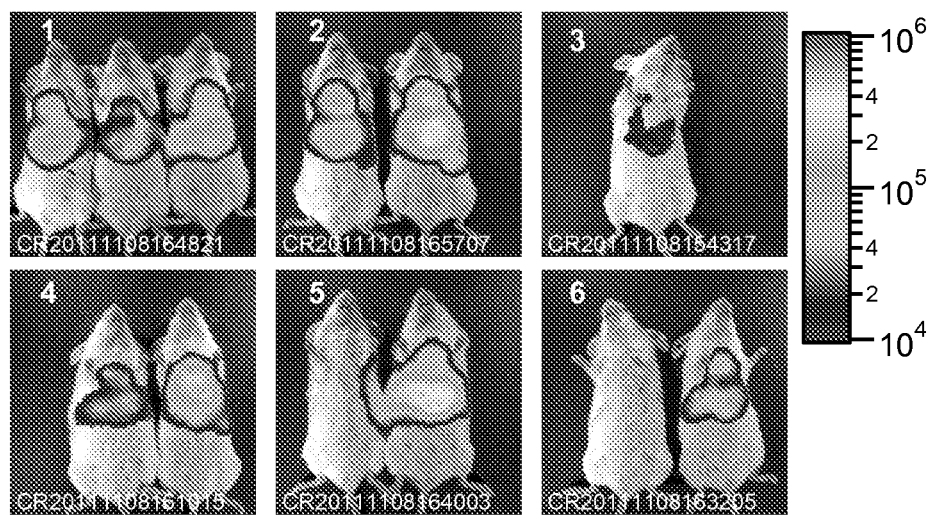
FIG. 2 shows BLI at 6 hrs post IT spray application using BLI. Panels 1, 2, 3 (FFL mRNA in C12-200 based NPs) compared to panels 4, 5, 6 (modified FFL mRNA in C12-200 based NPs).

Luciferase production was measured by in vivo BLI at 6 hours post application. Whereas almost negligible amount of exogenous mRNA-derived protein could be detected with naked mRNA, the nanoparticle formulations, independent of modifications, showed significant levels of luciferase production in the entire thoracic region and upper abdomen (FIG. 1). Compared to modified FFL, the unmodified FFL mRNA resulted in approximately 2-3 fold higher luminescence at 6 hours (FIG. 2).

Figure 3:
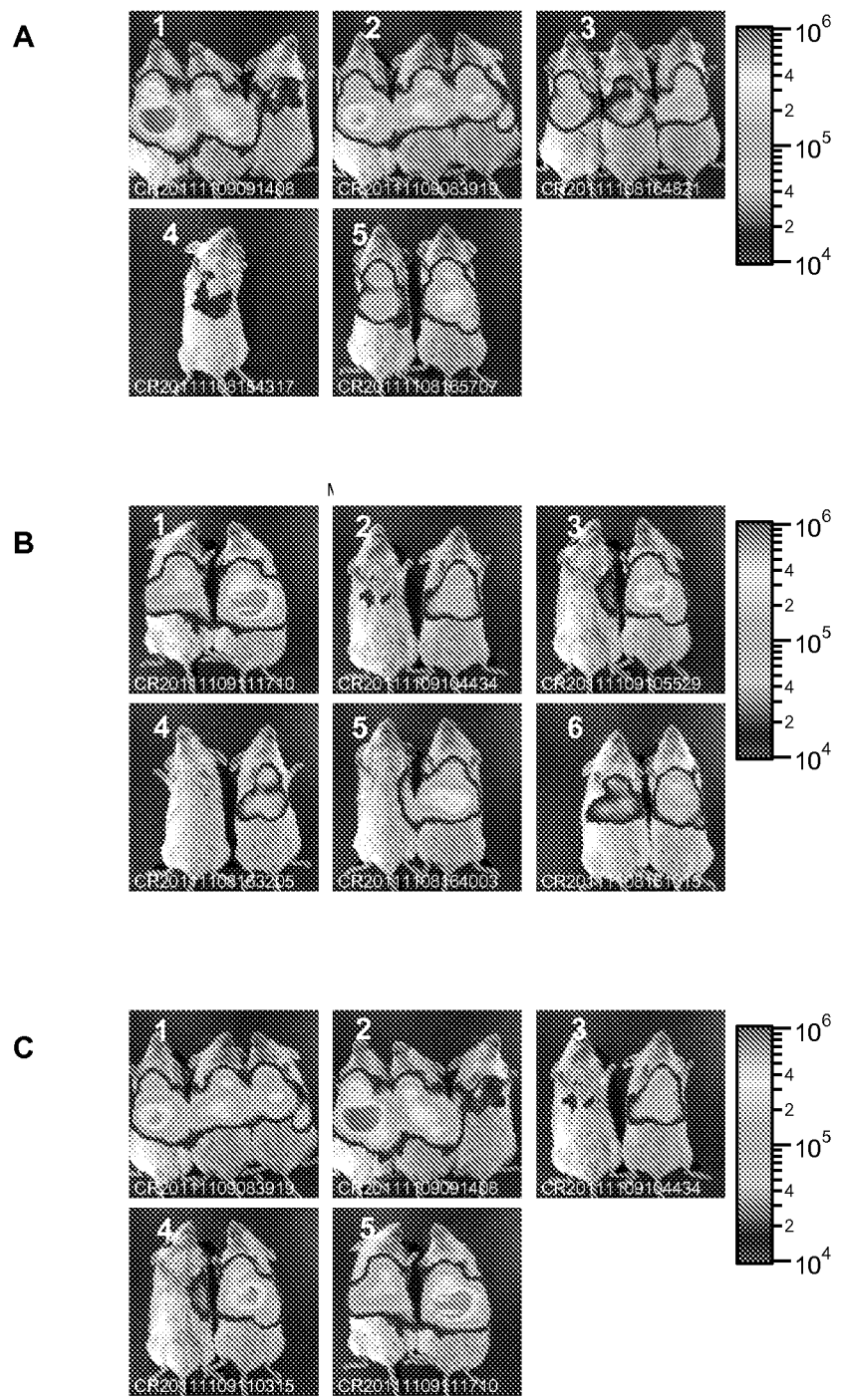
FIG. 3 shows BLI images of mice post IT spray application. (A) All mice (FFL mRNA in C12-200 based NPs); panels 1, 2, 3 after 24 hours compared to panels 4, 5, 6 after 6 hours. (B) All mice (modified FFL mRNA in C12-200 based NPs); panels 1, 2 after 24 hours compared to panels 3, 4, 5 after 6 hours. (C) Panels 1, 2, (FFL mRNA in C12-200 based NPs) compared to panels 3, 4, 5 (modified FFL mRNA in C12-200 based NPs) after 24 hours.

(FIGS. 1A and B), very low (close to background) level luminescence could be detected with naked mRNA. In mice treated with lipid nanoparticles, independent of modifications, increased luciferase production (~2-3 fold), compared to 6 hour time point, was observed 24 hours after treatment (FIGS. 3A and B). No significant difference could be observed between luciferase production from FFL or modified FFL mRNA (FIG. 3C).

Figure 4:
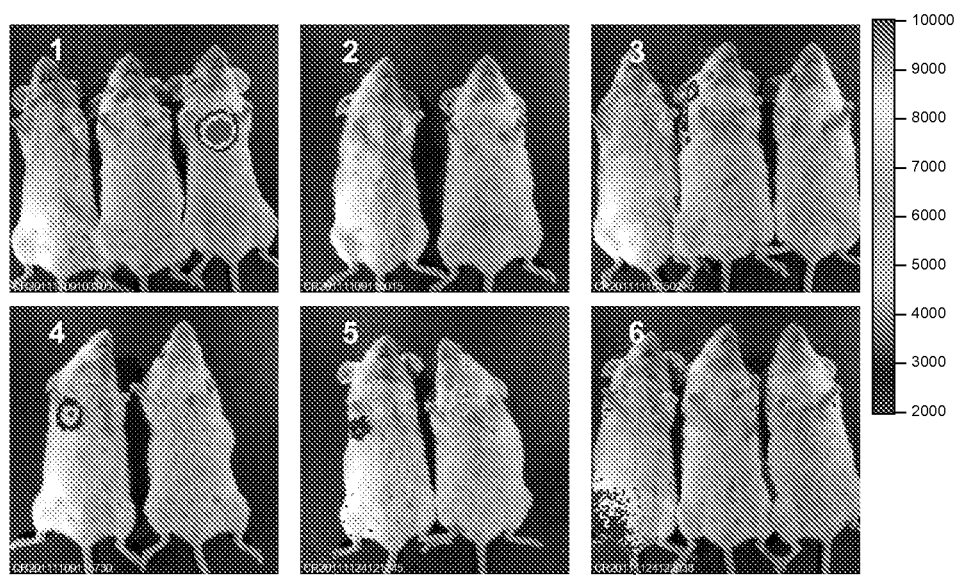
FIG. 4 shows BLI images of mice treated with naked FFL mRNA at 24 hrs post applications. Panels 1, 2 (24 hours after first application); panels 3, 4 (24 hours after second application); panels 5, 6 (24 hours after third application).
Figure 5:
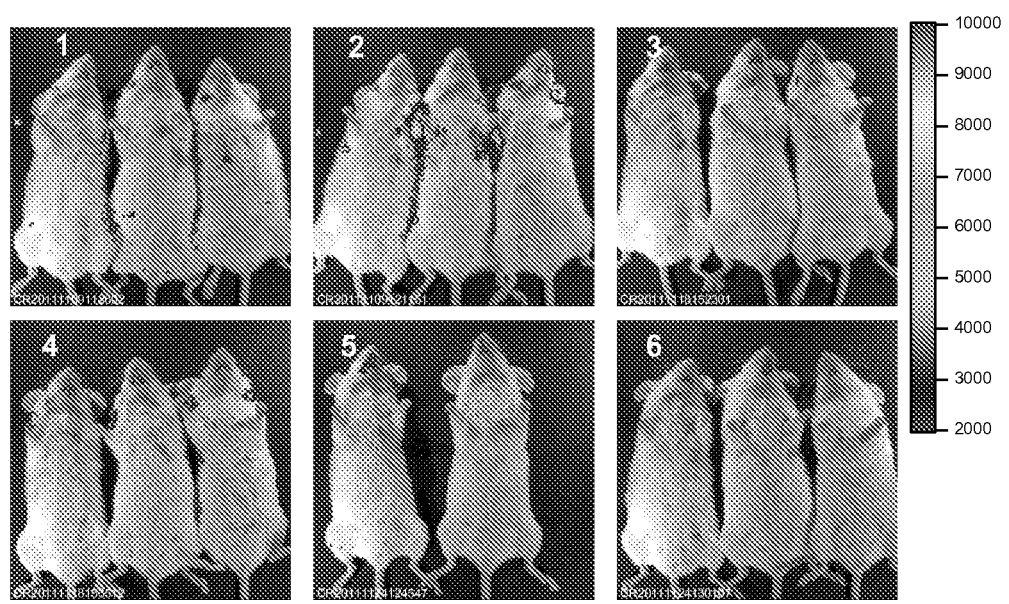
FIG. 5 shows BLI images of mice treated with naked modified FFL mRNA at 24 hrs post application. Panels (24 hours after first application); panels 3, 4 (24 hours after second application); panels 5, 6 (24 hours after third application).

The mice treated with naked mRNA, were followed further in the experiment and two additional doses at weekly intervals were applied. BLI was performed at different time points post application. The BLI images at 24 hours post application, the time point of maximum luminescence (FIG. 3), are shown in FIG. 4 (naked FFL mRNA) and FIG. 5 (naked modified FFL mRNA). With a few exceptions, no noticeable luciferase production was observed for any of the measured mice (compare the scales in FIGS. 4 and 5 with FIG. 3).

B. IT Spray of FFL and Modified FFL mRNA in C12-200 Based Nanoparticles—5 μg Per Mouse and 10 μg Per Mouse IT spray experiments were performed with reduced doses of 5 and 10 μg/mouse. The C12-200 based nanoparticle formulation was as described in Example 1.

Experimental Design: Female Balb/c mice were purchased from Elevage-Janvier, France. The mice were 19 weeks old at the start of the experiment. Mice were weighed prior to the start of the experiment. The C12-200 based lipid nanoparticles were suspended just before application in DEPC treated (0.1%) RNase free water (Serva, Catalog number: 39798, Lot P060383), to a total volume of 50 µl/mouse. The following four groups were tested (n=5 mice per group): group I-IT spray with FFL mRNA in C12-200 based nanoparticles (5 µg/mouse); group II-IT spray with FFL mRNA in C12-200 based nanoparticles (10 µg/mouse); group III-IT spray with modified FFL mRNA in C12-200 based nanoparticles (5 µg/mouse); and group IV-IT spray with modified FFL mRNA in C12-200 based nanoparticles (10 µg/mouse). One mouse from group III and IV died during IT spray. Thus, the remaining number of animals for these groups was four. At 6 hours post application, all animals showed piloerection and reduced motility. Moreover, one mouse from each of the higher dose groups (groups II and IV) was dead at this time point. BLI imaging was performed for the mice at 6 hours post application.

Figure 6:
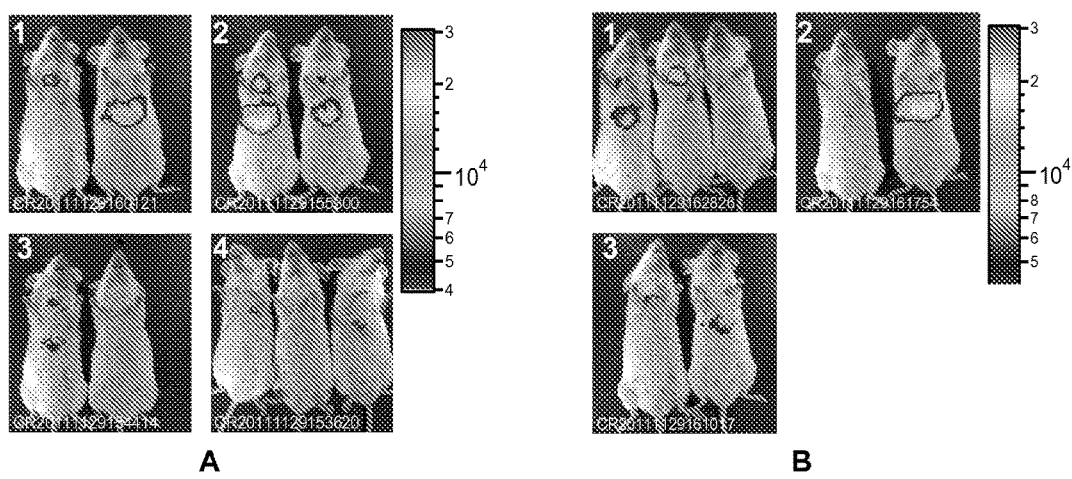
FIG. 6 shows BLI images of mice at 6 hours post IT spray application. (A) Panels 1, 2 (FFL mRNA in C12-200 based NPs (10 µg/mouse)); panels 3, 4 (FFL mRNA in C12-200 based NPs (5 µg/mouse). (B) Panel 1 (modified FFL mRNA in C12-200 based NPs (10 µg/mouse)); panels 2, 3 (modified FFL mRNA in C12-200 based NPs (5 µg/mouse).

Using FFL mRNA at the doses of 5 µg/mouse resulted in extremely low levels of luciferase production. With the 10 µg/mouse dose, greater production was observed which was concentrated in the liver (FIG. 6A). The difference between the applied doses was not very evident in the modified FFL mRNA groups (FIG. 6B). Comparing the mice from group II (FFL mRNA) with group IV (modified FFL mRNA) revealed higher luminescence in the former (compare FIG. 6A panel 1, 2 with panel 1 in FIG. 6B).

Figure 7:
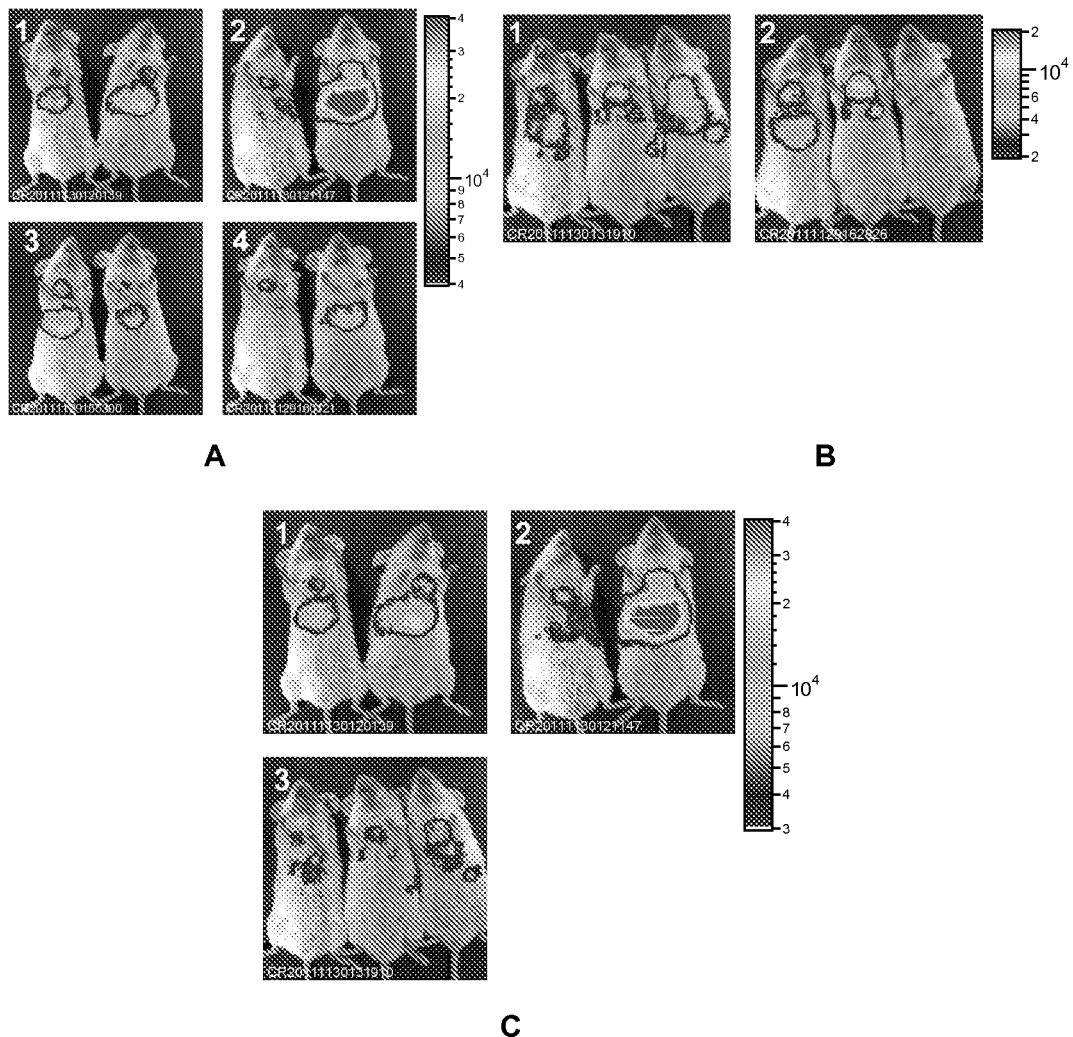
FIG. 7 shows BLI images of mice at 6 hrs and 24 post IT spray application at doses of 10 µg/mouse. (A) All mice (FFL mRNA in C12-200 based NPs); panels 1, 2 (24 hours); panels 3, 4 (6 hours). (B) All mice (modified FFL mRNA in C12-200 based NPs); panel 1 (24 hours); panel 2 (6 hours). (C) Comparison of panels 1, 2 (FFL mRNA in C12-200 based NPs) with panel 3 (modified FFL mRNA in C12-200 based NPs) at 24 hrs post IT spray.

Luciferase production at 24 hours was significantly enhanced compared to 6 hours post IT spray (FIGS. 7A and 7B). Moreover, higher production was observed using FFL mRNA as compared to modified FFL mRNA (FIG. 7C). Similar results were obtained in Example 1 with the dose of 20 µg/mouse. Internal organs (heart, liver, lungs, liver, spleen and kidney) were frozen in liquid nitrogen for in-vitro luciferase measurements.

Figure 8:
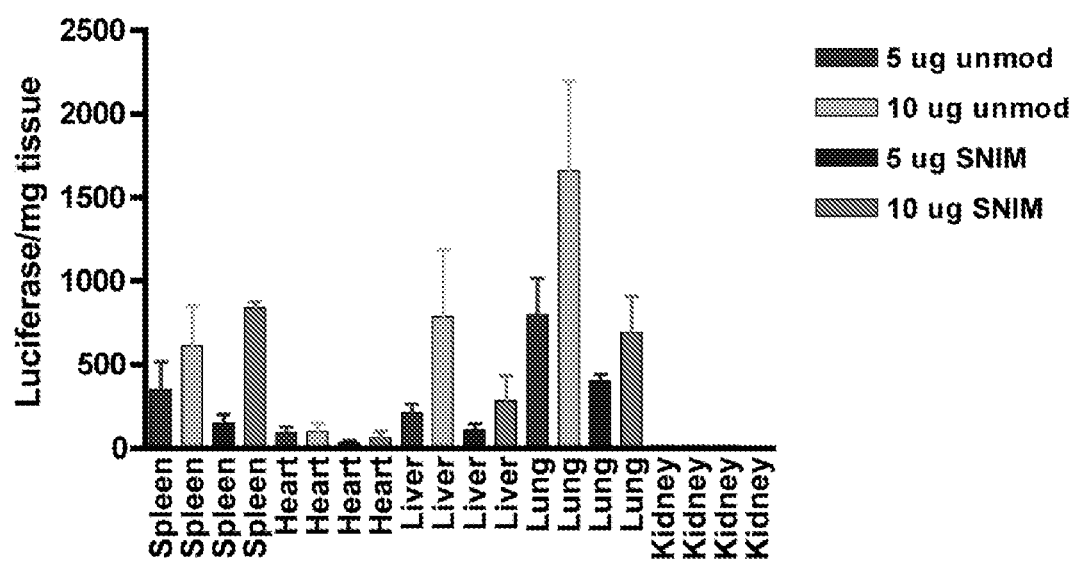
FIG. 8 shows biodistribution of FFL and modified FFL mRNA in C12-200 based NPs at 5 or 10 µg/mouse doses post IT spray.

Biodistribution after IT spray: The isolated organs were homogenized in the frozen state using a mortar and pestle, weighed and lysed in a solution containing Lysis-buffer (25 mM TRIS-Cl 0.1% Triton x-100; pH 7.4) and Complete-Protease-Inhibitor (Roche). Spleen, heart and kidneys were lysed in 250 µl, whereas lungs and liver were lysed in 400 µl. After incubation on ice for 20 min, samples were centrifuged at 10.000 rpm, 4° C. for 10 min. Luciferase activity was measured using 100 µl of the supernatant. Each sample was measured in duplicates and mean values from duplicates were used in analysis. All organs except the kidneys were positive for luciferase activity (FIG. 8). In accordance with our BLI data, maximum luminescence was observed in liver and lungs. FFL-mRNA resulted in higher protein production compared to modified-FFL-mRNA and a dose dependency was evident.

C. IT Spray of Modified FFL mRNA in HGT5001 Based Nanoparticles—20 µg Per Mouse

An IT spray experiment was performed with an HGT5001 based nanoparticle formulation.

Lipid nanoparticle formulation: Aliquots of 50 mg/mL ethanolic solutions of HGT5001:DOPE:Cholesterol:DMG-PEG2K were mixed in a molar ratio of 40:20:35:5, respectively, and diluted with ethanol to 3 mL final volume. Separately, an aqueous buffered solution (10 mM citrate/150 mM NaCl, pH 4.5) of FFL or modified FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4) followed by distilled RNAse-free water, concentrated and stored at 2-8° C.

Experimental Design: Female Balb/c mice were purchased from Elevage-Janvier, France. The mice were 13 weeks old at the start of the experiment. Mice were weighed prior to the start of the experiment. The lipid nanoparticles were suspended just before application in DEPC treated (0.1%) RNase free water (Serva, Catalog number: 39798, Lot P060383), to a total volume of 50 µl/mouse.

IT Spray and BLI: Each mouse was IT sprayed with 20 µg of the HGT5001 based nanoparticle formulation in a total volume of 50 µl/mouse. BLI imaging was performed for the mice at 6 hrs post application.

Figure 9:
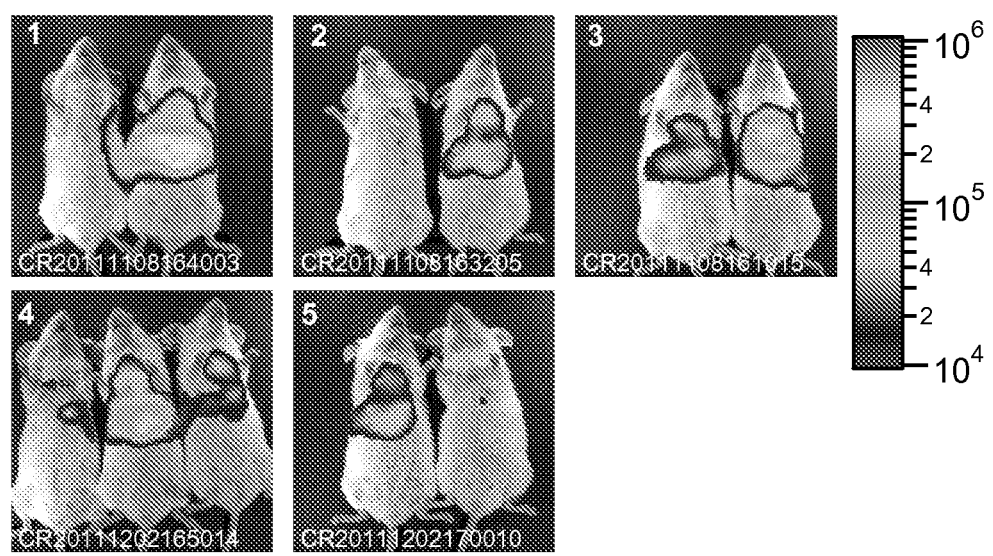
FIG. 9 shows BLI images of mice at 6 hrs post IT spray application. Panels 1, 2, 3 (modified FFL mRNA in C12-200 based NPs); panels 4, 5 (modified FFL mRNA in HGT5001 based NPs)
Figure 10:
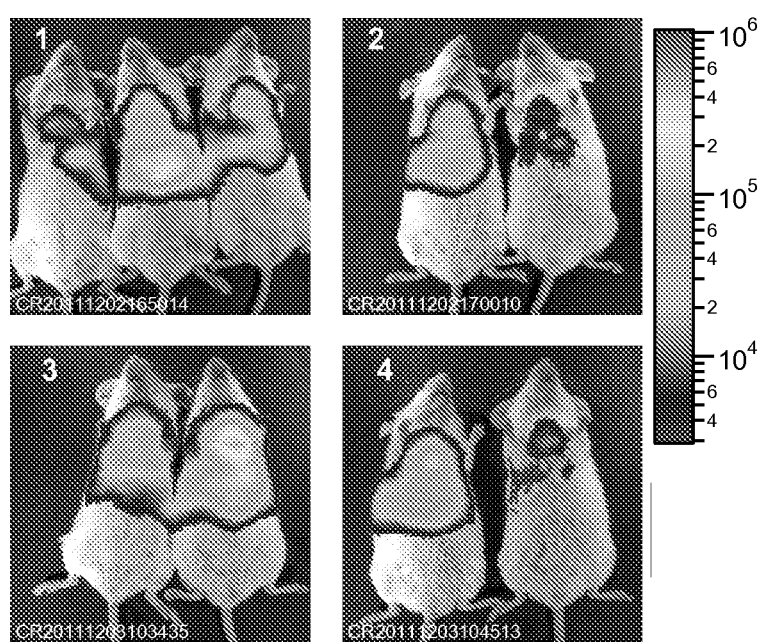
FIG. 10 shows BLI images of mice at 6 hrs (panels 1, 2) and 24 hrs (panels 3, 4) post IT spray application of modified FFL mRNA in HGT5001:DOPE:Cholesterol:DMG-PEG2000 (40:20:35:5) nanoparticles at doses of 10 µg/mouse.

Significantly lower luminescence values were observed with the HGT5001 based nanoparticles when compared to the corresponding time point with the C12-200 based nanoparticles and no increase in protein production from 6 to 24 hours was observed (FIG. 9 and FIG. 10).

Figure 11:
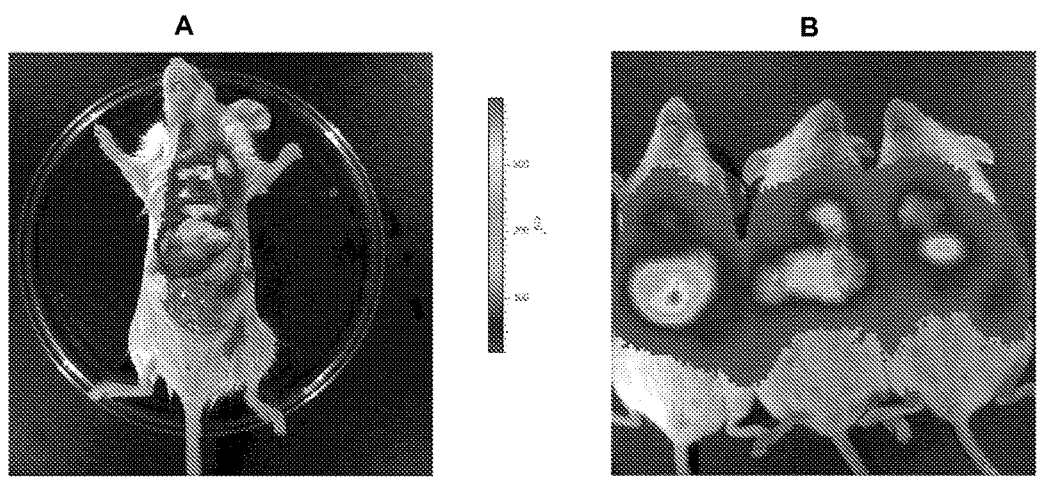
FIG. 11 shows BLI image of mice at 24 hrs post IT spray application. (A) Mice with fur removed (modified FFL mRNA in C12-200 based NPs). (B) Mice with fur intact (modified FFL mRNA in C12-200 based NPs).
Figure 12:
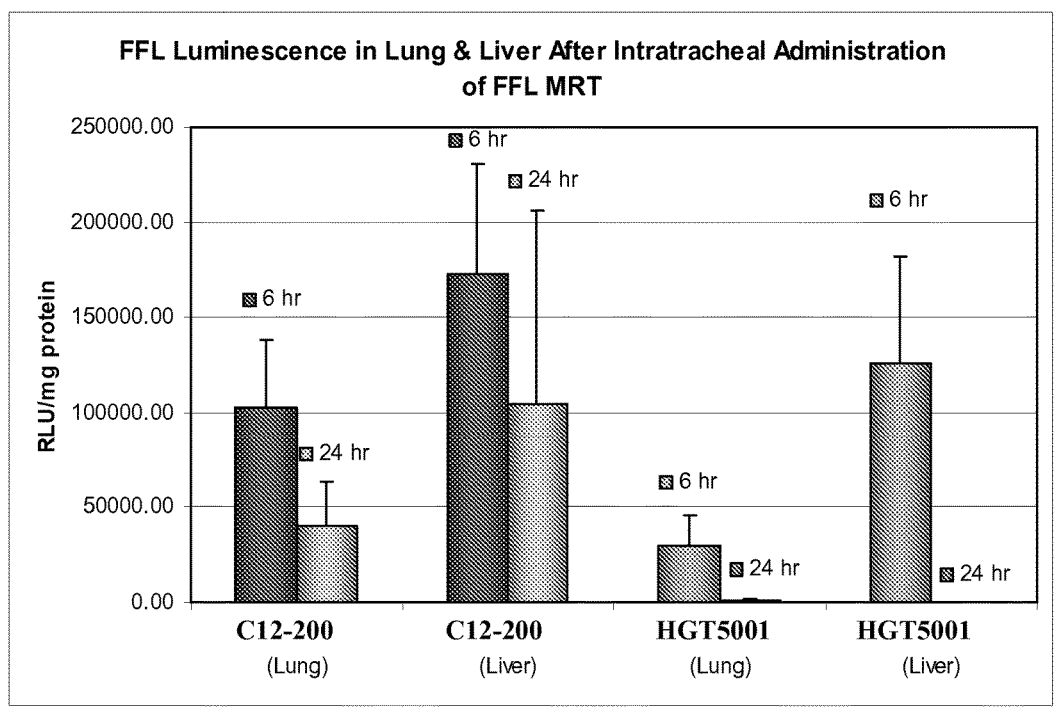
FIG. 12 shows FFL luminescence detected in lung, liver of mice after a single, intravenous injection treatment of mRNA-encapsulated lipid nanoparticles formulations, C12-200:DOPE:Cholesterol:DMG-PEG2000 (40:30:25:5) and HGT5001:DOPE:Cholesterol:DMG-PEG2000 (40:20:35:5). Mice were sacrificed at 6 hr and 24 hr post-administration.

In an independent experiment testing C12-200 and HGT5001 based nanoparticle formulations, following BLI imaging (FIG. 11), mice were euthanized and organs (heart, lungs, liver, spleen and kidney) were evaluated by histology (FIG. 12). FFL production was confirmed in the lung and liver for both C12-200 based NPs and HGT5011 based NPs.

D. IT Spray of Modified FFL mRNA—Non-Nanoparticle Delivery

Naked mRNA resulted in low efficiency without perfluorocarbon treatment. IT aerosolization of encapsulated mRNA lead to protein production in lungs, liver, spleen, and heart. FFL and modified FFL were equally efficient with respect to protein production and with a dose-response.

Various delivery vehicles were tested, including polethylenimines (L-PEI 22 kDa, br-PEI 25 kDa), copolymers of oligo(ethylene glycol) methyl ether methacrylate (OEGMA) and N,N-dimethylaminoethyl methacrylate (DMAEMA), MLRI:DOPE, DOTAP, DMRIE-C, and Lipofectamine, and did not show luminescence in non-lung cells. In contrast, C12-200 and HGT5001 based lipid nanoparticle formulations resulted in significant protein production in non-lung cells following pulmonary delivery.

These observations indicate that only the nanoparticle formulations were able to translocate intact, by either active or passive means, from the lung to the systemic blood supply and subsequently to be deposited in different tissues, such as the liver. This translocation of an intact mRNA encoding a cytosolic protein, firefly luciferase, constitutes non-invasive systemic delivery of an active pharmaceutical ingredient beyond the lung to result in the production of a functional protein to systemically accessible tissues.

E. Nebulization of Modified FFL mRNA with PEI Based Lipid Nanoparticles

Figure 13:
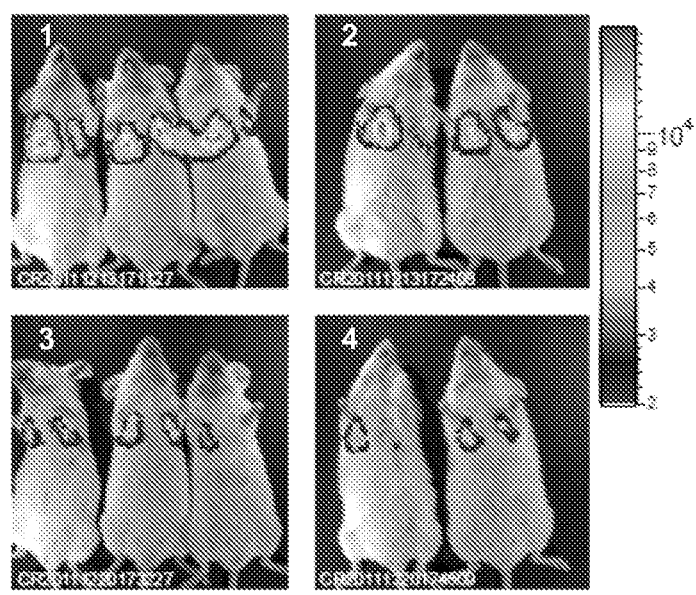
FIG. 13 shows BLI images of mice 6 hours post nebulization with modified FFL mRNA (panels 1, 2) and FFL mRNA (panels 3, 4) in PEI based NPs.

Mice that received modified FFL mRNA in PEI based nanoparticles showed luminescence in the lung (FIG. 13). Luciferase production was greater with modified FFL mRNA (panels 1, 2) compared to unmodified FFL mRNA (panels 3, 4).

Example 2: Evaluation of Nanoparticle Migration by Measuring Lipid in Non-Lung Target Cells To identify the passage of intact nanoparticles in non-lung tissues, aliquots of 50 mg/mL ethanolic solutions of C12-200, DOPE, Chol, DMG-PEG2000 and 1,2-dipalmitoyl-sn-glycero-3-phosphoethanolamine-N-(lissamine rhodamine B sulfonyl) (ammonium salt) are mixed in a molar ratio of 40:29:25:5:1, respectively, and diluted with ethanol to 3 mL final volume. Separately, an aqueous buffered solution (10 mM citrate/150 mM NaCl, pH 4.5) of non-secreted protein, such as beta-galactosidase or FFL (modified or unmodified) mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C.

Messenger RNA is synthesized via in vitro transcription process using a cDNA template encoding beta-galactosidase or FFL protein with predetermined untranslated regions. The resulting mRNA construct is processed further incorporating a Cap 1 structure on the 5' end and a poly-A tail length of ~200 adenosine bases.

Modified messenger RNA is synthesized in a similar fashion as stated above with 25% of the uridine bases substituted with 2-thiouridine triphosphate and 25% of the cytidine bases substituted with 5-methylcytidine triphosphate.

Female Balb/c mice are purchased from Elevage-Janvier, France. The mice are 10 weeks old at the start of the experiment. Mice are weighed prior to the start of the experiment. Each mouse is sprayed with 20 µg of the respective mRNA/NPs comprising unmodified and modified mRNA in fluorescently labeled C12-200 based lipid nanoparticles. The mRNA encapsulated nanoparticles are suspended just before application in DEPC treated (0.1%) RNase free water (Serva, Catalog number: 39798, Lot P060383), to a total volume of 50 µl/mouse. Six hours after treatment mice are killed and organs are excised for histological examination of NP distribution by fluorescence microscopy on 6 µm cryosections.

Alternatively, mRNA is radioactively labeled with, e.g. $I^{123}$ according to the method of Commerford as described in detail by Terebesi et al (Terebesi J, Kwok K Y, Rice K G. Anal Biochem. 1998 Oct. 1; 263(1):120-3). The labeling mixture is separated using a PD-10 gel filtration column (Amersham Biosciences, Freiburg, Germany) with water as eluent. The iodinated mRNA is mixed with unlabeled mRNA resulting in the desired amounts of mRNA which is formulated with lipids as described above and IT aerosolized to the mice lungs. At a desired time point, mice are killed and radioactivity of the organs is measured using a gamma counter.

The above examples demonstrate mRNA can be effectively delivered to non-lung cells or tissues through pulmonary administration using the methods and compositions described herein. In the representative examples above, mRNA delivery was evaluated using the fluorescent firefly luciferase reporter protein encoded by a codon optimized sequence of modified mRNA. However, it will be appreciated by those skilled in the art, that such examples are merely representative of a wide range of mRNAs and proteins that can be delivered according to the present invention. In particular, it will be readily apparent to one skilled in the art that the compositions and methods of the current invention may be used to delivery mRNA encoding various therapeutic proteins to non-lung cells or tissues within a subject for the treatment of associated diseases, disorders or conditions.

From the foregoing description, one skilled in the art can easily ascertain the essential characteristics of this invention, and without departing from the spirit and scope thereof, can make various changes and modifications of the invention to adapt it to various usages and conditions.

All references, patents or applications, U.S. or foreign, cited in the application are hereby incorporated by reference as if written herein in their entireties. Where any inconsistencies arise, material literally disclosed herein controls.

We claim:

1. A method of delivery of messenger RNA (mRNA) to a non-lung cell or tissue comprising administering to the lung by nebulization a composition comprising mRNA encoding a protein and a lipid carrier vehicle comprising one or more PEG-modified lipids, wherein the administering to the lung results in the delivery of the mRNA to a non-lung cell or tissue, and wherein the protein encoded by the mRNA is detectable in the non-lung cell or tissue for at least 6 hours following the administration to the lung.

2. The method of claim 1, wherein the non-lung cell is selected from the group consisting of hepatocytes, epithelial cells, hematopoietic cells, epithelial cells, endothelial cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, macrophages, neutrophils, antigen presenting cells (dendritic cells), fibroblasts, tumor cells and combination thereof.

3. The method of claim 1, wherein the non-lung tissue is selected from the group consisting of heart, liver, spleen, kidneys, skeletal muscle, lymph nodes, skin, brain, cerebrospinal fluid, plasma and combination thereof.

4. The method of claim 1, wherein the mRNA encodes a protein selected from the group consisting of a cytosolic protein, a secreted protein and a therapeutic protein.

5. The method of claim 4, wherein the cytosolic protein is selected from the group consisting of enzymes, transcription factors, chaperones, and combination thereof.

6. The method of claim 4, wherein the therapeutic protein is selected from the group consisting of alpha galactosidase, erythropoietin, a1-antitrypsin, carboxypeptidase N, alpha-L-iduronidase, iduronate-2-sulfatase, N-acetylglucosamine-1-phosphate transferase, N-acetylglucosaminidase, lysosomal acid lipase, arylsulfatase-A alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase, galactocerebrosidase, human growth hormone, ornithine transcarbamylase (OTC), carbamyl phosphate synthetase-1 (CPS1), argininosuccinate synthetase-1 (ASS1), argininosuccinate lyase (ASL), arginase-1 (ARG1), cystic fibrosis transmembrane conductance regulator (CFTR), Factor VII, Factor VIII, Factor IX, heparan-N-sulfatase, and combination thereof.

7. The method of claim 1, wherein the protein is detectable in the non-lung cell or tissue for at least about 1 day or for at least about 2 days following the administration to the lung.

8. The method of claim 1, wherein the mRNA is delivered at an amount greater than about 0.5 mg/kg of mRNA per dose.

9. The method of claim 1, wherein the lipid carrier vehicle is a liposome.

10. The method of claim 9, wherein the liposome further comprises one or more cationic lipids, one or more non-cationic lipids, and one or more cholesterol-based lipids.

11. The method of claim 10, wherein the one or more cationic lipids are selected from the group consisting of C12-200, HGT4003, HGT5000, HGT5001, ICE, DLinKC2-DMA, DODAP, DODMA, DLinDMA, CLinDMA, and combination thereof.

12. The method of claim 1, wherein the composition further comprises one or more pulmonary surfactants.

13. The method of claim 1, wherein the composition is formulated as respirable particles.

14. The method of claim 13, wherein the respirable particles have a size less than about 500 μm.

15. The method of claim 1, wherein the composition is formulated as nebulizable lipid or as dry powder.

16. The method of claim 1, wherein the non-lung cell or tissue is affected by a disease or disorder.

17. The method of claim 16, wherein the disease or disorder is selected from Table 4.

18. The method of claim 1, wherein the mRNA is unmodified.

* * * * *

SEQUENCE LISTING

```
<160> NUMBER OF SEQ ID NOS: 2

<210> SEQ ID NO 1
<211> LENGTH: 140
<212> TYPE: RNA
<213> ORGANISM: Artificial Sequence
<220> FEATURE:
<223> OTHER INFORMATION: 5' UTR from CMV immediate-early (1E1) gene
<220> FEATURE:
<221> NAME/KEY: misc_feature
<222> LOCATION: (1)..(1)
<223> OTHER INFORMATION: n is absent or G
<220> FEATURE:
<221> NAME/KEY: misc_feature
<222> LOCATION: (2)..(2)
<223> OTHER INFORMATION: n is absent or G
<220> FEATURE:
<221> NAME/KEY: misc_feature
<222> LOCATION: (3)..(3)
<223> OTHER INFORMATION: n is absent or A

<400> SEQUENCE: 1
nnncagaucg ccuggagacg ccauccacgc uguuuugacc uccauagaag acaccgggac     60
cgauccagcc uccgcggccg ggaacggugc auuggaacgc ggauucccg ugccaagagu    120 gacucaccgu ccuugacacg                                                140

<210> SEQ ID NO 2
<211> LENGTH: 100
<212> TYPE: RNA
<213> ORGANISM: Artificial Sequence
<220> FEATURE:
<223> OTHER INFORMATION: 3' UTR sequence from the Human Growth Hormone
      (hGH) gene
```

-continued

```
<400> SEQUENCE: 2
cggguggcau cccugugacc ccuccccagu gccucuccug gcccuggaag uugccacucc     60
agugcccacc agccuuguccuaauaaaauu aaguugcauc                            100
```